United States Patent
Huang et al.

(10) Patent No.: US 11,795,487 B2
(45) Date of Patent: Oct. 24, 2023

(54) FUNGAL CELL WITH IMPROVED PROTEIN PRODUCTION CAPACITY

(71) Applicant: Melt & Marble AB, Gothenburg (SE)

(72) Inventors: Mingtao Huang, Gothenburg (SE); Anastasia Krivoruchko, Gothenburg (SE); Florian David, Gothenburg (SE); Jens Nielsen, Gothenburg (SE)

(73) Assignee: Melt & Marble AB, Gothenburg (SE)

( * ) Notice: Subject to any disclaimer, the term of this patent is extended or adjusted under 35 U.S.C. 154(b) by 0 days.

(21) Appl. No.: 16/634,267

(22) PCT Filed: Jul. 30, 2018

(86) PCT No.: PCT/SE2018/050779
§ 371 (c)(1),
(2) Date: Jan. 27, 2020

(87) PCT Pub. No.: WO2019/027364
PCT Pub. Date: Feb. 7, 2019

(65) Prior Publication Data
US 2020/0299742 A1 Sep. 24, 2020

(30) Foreign Application Priority Data
Jul. 31, 2017 (SE) .................... 1750968-8

(51) Int. Cl.
C12P 21/00 (2006.01)
C07K 14/39 (2006.01)
C07K 14/395 (2006.01)

(52) U.S. Cl.
CPC ............ C12P 21/00 (2013.01); C07K 14/395 (2013.01)

(58) Field of Classification Search
CPC ............................... C12P 21/00; C07K 14/395
See application file for complete search history.

(56) References Cited

U.S. PATENT DOCUMENTS

2013/0011875 A1* 1/2013 Meehl .................. C12P 21/005
435/254.23

FOREIGN PATENT DOCUMENTS

WO 2004/003217 1/2004
WO 2013/102674 7/2013

OTHER PUBLICATIONS

Morvan et al., J. Cell. Sci., 128(4), 706-716, 2015.*
National Inst. of Health Batten disease fact sheet, May 17, 2021.*
Legner E.F., Univ. California Riverside, Netlinks to families of the Fungi Kingdom, 2020.*
Huang et al., PNAS, Published online Aug. 2015, E4689-E4696.*
International Search Report and Written Opinion corresponding to International Patent Application No. PCT/SE2018/050779, dated Oct. 8, 2018, 10 pages.
Kanneganti et al. "Btn3 is negative regulator of Btn2-mediated endosomal protein trafficking and prion curing in yeast" Molecular Biology of the Cell, 22(10):1648-1663 (2011).
True, Heather L., et al., "A yeast prion provides a mechanism for genetic variation and phenotypic diversity", Nature. 407: 477-483 (2000).
Tyedmers, Jens, et al., "Prion Switching in Response to Environmental Stress", PLoS Biology. 6(11): e294, 2605-2613 (2008).
Huang, et al., "Appendix 1 for Engineering the protein secretory pathway of Saccharomyces cerevisiae enables improved protein production", PNAS 115(47) E11025-E11032 (2018). Retrieved from www.pnas.org/cgi/doi/10.1073/pnas.1809921115 on May 17, 2023.
Huang, et al., "Supporting Information for Microfluidic screening and whole-genome sequencing identifies mutations associated with improved protein secretion by yeast", PNAS 112 (34) E4689-E4696 (2015). Retrieved from www.pnas.org/lookup/suppl/doi:10.1073/pnas.1506460112/-/DCSupplemental on May 17, 2023.

* cited by examiner

*Primary Examiner* — Maryam Monshipouri
(74) *Attorney, Agent, or Firm* — Myers Bigel, P.A.

(57) ABSTRACT

The present invention related to the provision of genetically modified fungal cells, such as yeast cells with an improved ability for producing and secreting different recombinant proteins. The improved ability is obtained by disruption in intracellular transport between the Golgi and the endosome. In particular embodiments, the disruption is achieved by downregulation or deletion of the gene encoding a Tda3p homolog. The fungal cell and method of the invention would allow for large-scale production of recombinant proteins in fungal cells.

5 Claims, 8 Drawing Sheets
Specification includes a Sequence Listing.

FUNGAL CELL WITH IMPROVED PROTEIN PRODUCTION CAPACITY

TECHNICAL FIELD

The present invention relates generally to the development of genetically engineered microorganisms. More specifically the invention relates to fungal cells containing modifications allowing production and secretion of high levels of recombinant proteins.

BACKGROUND

Production of recombinant proteins by fungal cells plays an important role in various industries. For example, various industrial enzymes and biopharmaceuticals are produced by fungal systems. It is therefore desirable to develop fungal platform strains that are able to produce high levels of different recombinant proteins.

Various research efforts have been aimed at creating platform strains for protein production via genetic engineering of the host cell. For example, several studies have aimed to increase recombinant protein production by increasing the protein folding capacity of the cell. Tang et al (Biotechnol Bioeng. 2015 September; 112(9):1872-82. doi: 10.1002/bit.25596) over-expressed the endoplasmic reticulum (ER) chaperone protein BiP and the disulfide isomerase Pdi1p in yeast, and thereby managed to increase the secretion of three heterologous proteins, β-glucosidase, endoglucanase, and α-amylase. In addition Hou et al (Appl Microbiol Biotechnol. 2013 April; 97(8):3559-68. doi: 10.1007/s00253-012-4596-9.) showed that overexpression of HSF1, a transcription factor that controls the expression of multiple protein chaperones, led to increased production of heterologous α-amylase, endogenous invertase and human insulin precursor. Another transcription factor, HAC1, is involved in the general unfolded protein response. It facilitates the expression of PDI or BiP in a cell, and has been successfully employed to obtain improved levels of production of antibodies by Gasser et al (Biotechnol Bioeng. 2006 Jun. 5; 94(2):353-61.). Koskela et al (Biotechnol J. 2017 Apr. 21. doi: 10.1002/biot.201600631.) showed that expression of mammalian BiP, the co-chaperone GRP170, or the peptidyl-prolyl isomerase FKBP2 increased antibody production in yeast. De Ruijter et al (Microb Cell Fact. 2016 May 23; 15:87. doi: 10.1186/s12934-016-0488-5.) have also shown that overexpression of the folding factor Cpr5p could lead to increased antibody production.

Other studies have focused on proteases and showed that deletion of proteases could lead to increased protein production. Tomimoto et al (Biosci Biotechnol Biochem. 2013; 77:2461-6) were able to obtain higher production of human interferon-β in yeast by disruption of the proteases encoded by PEP4 and PRB1. Furthermore, Choo et al (J Biotechnol. 2010 Aug. 20; 149:1-7. doi: 10.1016/j.jbiotec.2010.06.014.) showed that disruption of various yapsin proteases reduced proteolytic degradation of human parathyroid hormone protein during fermentation.

Other studies have involved engineering of intracellular trafficking. Hou et al (Metab Eng. 2012 March; 14(2):120-7. doi: 10.1016/j.ymben.2012.01.002) have shown that overexpression of Sec1p, a protein that is involved in exocytosis in *S. cerevisiae*, led to increased secretion of heterologous proteins human insulin precursor and α-amylase, and also the secretion of an endogenous protein invertase around 1.5×.

Other studies have also attempted to engineer the components involved in vesicle trafficking from the endoplasmic reticulum (ER) to the Golgi, and from the Golgi to the plasma membrane (PM). Bao et al (Appl Environ Microbiol. 2017. 5. pii: AEM.03400-16. doi: 10.1128/AEM.03400-16.) have shown that overexpression of Sec16p, a protein involved in transport between the ER and the Golgi, led to increased secretion of heterologous α-amylase. Tang et al (Biotechnol Biofuels. 2017 Feb. 27; 10:53. doi: 10.1186/s13068-017-738-8.) showed that engineering the targeted components in the ER to Golgi vesicle trafficking, including Sec12p, Sec13p, Erv25p and Bos1p, enhanced the extracellular activity of heterologous endoglucanase. In addition, over-expression of the components in the Golgi to plasma membrane vesicle trafficking, including Sso1p, Snc2p, Sec1p, Exo70p, Ypt32p and Sec4p, led to increased secretion of β-glucosidase. Van Zyl et al (Appl Microbiol Biotechnol. 2016 January; 100:505-18. doi: 10.1007/s00253-015-7022-2.) have also demonstrated that production of heterologous cellobiohydrolase and β-glucosidase could be increased by single and co-overexpression of some of the endoplasmic reticulum (ER)-to-Golgi SNAREs (BOS1, BET1, SEC22 and SED5). Furthermore, the patent application US 2013/0011875 A1, discloses a *Pichia pastoris* cell with disrupted vacuolar sorting activity, wherein the disruption occurs through deletion of vacuolar protein sorting receptor 10 (Vps10), as well as disruption of one or more genes that encode a protein associated with recycling of Vps10 to the late Golgi.

A study by Huang et al (Proc Natl Acad Sci USA. 2015 Aug. 25; 112(34):E4689-96. doi: 10.1073/pnas.1506460112.) reported combination of UV mutagenesis and microfluidic sorting to uncover potential targets and reported that deletion of HDA2, HDA3 and SNC2 in yeast results in increased protein production.

TDA3 (also known as BTN3) is a putative oxidoreductase and was shown to interact with both epsins Ent3 and Ent5. TDA3 is a negative regulator of the Batten-disease-linked protein Btn2 involved in the retrieval of specific SNAREs (Vti1, Snc1, Tlg1 and Tlg2) from the late endosome to the Golgi. It was suggested that TDA3 sequesters Btn2 away from its substrates, thus down-regulating protein trafficking and aggregation. It was shown that in btn3Δ mutant cells, endosomal sorting of ubiquitylated cargos and endosomal recycling of the Snc1 SNARE are delayed.

COG5 is a component of the conserved oligomeric Golgi complex that functions in protein trafficking to mediate fusion of transport vesicles to Golgi compartments

SUMMARY

It is a general objective to provide an improved fungal cell.

It is a particular objective to provide a fungal cell that can be used for fermentation-based production of recombinant proteins.

These and other objectives are met by embodiments as disclosed herein.

An aspect of the embodiments relates to a fungal cell. According to the embodiments, the fungal cell lacks a gene encoding Tda3p or comprises a disrupted endogenous gene encoding Tda3p. The fungal cell also comprises a gene encoding a recombinant protein.

Another aspect of the embodiments relates to a method for producing a recombinant protein. The method comprises culturing a fungal cell according to any of the embodiments in a culture medium and in culture conditions suitable for production of the recombinant protein by the fungal cell. The method also comprises collecting the recombinant protein from the culture medium and/or from the fungal cell.

The fungal cell of the embodiments comprises modifications to intracellular transport between the Golgi and the endosome, combined with expression of a recombinant protein.

BRIEF DESCRIPTION OF THE DRAWINGS

The embodiments, together with further objects and advantages thereof, may best be understood by making reference to the following description taken together with the accompanying drawings, in which.

DETAILED DESCRIPTION OF THE INVENTION AND PREFERRED EMBODIMENTS THEREOF

Figure 1:
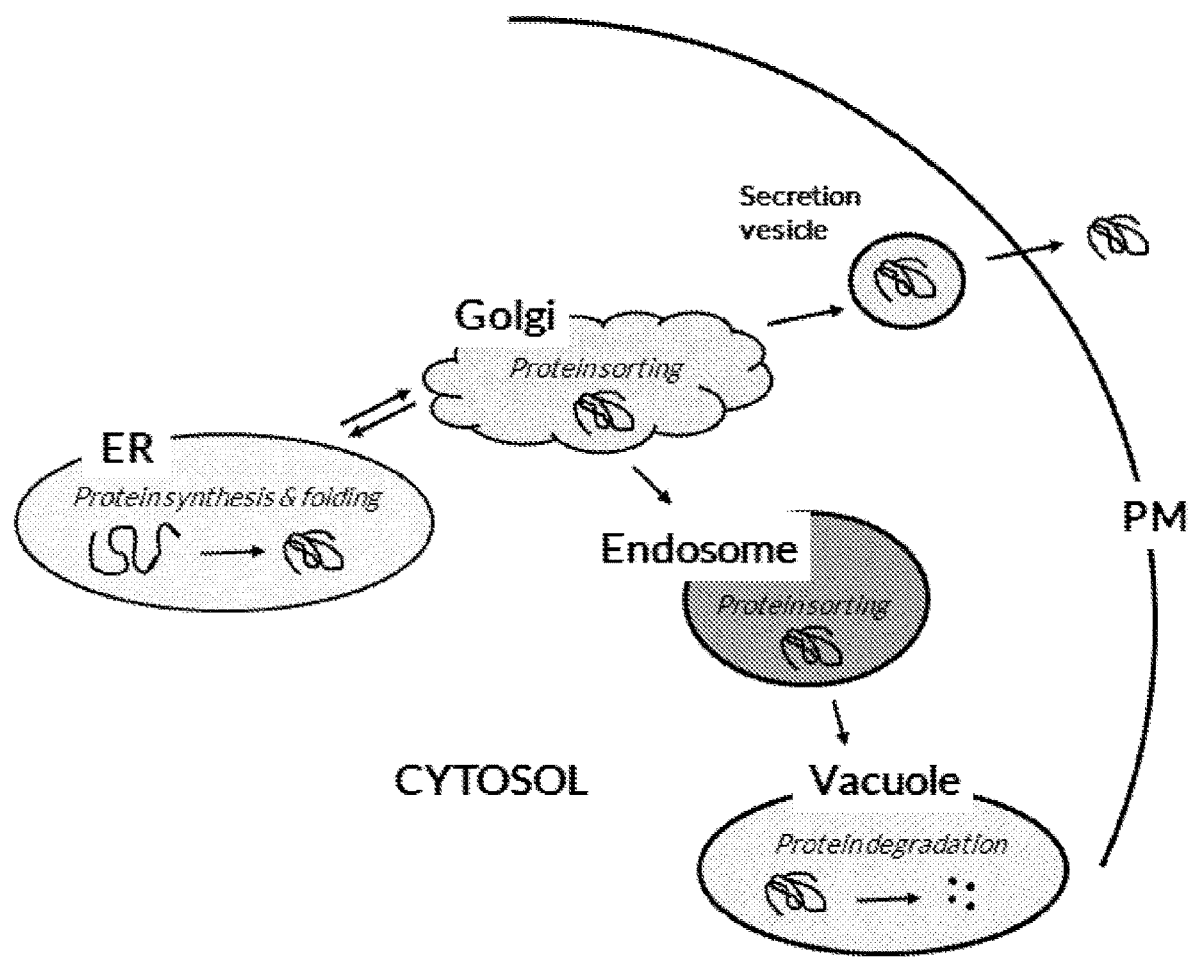
FIG. 1: Overview of the intracellular trafficking in a fungal cell. Proteins are transported from the endoplasmic reticulum (ER) to the Golgi, where they are sorted into anterograde transport vesicles for ER resident proteins, into secretory vesicles for plasma membrane (PM) and secretion, and into vacuolar protein sorting vesicles for vacuolar proteins passing through the endosomes. The present invention involves disruption of transport between the Golgi and the endosome.

The present invention now will be described hereinafter with reference to the accompanying drawings and examples, in which embodiments of the invention are shown. This description is not intended to be a detailed catalogue of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined herein, scientific and technical terms used herein will have the meanings that are commonly understood by those of ordinary skill in the art.

Generally, nomenclatures used in connection with techniques of biochemistry, enzymology, molecular and cellular biology, microbiology, genetics and protein and nucleic acid chemistry and hybridization, described herein, are those well-known and commonly used in the art.

Conventional methods and techniques mentioned herein are explained in more detail, for example, in Molecular Cloning, a laboratory manual [second edition] Sambrook et al. Cold Spring Harbor Laboratory, 1989, for example in Sections 1.21 "Extraction And Purification Of Plasmid DNA", 1.53 "Strategies For Cloning In Plasmid Vectors", 1.85 "Identification Of Bacterial Colonies That Contain Recombinant Plasmids", 6 "Gel Electrophoresis Of DNA", 14 "In vitro Amplification Of DNA By The Polymerase Chain Reaction", and 17 "Expression Of Cloned Genes In *Escherichia coli*" thereof.

Enzyme Commission (EC) numbers (also called "classes" herein), referred to throughout this specification, are according to the Nomenclature Committee of the International Union of Biochemistry and Molecular Biology (NC-IUBMB) in its resource "Enzyme Nomenclature" (1992, including Supplements 6-17) available, for example, as "Enzyme nomenclature 1992: recommendations of the Nomenclature Committee of the International Union of Biochemistry and Molecular Biology on the nomenclature and classification of enzymes", Webb, E. C. (1992), San Diego: Published for the International Union of Biochemistry and Molecular Biology by Academic Press (ISBN 0-12-227164-5). This is a numerical classification scheme based on the chemical reactions catalyzed by each enzyme class.

The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

As used herein, the transitional phrase "consisting" essentially of means that the scope of a claim is to be interpreted to encompass the specified materials or steps recited in the claim and those that do not materially affect the basic and novel characteristic(s) of the claimed invention. Thus, the term "consisting essentially of when used in a claim of this invention is not intended to be interpreted to be equivalent to "comprising."

To facilitate understanding of the invention, a number of terms are defined below.

Also as used herein, the terms "nucleotide sequence" "nucleic acid," "nucleic acid molecule," "oligonucleotide" and "polynucleotide" refer to RNA or DNA, including cDNA, a DNA fragment or portion, genomic DNA, synthetic DNA, plasmid DNA, mRNA, and anti-sense RNA, any of which can be single stranded or double stranded, linear or branched, or a hybrid thereof. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein the term "recombinant" when applied to nucleic acid means that a particular nucleic acid (DNA or RNA) is the product of various combinations of fusion, cloning, restriction, genetic recombination and/or ligation steps resulting in a construct having a structural coding or non-coding sequence distinguishable from endogenous nucleic acids found in natural systems. The term "recombinant protein" refers to protein that can result from the expression of recombinant DNA within a cell.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions, e.g. introns, regulatory elements, promoters, enhancers, termination sequences and/or 5' and 3' untranslated regions. A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "disrupted gene" as defined herein involves any mutation or modification to a gene resulting in a partial or fully non-functional gene and gene product. Such a mutation or modification includes, but is not limited to, a missense mutation, a nonsense mutation, a deletion, a substitution, an insertion, addition of a targeting sequence and the like. Furthermore, a disruption of a gene can be achieved also, or alternatively, by mutation or modification of control elements controlling the transcription of the gene, such as mutation or modification in a promoter, terminator and/or enhancement elements. In such a case, such a mutation or modification results in partially or fully loss of transcription of the gene, i.e. a lower or reduced transcription as compared to native and non-modified control elements. As a result a reduced, if any, amount of the gene product will be available following transcription and translation. Furthermore, disruption of a gene could also entail adding or removing a localization signal from the gene, resulting in decreased presence of the gene product in its native subcellular compartment.

The objective of gene disruption is to reduce the available amount of the gene product, including fully preventing any production of the gene product, or to express a gene product that lacks or having lower enzymatic activity as compared to the native or wild type gene product.

A "codon optimized" version of a gene refers to an exogenous gene introduced into a cell and where the codons of the gene have been optimized with regard to the particular cell. Generally, not all tRNAs are expressed equally or at the same level across species. Codon optimization of a gene sequence thereby involves changing codons to match the most prevalent tRNAs, i.e. to change a codon recognized by a low prevalent tRNA with a synonymous codon recognized by a tRNA that is comparatively more prevalent in the given cell. This way the mRNA from the codon optimized gene will be more efficiently translated. The codon and the synonymous codon preferably encode the same amino acid.

As used herein, the term "allele" refers to a variant form of a given gene. This can include a mutated form of a gene where one or more of the amino acids encoded by the gene have been removed or substituted by a different amino acid.

As used herein, the terms "peptide", "polypeptide", and "protein" are used interchangeably to indicate to a polymer of amino acid residues. The terms "peptide", "polypeptide" and "protein" also includes modifications including, but not limited to, lipid attachment, glycosylation, glycosylation, sulfation, hydroxylation, γ-carboxylation of L-glutamic acid residues and ADP-ribosylation.

As used herein, the term "enzyme" is defined as a protein which catalyzes a chemical or a biochemical reaction in a cell. Usually, according to the present invention, the nucleotide sequence encoding an enzyme is operably linked to a nucleotide sequence (promoter) that causes sufficient expression of the corresponding gene in the cell to confer to the cell the ability to produce desired metabolites.

As used herein, the term "open reading frame (ORF)" refers to a region of RNA or DNA encoding polypeptide, a peptide, or protein.

As used herein, the term "genome" encompasses both the plasmids and chromosomes in a host cell. For instance, encoding nucleic acids of the present disclosure which are introduced into host cells can be portion of the genome whether they are chromosomally integrated or plasmids-localized.

As used herein, the term "promoter" refers to a nucleic acid sequence which has functions to control the transcription of one or more genes, which is located upstream with respect to the direction of transcription of the transcription initiation site of the gene. Suitable promoters in this context include both constitutive and inducible natural promoters as well as engineered promoters, which are well known to the person skilled in the art.

Suitable promoters for use in fungal cells may be the promoters of PDC, GPD1, TEF1, PGK1 and TDH. Other suitable promoters include the promoters of GAL1, GAL2, GAL10, GAL7, CUP1, HIS3, CYC1, ADH1, PGL, GAPDH, ADC1, URA3, TRP1, LEU2, TPI, AOX1 and ENO1.

As used herein, the term "terminator" refers to a "transcription termination signal" if not otherwise noted. Terminators are sequences that hinder or stop transcription of a polymerase.

As used herein, "recombinant fungal cells" according to the present disclose is defined as cells which contain additional copies or copy of an endogenous nucleic acid sequence or are transformed or genetically modified with polypeptide or a nucleotide sequence that does not naturally occur in the fungal cells. The wildtype fungal cells are defined as the parental cells of the recombinant fungal cells, as used herein.

As used herein, the terms "increase," "increases," "increased," "increasing," "enhance," "enhanced," "enhancing," and "enhancement" (and grammatical variations thereof) indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

As used herein, the terms "reduce," "reduces," "reduced," "reduction," "diminish," "suppress," and "decrease" and similar terms mean a decrease of at least about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

A "reduced expression" of a gene as used herein involves a genetic modification that reduces the transcription of the gene, reduces the translation of the mRNA transcribed from the gene and/or reduces post-translational processing of the protein translated from the mRNA. Such genetic modification includes insertion(s), deletion(s), replacement s) or mutation(s) applied to the control sequence, such as a promoter and enhancer, of the gene. For instance, the promoter of the gene could be replaced by a less active or inducible promoter to thereby result in a reduced transcription of the gene. Also a knock-out of the promoter would result in reduced, typically zero, expression of the gene.

As used herein the terms "knock-out" or "deletion" or "disruption" refers to a gene that is inoperative or knocked out and/or a nonfunctional gene product, e.g. a polypeptide having essentially no activity, e.g. less than about 10% or even 5% as compared to the activity of the wild type polypeptide.

As used herein, the term "portion" or "fragment" of a nucleotide sequence of the invention will be understood to mean a nucleotide sequence of reduced length relative to a reference nucleic acid or nucleotide sequence and comprising, consisting essentially of and/or consisting of a nucleotide sequence of contiguous nucleotides identical or almost identical, e.g. 80%, 81%, 82%, 83%, 84%, 85%, 86%, 87%, 88%, 89%, 90%, 91%, 92%, 93%, 94%, 95%, 96%, 98%, 99% identical, to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity, i.e. sequence similarity or identity. Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity, e.g. at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%, to said nucleotide sequence.

The term "overexpress," "overexpresses" or "overexpression" as used herein refers to higher levels of activity of a gene, e.g. transcription of the gene; higher levels of translation of mRNA into protein; and/or higher levels of production of a gene product, e.g. polypeptide, than would be in the cell in its native or control, e.g. not transformed with the particular heterologous or recombinant polypeptides being overexpressed, state. A typical example of an overexpressed gene is a gene under transcription control of another promoter as compared to the native promoter of the gene. Also, or alternatively, other changes in the control elements of a gene, such as enhancers, could be used to overexpress the particular gene. Furthermore, modifications that affect, i.e. increase, the translation of the mRNA transcribed from the gene could, alternatively or in addition, be used to achieve an overexpressed gene as used herein. These terms can also refer to an increase in the number of copies of a gene and/or an increase in the amount of mRNA and/or gene product in the cell. Overexpression can result in levels that are 25%, 50%, 100%, 200%, 500%, 1000%, 2000% or higher in the cell, or any range therein, as compared to control levels.

As used herein, the terms "exogenous" or "heterologous" when used with respect to a nucleic acid (RNA or DNA), protein or gene refer to a nucleic acid, protein or gene which occurs non-naturally as part of the cell, organism, genome, RNA or DNA sequence into which it is introduced, including non-naturally occurring multiple copies of a naturally occurring nucleotide sequence. Such an exogenous gene could be a gene from another species or strain, a modified, mutated or evolved version of a gene naturally occurring in the host cell or a chimeric version of a gene naturally occurring in the host cell or fusion genes. In these former cases, the modification, mutation or evolution causes a change in the nucleotide sequence of the gene to thereby obtain a modified, mutated or evolved gene with another nucleotide sequence as compared to the gene naturally occurring in the host cell. Evolved gene refers to genes encoding evolved genes and obtained by genetic modification, such as mutation or exposure to an evolutionary pressure, to derive a new gene with a different nucleotide sequence as compared to the wild type or native gene. A chimeric gene is formed through the combination of portions of one or more coding sequences to produce a new gene. These modifications are distinct from a fusion gene, which merges whole gene sequences into a single reading frame and often retain their original functions.

An "endogenous", "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

As used herein, the term "modified", when it is used with respect to an organism, refers to a host organism that has been modified to increase production of proteins, as compared with an otherwise identical host organism that has not been so modified. In principle, such "modification" in accordance with the present disclosure may comprise any physiological, genetic, chemical, or other modification that appropriately alters production of proteins in a host organism as compared with such production in an otherwise identical organism which is not subject to the said modification. In most of the embodiments, however, the modification will comprise a genetic modification. In certain embodiments, as described herein, the modification comprises introducing genes into a host cell, and particularly into a host cell which is disrupted in the Golgi-endosome trafficking. In some embodiments, a modification comprises at least one physiological, chemical, genetic, or other modification; in other embodiments, a modification comprises more than one chemical, genetic, physiological, or other modification. In certain aspects where more than one modification is made use of, such modifications can include any combinations of physiological, genetic, chemical, or other modification (e.g., one or more genetic, chemical and/or physiological modification(s)). Genetic modifications which boost the activity of a polypeptide include, but are not limited to: introducing one or more copies of a gene encoding the polypeptide (which may distinguish from any gene already present in the host cell encoding a polypeptide having the same activity); altering a gene present in the cell to increase transcription or translation of the gene (e.g., altering, adding additional sequence to, replacement of one or more nucleotides, deleting sequence from, or swapping for example, regulatory, a promoter or other sequence); and altering the sequence (e.g. non-coding or coding) of a gene encoding the polypeptide to boost activity (e.g., by increasing enzyme activity, decrease feedback inhibition, targeting a specific subcellular location, boost mRNA stability, boost protein stability). Genetic modifications that reduce activity of a polypeptide include, but are not limited to: deleting a portion or all of a gene encoding the polypeptide; inserting a nucleic acid sequence which disrupts a gene encoding the polypeptide; changing a gene present in the cell to reduce transcription or translation of the gene or stability of the mRNA or polypeptide encoded by the gene (for example, by adding additional sequence to, altering, deleting sequence from, replacement of one or more nucleotides, or swapping for example, replacement of one or more nucleotides, a promoter, regulatory or other sequence).

The term "overproducing" is used herein in reference to the production of proteins in a host cell and indicates that the host cell is producing more of protein by virtue of the introduction of nucleic acid sequences which encode different polypeptides involved in the host cell's metabolic pathways or as a result of other modifications as compared with the unmodified host cell or wild-type cell.

As used herein, the term "secretion" or "secreting" refers to the excretion of material, such as proteins from the cell.

As used herein, the term "flux", "metabolic flux" or "carbon flux" refers to the rate of turnover of molecules through a given reaction or a set of reactions. Flux in a metabolic pathway is regulated by the enzymes involved in the pathway. Pathways or reactions characterized by a state of increased flux compared to a control have an increased rate of generation of products from given substrates. Pathways or reactions characterized by a state of decreased flux compared to a control have a decreased rate of generation of products from given substrates. Flux towards products of interest can be increased by removing or decreasing competitive reactions or by increasing the activities of enzymes involved in generation of said products.

As used herein the term "vector" is defined as a linear or circular DNA molecule comprising a polynucleotide encoding a polypeptide of the invention, and which is operably linked to additional nucleotides that ensure its expression.

"Introducing" in the context of a yeast cell means contacting a nucleic acid molecule with the cell in such a manner that the nucleic acid molecule gains access to the interior of the cell. Accordingly, polynucleotides and/or nucleic acid molecules can be introduced yeast cells in a single transformation event, in separate transformation events. Thus, the term "transformation" as used herein refers to the introduction of a heterologous nucleic acid into a cell. Transformation of a yeast cell can be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear genome. Stable transformation as used herein can also refer to a nucleic acid molecule that is maintained extrachromosomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a yeast). Stable transformation of a cell can be detected by, for example, a Northern blot hybridization assay of RNA of the cell with nucleic acid sequences which specifically hybridize with a nucleotide sequence of a nucleic acid molecule introduced into a yeast or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods Transformation can also be detected by direct sequencing and/or hybridization protocols well known in the art.

Embodiments of the present invention also encompass variants of the polypeptides as defined herein. As used herein, a "variant" means a polypeptide in which the amino acid sequence differs from the base sequence from which it is derived in that one or more amino acids within the sequence are substituted for other amino acids. For example, a variant of SEQ ID NO:1 may have an amino acid sequence at least about 50% identical to SEQ ID NO:1, for example, at least about 55%, 60%, 65%, 70%, 75%, 80%, 85%, 90%, 91%, 92%, 93%, 94%, 95%, 96%, 97%, 98%, 99% or about 100% identical. The variants and/or fragments are functional variants/fragments in that the variant sequence has similar or identical functional enzyme activity characteristics to the enzyme having the non-variant amino acid sequence specified herein (and this is the meaning of the term "functional variant" as used throughout this specification).

A "functional variant" or "functional fragment" of any of the above amino acid sequences, therefore, is any amino acid sequence which remains within the same enzyme category (i.e., has the same EC number) as the non-variant sequences. Methods of determining whether an enzyme falls within a particular category are well known to the skilled person, who can determine the enzyme category without use of inventive skill. Suitable methods may, for example, be obtained from the International Union of Biochemistry and Molecular Biology.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

Class Amino Acid Examples
Nonpolar: A, V, L, I, P, M, F, W
Uncharged polar: G, S, T, C, Y, N, Q
Acidic: D, E
Basic: K, R, H.

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

In embodiments of the present invention, non-conservative substitutions are possible provided that these do not interrupt the enzyme activities of the polypeptides, as defined elsewhere herein. The substituted versions of the enzymes must retain characteristics such that they remain in the same enzyme class as the non-substituted enzyme, as determined using the NC-IUBMB nomenclature discussed above.

Broadly speaking, fewer non-conservative substitutions than conservative substitutions will be possible without altering the biological activity of the polypeptides. Determination of the effect of any substitution (and, indeed, of any amino acid deletion or insertion) is wholly within the routine capabilities of the skilled person, who can readily determine whether a variant polypeptide retains the enzyme activity according to aspects of the invention. For example, when determining whether a variant of the polypeptide falls within the scope of the invention (i.e., is a "functional variant or fragment" as defined above), the skilled person will determine whether the variant or fragment retains the substrate converting enzyme activity as defined with reference to the NC-IUBMB nomenclature mentioned elsewhere herein. All such variants are within the scope of the invention.

Using the standard genetic code, further nucleic acid sequences encoding the polypeptides may readily be conceived and manufactured by the skilled person, in addition to those disclosed herein. The nucleic acid sequence may be DNA or RNA, and where it is a DNA molecule, it may for example comprise a cDNA or genomic DNA. The nucleic acid may be contained within an expression vector, as described elsewhere herein.

Embodiments of the invention, therefore, encompass variant nucleic acid sequences encoding the polypeptides contemplated by embodiments of the invention. The term "variant" in relation to a nucleic acid sequence means any substitution of, variation of, modification of, replacement of, deletion of, or addition of one or more nucleotide(s) from or to a polynucleotide sequence, providing the resultant polypeptide sequence encoded by the polynucleotide exhibits at least the same or similar enzymatic properties as the polypeptide encoded by the basic sequence. The term includes allelic variants and also includes a polynucleotide (a "probe sequence") which substantially hybridizes to the polynucleotide sequence of embodiments of the present invention. Such hybridization may occur at or between low and high stringency conditions. In general terms, low stringency conditions can be defined as hybridization in which the washing step takes place in a 0.330-0.825 M NaCl buffer solution at a temperature of about 40-48° C. below the calculated or actual melting temperature (Tm) of the probe sequence (for example, about ambient laboratory temperature to about 55° C.), while high stringency conditions involve a wash in a 0.0165-0.0330 M NaCl buffer solution at a temperature of about 5-10° C. below the calculated or actual Tm of the probe sequence (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridization of nucleic acid sequences have been described for example in Molecular Cloning, a laboratory manual [second edition] Sambrook et al. Cold Spring Harbor Laboratory, 1989, for example in Section 11 "Synthetic Oligonucleotide Probes" thereof (herein incorporated by reference)

Preferably, nucleic acid sequence variants have about 55% or more of the nucleotides in common with the nucleic acid sequence of embodiments of the present invention, more preferably at least 60%, 65%, 70%, 80%, 85%, or even 90%, 95%, 98% or 99% or greater sequence identity.

Variant nucleic acids of the invention may be codon-optimized for expression in a particular host cell.

As used herein, "sequence identity" refers to sequence similarity between two nucleotide sequences or two peptide or protein sequences. The similarity is determined by sequence alignment to determine the structural and/or functional relationships between the sequences.

Sequence identity between amino acid sequences can be determined by comparing an alignment of the sequences using the Needleman-Wunsch Global Sequence Alignment Tool available from the National Center for Biotechnology Information (NCBI), Bethesda, Md., USA, for example via ncbi.nlm.nih.gov/Blast.cgi, using default parameter settings (for protein alignment, Gap costs Existence: 11 Extension: 1). Sequence comparisons and percentage identities mentioned in this specification have been determined using this software. When comparing the level of sequence identity to, for example, SEQ ID NO:1, this, preferably should be done relative to the whole length of SEQ ID NO:1 (i.e., a global alignment method is used), to avoid short regions of high identity overlap resulting in a high overall assessment of identity. For example, a short polypeptide fragment having, for example, five amino acids might have a 100% identical sequence to a five amino acid region within the whole of SEQ ID NO:1, but this does not provide a 100% amino acid identity unless the fragment forms part of a longer sequence which also has identical amino acids at other positions equivalent to positions in SEQ ID NO:1. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. As mentioned above, the percentage sequence identity may be determined using the Needleman-Wunsch Global Sequence Alignment tool, using default parameter settings. The Needleman-Wunsch algorithm was published in J. Mol. Biol. (1970) vol. 48:443-53.

An aspect of the embodiments relates to a fungal cell. According to the embodiments, the fungal cell lacks a gene encoding Tda3p or comprises a disrupted endogenous gene encoding Tda3p. The fungal cell also comprises a gene encoding a recombinant protein.

The present embodiments are based on engineering of intracellular trafficking as a means of increasing recombinant protein production in fungal cells. We surprisingly found that by disrupting the transport between the Golgi and the endosome, specifically by disrupting the protein Tda3p, optionally in combination with other targets, such as Gos1p, it was possible to increase recombinant protein production and secretion several fold in the fungal cell.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

In the following, various embodiments of the present invention will be described in more detail.

Preferably, the fungal cell to be modified can be selected from any known genus and species of fungus. In one embodiment, the fungal cell is selected from a group consisting of *Saccharomyces, Kluyveromyces, Zygosaccharomyces, Candida, Hansenula, Torulopsis, Kloeckera, Pichia, Schizosaccharomyces, Trigonopsis, Brettanomyces, Debaromyces, Nadsonia, Lipomyces, Cryptococcus, Aureobasidium, Trichosporon, Lipomyces, Rhodotorula, Yarrowia, Rhodosporidium, Phaffia, Schwanniomyces, Aspergillus*, and *Ashbya, Saccharomyces cerevisiae* is commonly used yeast in industrial processes, but the disclosure is not limited thereto. Other yeast species useful in the present disclosure include but are not limited to *Pichia pastoris, Ashbya gossypii, Saccharomyces boulardii, Zygosaccharomyces bailii, Kluyveromyces lactis, Rhodosporidium toruloides* and *Yarrowia lipolytica*.

In some embodiments, the transport between the Golgi and the endosome is disrupted in the fungal cell. The modification(s) allow(s) for increased production and/or secretion of recombinant proteins in the fungal cell. This can be achieved by downregulation of proteins involved in the transport between the Golgi and the endosome. For example, in *S. cerevisiae*, this includes the proteins Tda3p, Gos1p, Vps5p, Vps17p, Vps10p, Ccz1p, Hse1p, Pep8p, Vps29p, Vps35p, Snx41p, Btn2p, Dop1p, Trs130p, Trs120p, Snx4p, Fab1p, Ypt7p, Ent5p, Vps53p, Laa1p, Atg20p, Vps52p, Sft1p, Sft2p, Vps51p, Ent3p, Snx3p, Ypt31p, Vps54p, Ypt32p, Ykt6p Mvp1p, Tlg1p, Trs65p, Tca17p, Rcy1p, Ypt6p, Vti1p, Rgp1p, Ric1p, Got1p, Rhb1p, Gga1p, Gga2p, Mon2p, Vta1p and Vps45p. These proteins are encoded by the genes TDA3, GOS1, VPS5, VPS17, VPS10, CCZ1, HSE1, PEP8, VPS29, VPS35, SNX41, BTN2, DOP1, TRS130, TRS120, SNX4, FAB1, YPT7, ENT5, YKR078W, VPS53, LAA1, ATG20, VPS52, SFT1, SFT2, VPS51, ENT3, SNX3, YPT31, VPS54, YPT32, YKT6, MVP1, TLG1, TLG2, TRS65, TCA17, RCY1, YPT6, VTI1, RGP1, RIC1, GOT1, RHB, GGA1, GGA2, MON2, VTA1 and VPS45, respectively.

In a preferred embodiment, the modifications to the transport between the Golgi and the endosome involve disruption of Tda3p (SEQ ID NO: 1). This could be achieved by deleting the endogenous gene coding for this protein. For example, the endogenous TDA3 gene encoding Tda3p could be deleted in *S. cerevisiae*. Thus, the fungal cell preferably lacks a gene encoding Tda3p or comprises a disrupted endogenous gene encoding Tda3p.

In another embodiment, the modifications to the transport between the Golgi and the endosome involve disruption of Gos1p (SEQ ID NO: 2). This could be achieved by deleting the endogenous gene coding for this protein. For example, the endogenous GOS1 gene encoding Gos1p could be deleted in *S. cerevisiae*.

Thus, another aspect of the embodiments relates to a fungal cell. According to the embodiments, the fungal cell lacks a gene encoding Gos1p or comprises a disrupted endogenous gene encoding Gos1p. The fungal cell also comprises a gene encoding a recombinant protein.

Hence, in an embodiment, the fungal cell lacks a gene encoding Gos1p or comprises a disrupted endogenous gene encoding Gos1p.

The two aspects described above can be combined. In such an approach, the fungal cells lacks a gene encoding Tda3p and lacks a gene encoding Gos1p; lacks a gene encoding Tda3p and comprises a disrupted endogenous gene encoding Gos1p; lacks a gene encoding Gos1p and comprises a disrupted endogenous gene encoding Tda3p; or comprises a disrupted endogenous gene encoding Tda3p and comprises a disrupted endogenous gene encoding Gos1p. The fungal cell also comprises a gene encoding a recombinant protein.

In an embodiment, any of the modifications above or below are combined with downregulation of proteins that form the retromer complex for transport from endosome to Golgi. This could be achieved by disrupting some of the proteins that make up this complex, such as Vps5p (SEQ ID NO: 3), Vps17p (SEQ ID NO: 4), Pep8p (SEQ ID NO: 5), Vps29p (SEQ ID NO: 6) and/or Vps35p (SEQ ID NO: 7). For example, the endogenous genes VPS5, VPS17, PEP8, VPS29 and/or VPS35 that make up this complex could be deleted in S. cerevisiae.

Thus, in an embodiment, the fungal cell comprises a disrupted endogenous retromer complex for transport from endosome to Golgi.

In a particular embodiment, the fungal cell is genetically modified for reduced expression of at least one protein selected from a group consisting of Vps5p (SEQ ID NO: 3), Vps17p (SEQ ID NO: 4), Pep8p (SEQ ID NO: 5), Vps29p (SEQ ID NO: 6), Vps35p (SEQ ID NO:7), and variants thereof having at least 50% homology to any of SEQ ID NO: 3-7).

In another embodiment, recombinant protein production in a fungal cell could be further increased by combining any modifications above or below with disruption in proteins that act as subunits of the HDA1 histone deacetylase complex. Deletion of such subunits increases protein production. Disruption of the HDA1 histone deacetylase complex could be achieved, for example, by disrupting the proteins that make up this complex, such as Hda2p (SEQ ID NO: 8) and/or Hda3p (SEQ ID NO: 9). This could be achieved by deleting the endogenous HDA2 and/or HDA3 genes encoding subunits of the HDA1 histone deacetylase complex in S. cerevisiae.

Thus, in an embodiment, the fungal cell lacks genes encoding subunits of HDA1 histone deacetylase complex, preferably at least one of Hda2p and Hda3p, or comprises disrupted endogenous genes encoding the subunits of HDA1 histone deacetylase complex, preferably at least one of Hda2p and Hda3p.

In another embodiment, recombinant protein production in a fungal cell could be increased by disruption of Pgm2p (SEQ ID NO: 10), encoding phosphoglucomutase, also referred to as phosphoglucomutase (alpha-D-glucose-1,6-bisphosphate-dependent) (EC 5.4.2.2). This can be achieved, for example, by deleting the endogenous gene encoding phosphoglucomutase. For example, the genes PGM2 and/or PGM1 could be deleted in S. cerevisiae.

Thus, in an embodiment, the fungal cell lacks genes encoding Pgm2p and/or Pgm1p or comprises a disrupted endogenous gene encoding Pgm2p and/or Pgm1p.

In another embodiment, recombinant protein production in a fungal cell could be increased by disruption of subunits of peroxisomal ABC transport complex. This can be achieved, for example, by deleting the endogenous genes encoding subunits of peroxisomal ABC transport complex, such as Pxa1p (SEQ ID NO: 11) and/or Pxa2p (SEQ ID NO: 12). For example, the gene PXA1 and/or PXA2 could be deleted in S. cerevisiae.

Thus, in an embodiment, the fungal cell lacks genes encoding subunits of peroxisomal ABC transport complex, preferably at least one of Pxa1p and Pxa2p, or comprises disrupted endogenous genes encoding the subunits of peroxisomal ABC transport complex, preferably at least one of Pxa1P and Pxa2p.

In another embodiment, recombinant protein production in a fungal cell could be increased by disruption of members of the conserved endoplasmic reticulum membrane complex. For example, Emc1p (SEQ ID NO: 13) could be disrupted. This can be achieved, for example, by deletion of the endogenous EMC1 gene in S. cerevisiae.

Thus, in an embodiment, the fungal cell lacks genes encoding members of the conserved endoplasmic reticulum membrane complex, preferably Emc1p, or comprises disrupted endogenous genes encoding the members of the conserved endoplasmic reticulum membrane complex, preferably Emc1p.

In another embodiment, recombinant protein production in a fungal cell could be increased by disruption of vesicle membrane receptor proteins, for example Snc1p (SEQ ID NO: 14) and/or Snc2p (SEQ ID NO: 15). This can be achieved, for example, by deletion of the endogenous SNC1 and/or SNC2 gene in S. cerevisiae.

Thus, in an embodiment, the fungal cell lacks genes encoding vesicle membrane receptor proteins, preferably at least one of Snc1p and Snc2p, or comprises disrupted endogenous genes encoding the vesicle membrane receptor proteins, preferably at least one of Snc1p and Snc2p.

In another embodiment recombinant protein production in a fungal cell could be increased by increasing the levels of proteins that act as components of the cytosolic tethering complex, such as Cog1p, Cog2p, Cog3p, Cog4p, Cog5p, Cog6p, Cog7p and/or Cog8p. This can be achieved through overexpression of the endogenous genes encoding these proteins. For example, in a preferred embodiment, the endogenous Cog5p (SEQ ID NO: 16) protein is overexpressed in S. cerevisiae.

Thus, in an embodiment, the fungal cell is genetically modified for enhanced expression of at least one component of the cytosolic tethering complex, preferably the at least one component is selected from a group consisting of Cog1p, Cog2p, Cog3p, Cog4p, Cog5p, Cog6p, Cog7p and Cog8p.

In another embodiment, recombinant protein production in a fungal cell could be increased by combining any of the modifications described above or below with increases in the activities of chaperone proteins. This can be achieved by overexpression of proteins that act as chaperones. For example, the activity of the enzyme protein disulfide isomerase (PDI) (EC 5.3.4.1) could be increased by overexpression of the endogenous PDI1 gene (SEQ ID NO: 17) in S. cerevisiae. This includes PDI yeast homologs, such as PDI1, MPD1, MPD2, EUG1, and EPS1. Alternatively, or in addition, other chaperones could be overexpressed. For example, Binding immunoglobulin protein (BiP), encoded by KAR2 in S. cerevisiae, the thiol oxidase ERO1, encoded by ERO1, the Sm-like proteins SEC1 or SLY1, encoded by SEC1 and SLY1 could be overexpressed. Chaperones from other species could also, or alternatively, be introduced. For example, the mammalian co-chaperone GRP170 and the peptidyl-prolyl isomerase FKBP2 could be overexpressed in S. cerevisiae. Other genes that could be introduced into a fungal cell to further improve protein production include Dsbc and FkpA from *Escherichia coli* and *S. cerevisiae* peptidyl-prolyl cis-trans isomerase (encoded by CPR5).

In an embodiment, the fungal cell is genetically modified for enhanced expression of at least one endogenous chaperone protein, preferably the at least one endogenous protein is selected from a group consisting of Pd1p, Mpd1p, Mpd2p, Eug1p, Eps1p, Kar2p, Ero1p, Sec1p, Sly1p and Cpr5p.

In an embodiment, the fungal cell comprises at least one heterologous gene encoding a respective heterologous chaperone protein, preferably the respective heterologous chaperone is selected from a group consisting of mammalian GRP170, mammalian FKBP2, *Escherichia coli* Dsbc and *E. coli* FkpA.

In another embodiment, the activity of transcription factors that control the expression of protein chaperones could be increased in order to further increase recombinant protein production. For example, the activity of the transcription factor heat shock factor (HSF) could be increased by overexpression of the endogenous gene encoding HSF, such as HSF1 (SEQ ID NO: 18) in *S. cerevisiae*. In addition, in another embodiment, a mutant version of HSF1 is expressed. For example, HSF1 from *S. cerevisiae* where arginine 206 is replaced, preferably by Serine (R206S), could be overexpressed in a fungal cell.

In an additional embodiment, the activity of the transcription factor Hac1p (SEQ ID NO: 19) is increased to activate the unfolded protein response to further facilitate protein folding and production. The activity of the transcription factor Hac1p could be increased by overexpression of the endogenous gene encoding Hac1p, such as HAC1 in *S. cerevisiae*.

Thus, in an embodiment, the fungal cell is genetically modified for enhanced expression of at least one transcription factor that controls the expression of chaperone proteins, preferably the at least one transcription factor is selected from a group consisting of Hsf1p and Hac1p.

In a further embodiment, the transport between the endoplasmic reticulum (ER) and the Golgi could be increased. This could be achieved, for example, by overexpression of the endogenous proteins involved in ER-Golgi transport, such as Ypt1p, Bos1p, Bet1p, Sec22p, Sed5p, Sar1p, Sec12p, Sec23p, Sec24p, Sec13p, sec14p, Sec15p, Sec16p, Sec17p, Sec18p, Sec19p, Sec20p, Sec21p, Sec22p, Sec25p, Sec26p, Sec27p, Sec28p, Sec29p, Sec30p, Sec31p, Erv14p, Erv26p, Emp24p, Erv25p and/or Erv29p. For example, any of the endogenous genes encoding for these activities, YPT1, BOS1, BET1, SEC22, SED5, SARI, SEC12, SEC23, SEC24, SEC13, SEC14, SEC15, SEC16, SEC17, SEC18, SEC19, SEC20, SEC21, SEC22, SEC25, SEC26, SEC27, SEC28, SEC29, SEC30, SEC31, ERV14, ERV26, EMP24, ERV25 and ERV29, respectively, could be overexpressed in a *S. cerevisiae* cell. In a preferred embodiment the overexpressed gene is taken from the group of SEC12, SEC13, SEC16 and ERV25.

Thus, in an embodiment, the fungal cell is genetically modified for overexpression of at least one endogenous protein involved in the transport between the endoplasmic reticulum and the Golgi, preferably the at least one endogenous protein is selected from a group consisting of Ypt1p, Bos1p, Bet1p, Sec22p, Sed5p, Sar1p, Sec12p, Sec23p, Sec24p, Sec13p, sec14p, Sec15p, Sec16p, Sec17p, Sec18p, Sec19p, Sec20p, Sec21p, Sec22p, Sec25p, Sec26p, Sec27p, Sec28p, Sec29p, Sec30p, Sec31p, Erv14p, Erv26p, Emp24p, Erv25p and Erv29p.

In another embodiment recombinant protein production in a fungal cell is increased by combining any of the modifications described above or below with increase in the transport between the Golgi and the plasma membrane (PM). This can be achieved by increasing the levels of the vesicle components involved in Golgi-PM transport. For example, the levels of Sec3p, Sec5p, Sec10p, Sec6p, Sec8p, Exo70p, Exo84p, Sso1p, Sec1p, Ypt32p and/or Sec4p could be increased. This could be achieved by overexpression of any of the endogenous genes encoding these activities. For example, the endogenous genes SEC3, SEC5, SEC10, SEC6, SEC8, EXO70, EX084, SSO1, SEC1, EXO70, YPT32 and/or SEC4 could be overexpressed in *S. cerevisiae*.

Thus, in an embodiment, the fungal cell is genetically modified for overexpression of at least one endogenous protein involved in the transport between the Golgi and the plasma membrane, preferably the at least one endogenous protein is selected from a group consisting of Sec3p, Sec5p, Sec10p, Sec6p, Sec8p, Exo70p, Exo84p, Sso1p, Sec1p, Ypt32p and Sec4p.

In some embodiments, the glycosylation of the fungal cell can be modified in order to achieve humanized glycosylation. This can be achieved, for example, by disruption of N-hypermannose glycosylation through disruption of Och1p, Alg3p and/or Mnn9p. For example, the endogenous genes encoding these proteins (OCH1, ALG3, and MNN9, respectively) could be deleted in *S. cerevisiae*.

In another embodiment, recombinant protein production in a fungal cell could be increased by combining any of the modifications described above or below with deletion in the lipid regulator Opi1p. For example, the endogenous gene encoding OPI1 could be deleted in *S. cerevisiae*.

In another embodiment, recombinant protein production in a fungal cell could be increased by combining any of the modifications described above or below with deletion of proteases in order to prevent proteolytic degradation of the target protein. This could include vacuolar proteases. For example, the vacuolar proteases Pep4p and/or Prb1p could be deleted. This could be achieve by deleting the endogenous genes PEP4 and/or PRB1 in *S. cerevisiae*. Alternatively, or in addition, yapsin proteases, which are a family of aspartic proteases located at cell surface could also be disrupted. For example, the yapsin proteases Yps1p, Yps2p, Yps3p, Yps5p, Yps6p and/or Yps7p could be downregulated. This could be achieved by deletion of the endogenous genes YPS1, YPS2, YPS3, YPS5, YPS6 and/or YPS7 in *S. cerevisiae*.

Thus, in an embodiment, the fungal cell lacks genes encoding proteases or comprises disrupted genes encoding endogenous proteases, preferably selected from a group consisting of Pep4p, Prb1p, Yps1p, Yps2p, Yps3p, Yps5p, Yps6p and Yps7p.

In a further embodiment, degradation of non-native proteins can be reduced by deletion or downregulation of the HTM1 gene in *S. cerevisiae*, coding for an alpha-1,2-specific exomannosidase.

In another embodiment, recombinant protein production in a fungal cell could be increased by combining any of the modifications described above or below with increasing the levels of co-translational translocation components. This can be achieved, for example, by overexpression of the endogenous SRP components, such as Srp14p, Srp21p, Srp68p, Srp72p, Sec65p and/or Srp54p. For example, the endogenous genes SRP14, SRP21, SRP68, SRP72, SEC65 and/or SRP54 could be overexpressed in *S. cerevisiae*.

Thus, in an embodiment, the fungal cell is genetically modified for overexpression of at least one endogenous co-translational translocation protein, preferably selected from a group consisting of Srp14p, Srp21p, Srp68p, Srp72p, Sec65p and Srp54p.

In another embodiment, recombinant protein production in a fungal cell could be increased by combining any of the modifications described above or below with modifications in hypoxic gene expression. For example, the endogenous protein Rox1p could be disrupted by deletion of the ROX1 gene (a Heme-dependent repressor of hypoxic genes) in *S. cerevisiae*. Alternatively, activity of the transcription factor Upc2p could be increased. For example, the UPC2-1 allele, which has a G888D mutation in the C-terminus and as a result constitutively activates ergosterol biosynthesis could be overexpressed in *S. cerevisiae*.

In another embodiment, recombinant protein production in a fungal cell could be increased by combining any of the modifications described above or below with reduced endocytosis. This can be achieved by disrupting the endogenous proteins associated with endocytosis, such as Rvs161p and End3p. For example, the endogenous RVS161 and END3 genes could be downregulated in *S. cerevisiae*.

In another embodiment, recombinant protein production in a fungal cell could be increased by combining any of the modifications described above or below with disruption in vacuolar sorting. This could be achieved by disruption of genes involved in vacuolar sorting. For example, Vps30p, Rgp1p, Mrl1p, Vam3p, Vps2p, Vps3p, Vps4p, Vps11p, Vps13p, Vps16p, Vps18p, Vps20p, Vps22p, Vps23p, Vps24p, Vps25p, Vps27p, Vps28p, Vps31p, Vps32p, Vps33p, Vps36p, Vps37p, Vps39p, Vps41p, Vps43p, Vps44p and/or Vps46p.

Thus, in an embodiment, the fungal cell is genetically modified for downregulation of at least one protein involved in vacuolar sorting, preferably selected from a group consisting of Vps30p, Rgp1p, Mrl1p, Vam3p, Vps2p, Vps3p, Vps4p, Vps11p, Vps13p, Vps16p, Vps18p, Vps20p, Vps22p, Vps23p, Vps24p, Vps25p, Vps27p, Vps28p, Vps31p, Vps32p, Vps33p, Vps36p, Vps37p, Vps39p, Vps41p, Vps43p, Vps44p and Vps46p.

In an embodiment, the fungal cell lacks the gene encoding Tda3p or comprises a disrupted endogenous gene encoding Tda3p. The fungal cell is also genetically modified for reduced expression of Vps5p, such as lacks the gene encoding Vps5p or comprises a disrupted endogenous gene encoding Vps5p. The fungal cell further lacks a gene encoding Hda2p or comprises a disrupted endogenous gene encoding Hda2p.

In an embodiment, the fungal cell comprises a heterologous gene encoding the recombinant protein.

The above described embodiments may be combined.

Another aspect of the embodiments relates to a method for producing a recombinant protein. The method comprises culturing a fungal cell according to any of the embodiments in a culture medium and in culture conditions suitable for production of the recombinant protein by the fungal cell. The method also comprises collecting the recombinant protein from the culture medium and/or from the fungal cell.

EXAMPLES

Example 1

Effect of Single Deletions on Protein Production in Yeast

In this example the effect of single gene deletions of ECM3, EMC1, ERV29, GOS1, VPS5, TDA3, COG5, SNC2, HDA2, HDA3, TAN1, PGM2 and PXA1 on recombinant protein production and secretion was examined in a BY4742 *S. cerevisiae* strain.

These single gene deletion strains were purchased from the EUROSCARF and transformed with the α-amylase expression plasmid p426GPD-Amylase. Single gene deletion strains of BY4742 harboring plasmid p426GPD-Amylase were selected on SD-ura plates and then cultured in SD-2×SCAA medium for α-amylase production.

For protein production in tubes or shake flasks, yeast strains were cultured at 30° C. and 200 rpm for 96 hours in the SD-2×SCAA medium[2] containing 20 g/L glucose, 6.9 g/L yeast nitrogen base without amino acids, 190 mg/L Arg, 400 mg/L Asp, 1260 mg/L Glu, 130 mg/L Gly, 140 mg/L His, 290 mg/L Ile, 400 mg/L Leu, 440 mg/L Lys, 108 mg/L Met, 200 mg/L Phe, 220 mg/L Thr, 40 mg/L Trp, 52 mg/L Tyr, 380 mg/L Val, 1 g/L BSA, 5.4 g/L $Na_2HPO_4$, and 8.56 g/L $NaH_2PO_4.H_2O$ (pH=6.0 by NaOH).

The α-amylase activity in culture supernatant was measured using the α-amylase assay kit (Megazyme K-CERA, Ireland) and a commercial α-amylase from *Aspergillus oryzae* (Sigma, USA) was used as a standard. The weight of α-amylase can be calculated with 69.6 U/mg as α-amylase conversion coefficient according to Liu et al (Biotechnol Bioeng. 2012 May; 109(5):1259-68. doi: 10.1002/bit.24409). For intracellular α-amylase measurements, cell pellet was collected from 0.5 ml cell cultures by centrifugation at 12000×g for 3 min. The cell pellet was washed with distilled water and resuspended in 0.5 ml PBS buffer containing 5 µl halt protease inhibitor cocktail (Thermo Fisher, USA). The cell suspension was added to a lysing matrix tube and cell lysis was processed in a FastPrep-24 tissue and cell homogenizer (MP Biomedicals, USA) at a speed of 6.5 m/s for 2 min. Cell debris was removed by centrifugation and the supernatant fraction was used for α-amylase quantification.

Figure 2:
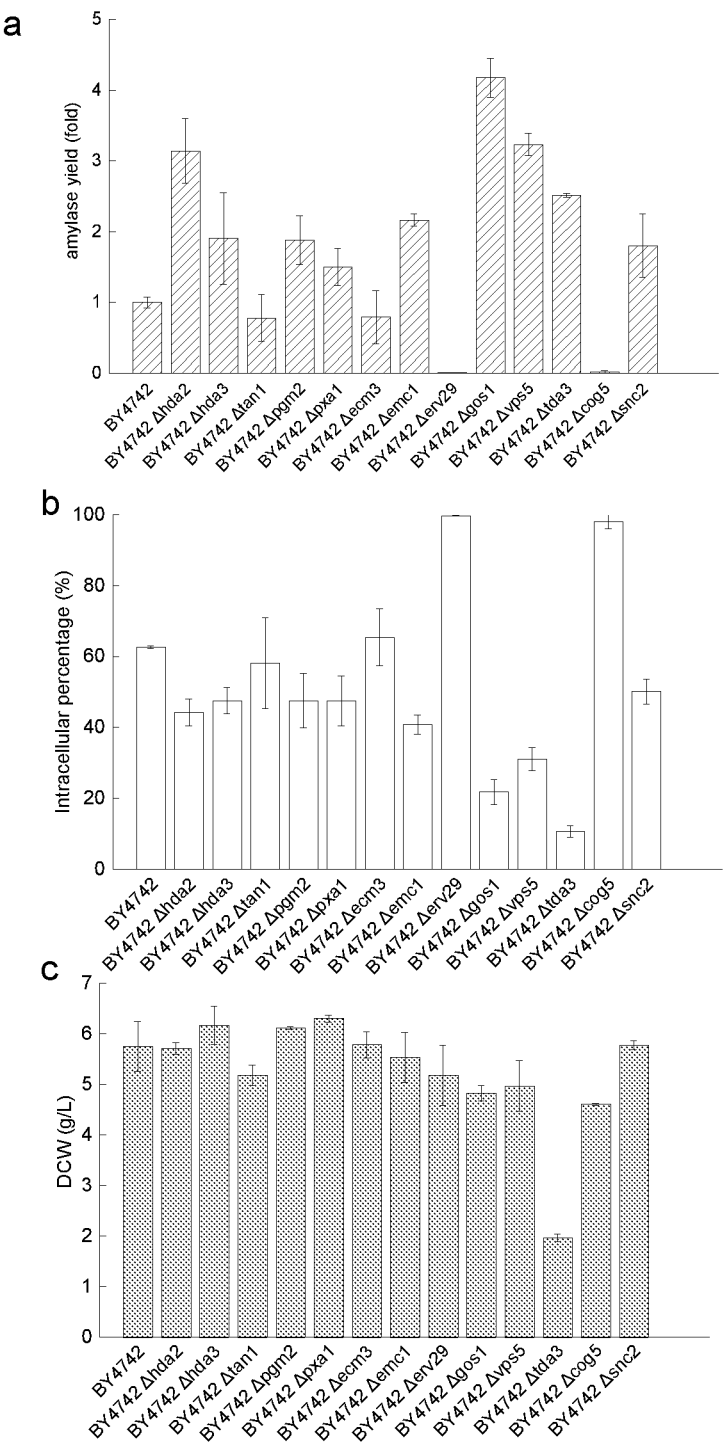
FIG. 2: Disruption of selected genes, especially HDA2, HDA3, PGM2, PXA1, EMC1, GOS1, VPS5, TDA3 or SNC2 in the yeast *Saccharomyces cerevisiae* leads to increase in recombinant protein production. a) Recombinant protein yield. b) Intracellular percentage—the fraction of the protein that is retained in the cell c) Dry cell weight. α-amylase was used as a model protein in this study.

As shown in FIG. 2, amylase production was improved upon disruption of HDA2, HDA3, PGM2, PXA1, EMC1, GOS1, VPS5, TDA3 and SNC2 (FIG. 2a). Moreover, these modifications were generally associated with a decrease in the intracellular percentage of amylase (FIG. 2b), suggesting increased secretion.

Example 2

Combinatorial Effects of the Gene Deletions

The best four gene targets from Example 1 above (HDA2, VPS5, GOS1 and TDA3) were selected for further studies in CEN.PK strain background.

Figure 3:
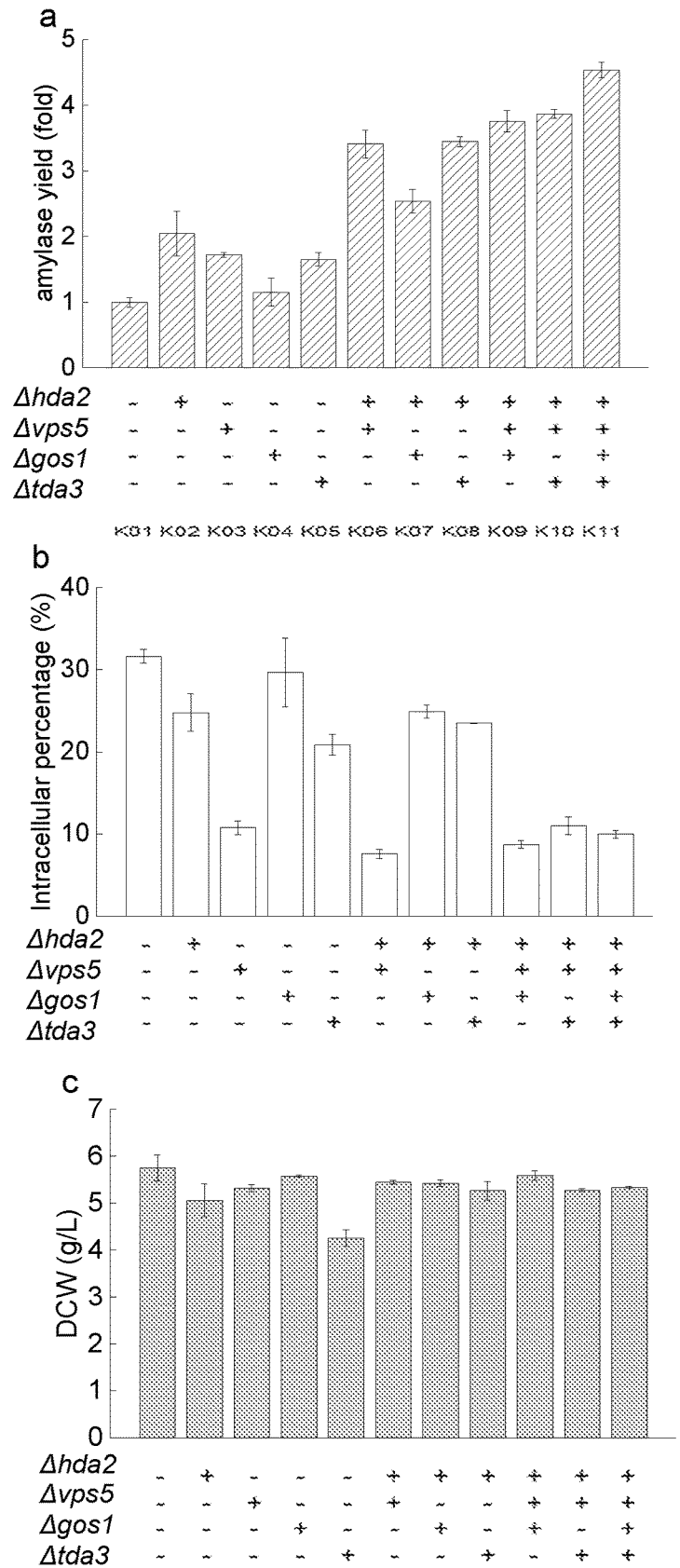
FIG. 3: Combinatorial effect of gene deletions on protein production in yeast. a) Recombinant protein yield. b) Intracellular percentage—the fraction of the protein that is retained in the cell. c) Dry cell weight. α-amylase was used as a model protein in this study.
Figure 4:
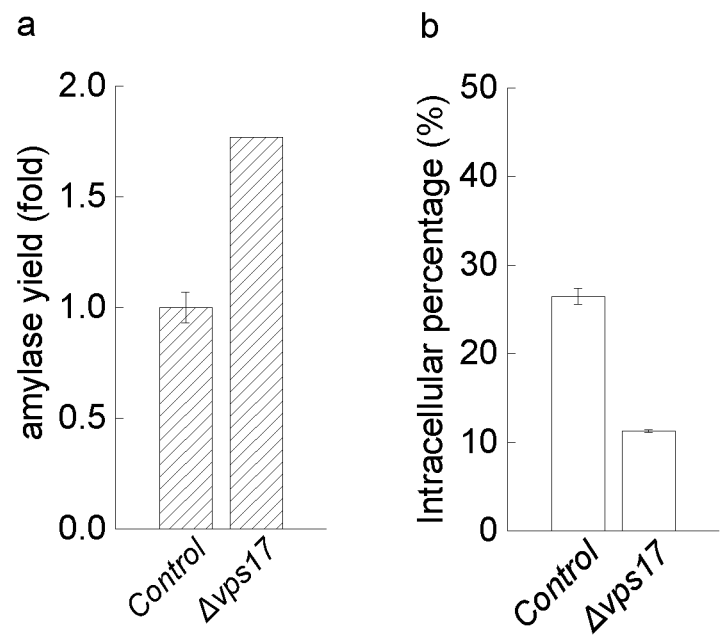
FIG. 4: Disruption of VPS17 increases recombinant protein production a) and decreases intracellular recombinant protein percentage b), suggesting increased secretion. α-amylase was used as a model protein in this study.

Gene deletion in CEN.PK strain was performed by using the amdS gene as selection marker and by following the protocols described by Solis-Escalante et al (FEMS Yeast Res. 2013 February; 13(1):126-39. doi: 10.1111/1567-1364.12024). Primer pairs HDA2F and HDA2R and PrimeSTAR HS DNA polymerase (Takara, Kyoto, Japan) were used to amplify the HDA2 deletion cassette by using the plasmid pUG-amdSYM as template. The HDA2 deletion cassette was transformed into strain K01 for HDA2 deletion using a standard LiAc/SS DNA/PEG method by Gietz et al (Methods Enzymol. 2002 350, 87-96). Colonies grew on the selective SM-Ac plates were verified for correct hda2 deletion by diagnosis primers HDA2P1 and HDA2P2. As the primer HDA2R contains a homologous sequence to the upstream region of HDA2, the amdS marker can be looped out from the chromosome by homologous recombination. Similarly, VPS5, GOS1 and TDA3 deletion cassettes were amplified from the plasmid pUG-amdSYM by using primer pairs VPS4F/VPS5R, GOS1F/GOS1R and TDA3F/TDA3R, respectively. Deletion of VPS5, GOS1 and TDA3 in CEN.PK strain was carried out by transformation of deletion cassettes and selected on SM-Ac plates. Single gene deletion CEN.PK strains were cultured in SD-2×SCAA medium, and amylase secretion was measured as described in Example 1 above. As shown in FIG. 3, in all cases, single gene deletion increased amylase production and secretion. To further enhance amylase production, combinatorial gene deletions was performed. Combinatorial deletions further increased protein secretion, the triple gene deletions strain K10 (Δhda2, Δvps5 and Δtda3) can secrete 4 fold amylase compared with control strains in tube fermentation. It was noticed that deletion of VPS5 significantly reduced intracellular amylase retention, only 10% of amylase retained in strains with VPS5 deletion. As Vps5p formed a retromer subcomplex with Vps17p, we also tested deletion of VPS17 on amylase secretion. Deletion of VPS17 was performed by transformation of the VPS17 deletion cassette, which was amplified from the plasmid pUG-amdSYM by using primer pairs VPS17F/VPS17R. A similar result of amylase production was obtained in the VPS17 deletion strain, not only amylase yield increased, but also the retention of amylase significantly decreased (FIG. 4). This result emphasized the importance of trafficking between Golgi and endosome in protein secretion.

Example 3

Effect of ERV29 and COG5 Overexpression on Protein Production

The effect of overexpression of ERV29 and COG5 on protein secretion was also tested.

Figure 5:
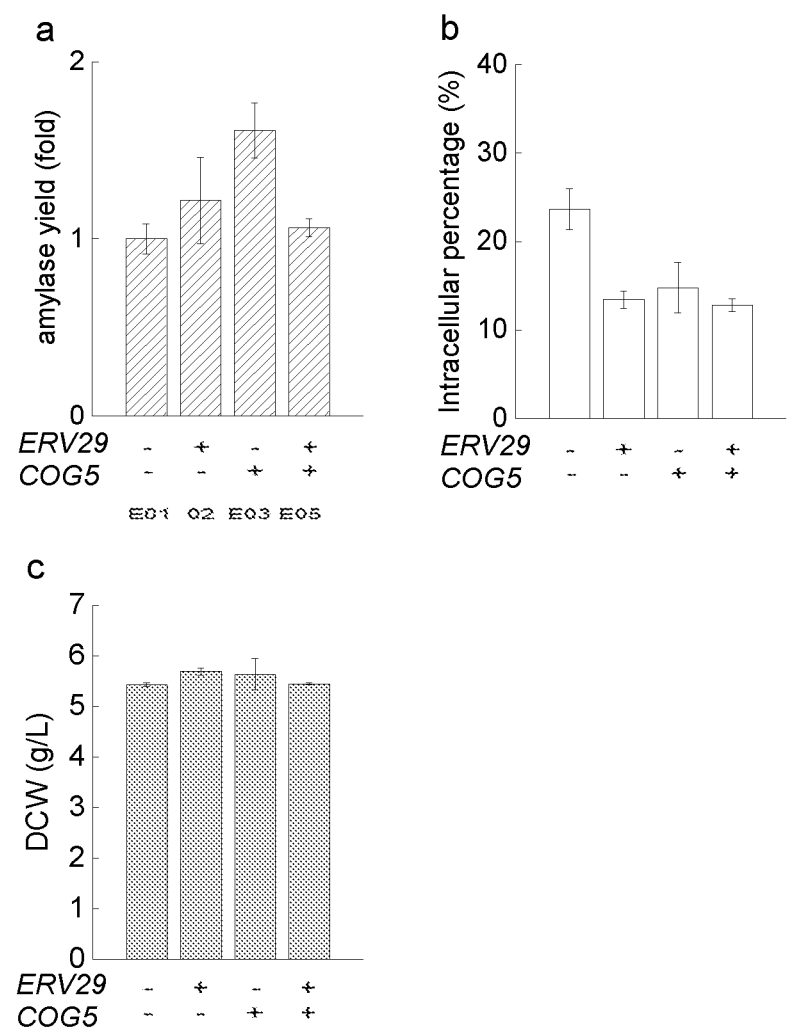
FIG. 5: Effect of ERV29 and/or COG5 overexpression on total protein yield a), intracellular protein percentage b) and dry cell weight c). α-amylase was used as a model protein in this study.

The ERV29 gene fragment was amplified from *S. cerevisiae* CEN.PK 530-1C genome by using primers ERV29EP1 and ERV29EP2, digested with restriction enzymes NotI and SacI, and inserted into the corresponding cloning sites of plasmid pSPGM1, resulting in plasmid pGM-ERV29. The ERV29 gene was under controlled by the promoter TEF1p on the plasmid pGM-ERV29. The COG5 gene fragment was amplified from *S. cerevisiae* CEN.PK 530-1C genome by using primers COG5EP1 and COG5EP2, digested with restriction enzymes BamHI and KpnI, and inserted into the corresponding cloning sites of plasmid pSPGM1, resulting in plasmid pGM-COG5. The COG5 gene was under controlled by the promoter PGK1p on the plasmid pGM-COG5. Similarly, the COG5 gene fragment was inserted into the BamHI-KpnI cloning sites of pGM-ERV29, resulting in the plasmid pGM-ERV-COG, which simultaneously overexpresses both ERV29 and COG5. Together with plasmid pAlphaAmyCPOT, plasmids pGM-ERV29, pGM-COG5 and pGM-ERV-COG were transformed to strain CEN.PK 530.1D as described in Example 1 above, resulting in strain E02, E03 and E05, respectively. Strain E01 with empty plasmid pSPGM1 was used as the reference strain. All strains were cultivated and analyzed for amylase production as described in Example 1 above. As shown in FIG. 5, single gene overexpression improved amylase secretion and decreased intracellular amylase retention. In contrast, combinatorial overexpression only decreased intracellular amylase retention but no increase in amylase secretion. The reason for no increase amylase secretion in combinatorial overexpression strain was most likely that overexpression of two genes by a high copy number plasmid increased burden of cells and consumed too much resource, which should be used for target protein.

Example 4

Combination of Gene Deletion and Gene Overexpression on Protein Production

To reduce cell burden and increase cell stability, strong promoter replacement was applied for overexpression of target genes. Promoter replacement was performed on the triple gene deletions strain K30 (deletion of HDA2, VPS5 and TDA3). The amdS-TEF1p cassette for replacement of the native ERV29 promoter was constructed as follows. Primers ERVPR1 and amdSR1 were used to amplify amdS marker by using plasmid pUG-amdSYM as template. Primers ERVPR3 and ERVPR4 were used to amplify the TEF1p fragment by using plasmid pGM-ERV29 as template. The amdS marker and TEF1p fragment were fused together by fusion PCR and resulted in amdS-TEF1p cassette. The 5' of amdS-TEF1p cassette is homologous to the upstream of the native ERV29 promoter and the 3' of amdS-TEF1p cassette is homologous to the downstream of the native ERV29 promoter. Replacement of the native ERV29 promoter by the promoter TEF1p was accomplished by transformation of the amdS-TEF1p cassette to strain K30 and selected on SM-Ac plates. Primers ERV29P2 and ERVPR5 were used for verification of ERV29 promoter replacement. Similarly, the amdS-PGK1p cassette for replacement of the native COG5 promoter was constructed by using primer pairs COGPR1/amdSR1 and COGPR3/COGPR4, and plasmid pUG-amdSYM and pGM-COG5 as template, respectively. Replacement of the native COG5 promoter by the promoter PGK1p was accomplished by transformation of the amdS-PGK1p cassette to strain K30 and selected on SM-Ac plates, resulting in strain K13. Primers COG5P2 and COGPR5 were used for verification of COG5 promoter replacement.

We were also interested in whether overexpression of PDI1 is compatible with other gene target modifications and further increases protein production capacity of engineered strains. Therefore, both promoter replacement and gene integration were tested for the PDI1 gene. The native PDI1 promoter was replaced by a strong promoter FBA1p. The amdS-FBA1p cassette for replacement of the native PDI1 promoter was constructed as follows. 'Primers PDIFPR1 and amdSR1 were used to amplify amdS marker by using plasmid pUG-amdSYM as template. Primers PDIFPR3 and PDIFPR4 were used to amplify the FBA1p fragment by using *S. cerevisiae* CEN.PK 530-1C genome as template. The amdS marker and FBA1p fragment were fused together by fusion PCR and resulted in amdS-FBA1p cassette. As deletion of GOS1 showed positive on protein secretion, the position for integration of one copy of PDI1 gene was chosen in the GOS1 locus. Hence, integration of PDI1 was accomplished with replacement of GOS1. Two different PDI1 integration cassettes were tested. One was under controlled by the PDI1 native promoter PDI1p. Another one was under controlled by the promoter TEF1p. The amdS-PDI1p-PDI1 cassette for integration of PDI1 under control by the promoter PDI1p was constructed as follows. Primers GOSPDI1 and amdSR1 were used to amplified amdS marker by using plasmid pUG-amdSYM as template. Primers GOSPDI3 and GOSPDI4 were used to amplify the PDI1p-PDI1 fragment by using *S. cerevisiae* CEN.PK 530-1C genome as template. The amdS marker and PDI1p-PDI1 fragment were fused together by fusion PCR and resulted in amdS-PDI1p-PDI1 replacement cassette. The amdS-TEF1p-PDI1 cassette was constructed as follows. Primers NGOSPDI1 and amdSR1 were used to amplified amdS marker by using plasmid pUG-amdSYM as template. PDI1 gene fragment was amplified from S. cerevisiae CEN.PK 530-1C genome by using primers PDI1EP1 and PDI1EP2. The PDI1 gene fragment was then digested by NotI and SacI to insert after TEF1p on plasmid pSPGM1, resulting in pGM-PDI1. Primers NGOSPDI3 and NGOSPDI4 were used to amplify the TEF1p-PDI1 fragment by using pGM-PDI1 as template. The amdS marker and TEF1p-PDI1 fragment were fused together by fusion PCR and resulted in amdS-TEF1p-PDI1 replacement cassette. The amdS-FBA1p, amdS-PDI1p-PDI1 and amdS-TEF1p-PDI1 cassettes were transformed to yeast strain K40 for PDI1 promoter replacement or PDI1 integration, resulted in strain K15, K16 and K17, respectively. All transportations, cultivations and amylase measurements were carried out as described in Example 1.

Figure 6:
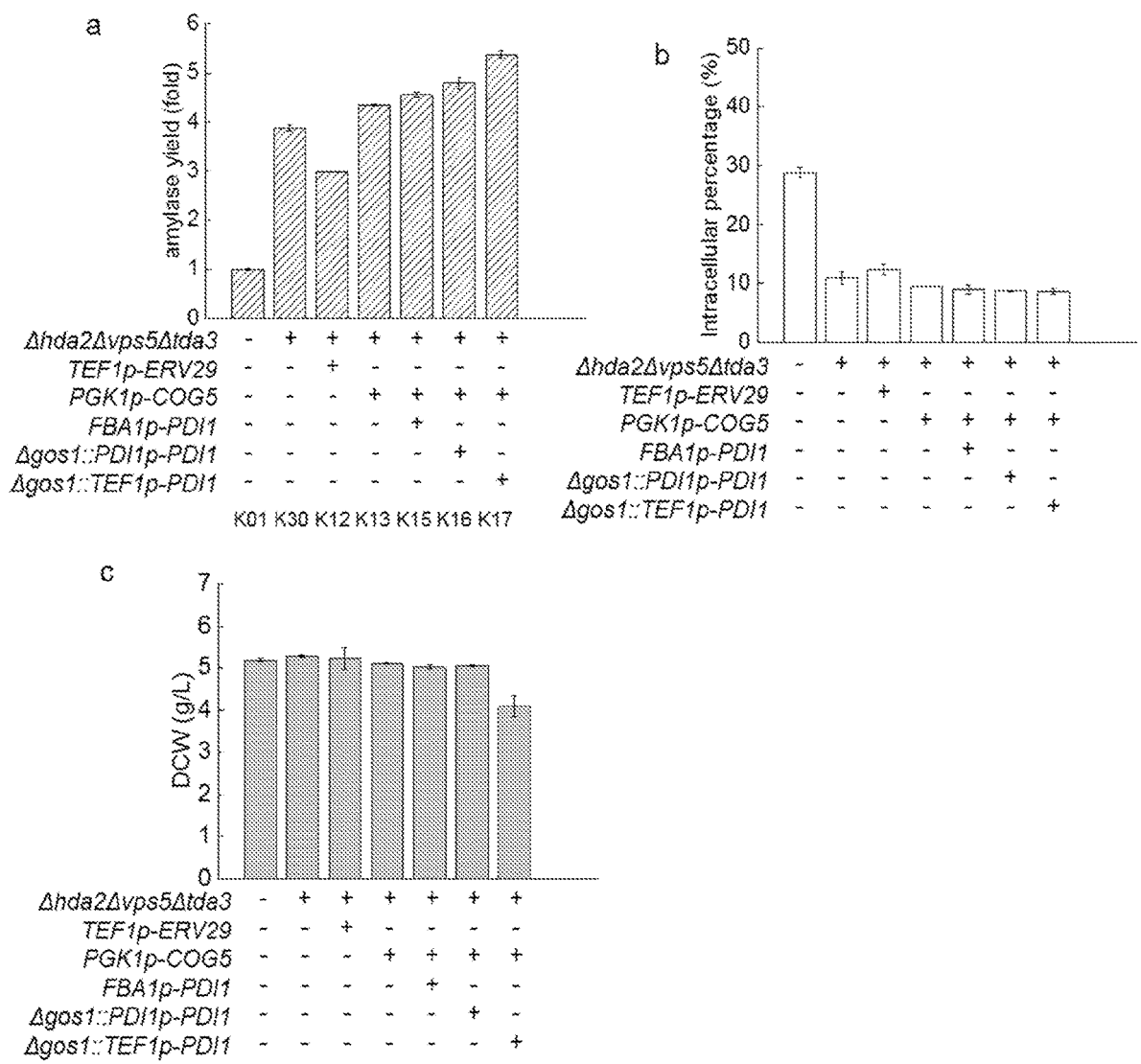
FIG. 6: Combination of selected gene disruption and overexpression increases protein production. a) Total protein yield. b) Intracellular protein percentage. c) Dry cell weight. α-amylase was used as a model protein in this study. The figure shows that combination of deletions of HDA2, VPS5, GOS1 and TDA3 with overexpression of COG5 and PDI1 results in increased α-amylase protein production and decreased intracellular α-amylase percentage, suggesting increased secretion.

As shown in FIG. 6, overexpression of PDI1 was compatible with other gene modifications in yeast strains for enhancement of amylase secretion.

Example 4

Testing of Key Modifications with Other Proteins

In order to demonstrate that the modifications described herein are beneficial for different proteins, the best-producing strain was also tested with glucan 1,4-α-glucosidase instead of amylase. The amylase expression plasmid pAlphaAmyCPOT was eliminated from the best engineered strain K17 by serially transferring into non-selection YPE medium. Strain K17 without plasmid pAlphaAmyCPOT was renamed as CEN.PK 530-1CK303. Another plasmid pCP-aGLA, which expresses the glucan 1,4-α-glucosidase, was transformed into CEN.PK 530-1CK303, and colonies were selected on YPD plates. Then strain CEN.PK 530-1CK303 harboring plasmid pCP-aGLA was cultured in SD-2×SCAA medium and the glucan 1,4-α-glucosidase was measured by using Amyloglucosidase Assay Reagent (Megazyme, Ireland).

Figure 7:
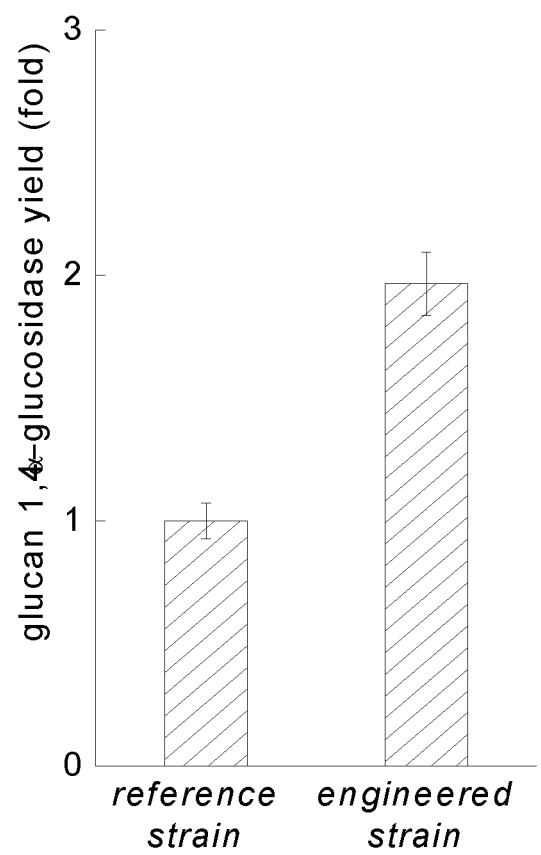
FIG. 7: Combination of selected modifications with additional recombinant proteins. This example shows that the best-producing strain (containing deletions in HDA2, VPS5, GOS1 and TDA3 and overexpression of COG5 and PDI1) can also be used for increased production of glucan 1,4-α-glucosidase.

As shown in FIG. 7, compared with the reference strain, higher glucan 1,4-α-glucosidase yield was achieved by the engineered strain. This result supported that identified gene targets have a general positive effect on protein production, and can be widely used in construction of cell factories for protein production.

Example 5

Fed-Batch Fermentation and Fed-Batch Fermentation

Figure 8:
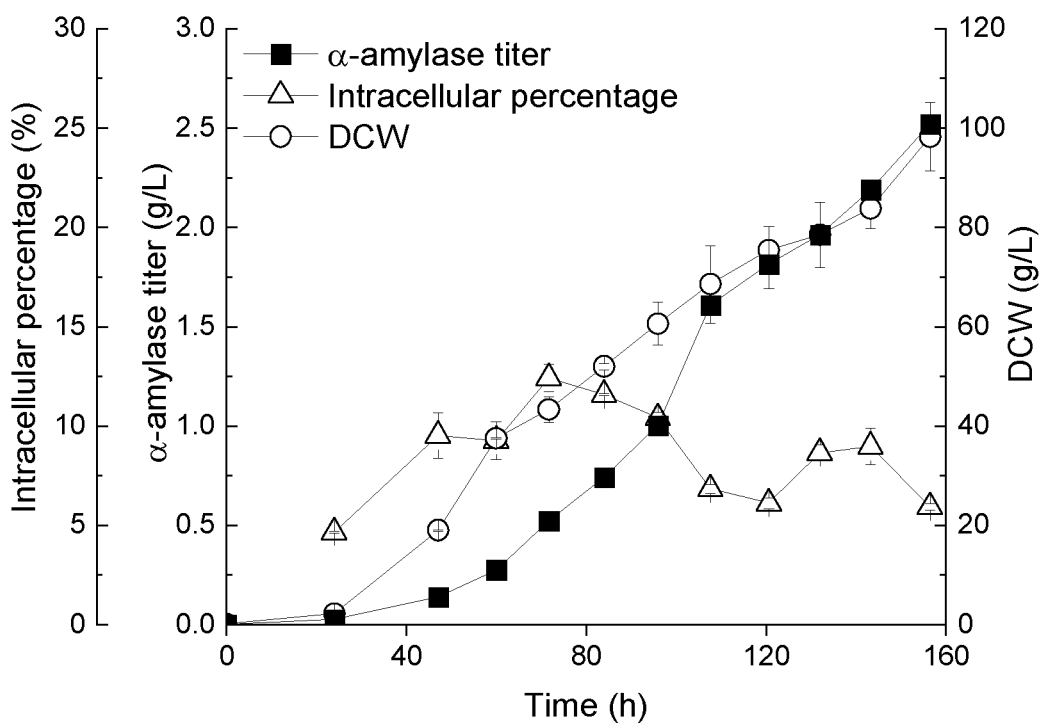
FIG. 8: Fed-batch fermentation of the best-producing strain containing deletions in HDA2, VPS5, GOS1 and TDA3 and overexpression of COG5 and PDI1. α-amylase was used as a model protein in this study.

For the fed-batch cultivation, seed cultures of strain K17 was first inoculated to 200 ml SD-2×SCAA medium (5.4 g/L Na$_2$HPO$_4$ and 8.56 g/L NaH$_2$PO$_4$.H$_2$O were replaced by 2 g/L KH$_2$PO$_4$) with an initial OD$_{600}$ of 0.1. The bioreactor system was run at 30° C., 600 rpm as initial agitation speed and increased to maximally 1200 rpm, 18 L/h as initial air flow and increased to maximally 48 L/h, pH=6 (maintained by using 4 M KOH and 2 M HCl), the dissolved oxygen level was maintained above 30% by controlling agitation speed, air flow and medium feeding. Low glucose 10× feed medium contained: 200 g/L glucose, 69 g/L yeast nitrogen base without amino acids, 50 g/L casamino acids (Formedium, Norfolk, UK), 1 g/L BSA, 20 g/L KH$_2$PO$_4$ (pH=5 by KOH). For the high glucose 10× feed medium, 200 g/L glucose in low glucose 10× feed medium was replaced by 600 g/L glucose. After the glucose and ethanol were consumed in batch culture (200 ml SD-2×SCAA medium), the exponential feed was started by using the low glucose 10× feed medium and controlled at a specific growth rate of 0.08 h$^{-1}$. When both the agitation speed and the air flow reached maximum value (1200 rpm and 48 L/h, respectively), medium feeding was triggered by dissolved oxygen level >30%. After feeding about 330 ml of low glucose 10× feed medium, high glucose 10× feed medium was used. And fermentation was stopped when 330 ml of high glucose 10× feed medium was fed in the bioreactor. Totally, 660 ml of feeding medium was added to the bioreactor. Biological duplicate experiments were conducted in fed-batch cultivation. As shown in FIG. 8, the final α-amylase titer reached 2.5 g/L, and intracellular α-amylase retention maintained a low level (most of the time below 10% and peak value was 12%) in the whole process.

Both batch and fed-batch cultivation results confirmed that the protein secretion was substantially improved in yeast strain with combinatorial modifications. The engineered strain was able to adapt high density fermentation and showed potential industrial application.

TABLE 1

| Plasmids and strains | | |
|---|---|---|
| Plasmids and strains | Relevant genotype | Reference |
| Plasmids | | |
| CPOTud | 2 μm, AmpR, TPI1p, TPI1t, POT1 gene from S. pombe as a selection marker. | Biotechnol. Bioeng. 109, 1259-1268 (2012) |
| pAlphaAmyCPOT | CPOTud-(TPI1p-alpha factor leader-amylase gene-TPI1t) | Biotechnol. Bioeng. 109, 1259-1268 (2012) |
| p426GPD | 2 μm, AmpR, URA3, GPDp, CYC1t | Gene 156,119-122 (1995). |
| p426GPD-Amylase | P426GPD-(GPDp-alpha factor leader-amylase gene-CYC1t) | FEMS Yeast Res. 15, fov070 (2015). |
| pSPGM1 | 2 μm, AmpR, URA3, TEF1p, ADH1t, PGK1p, CYC1t | FEMS Yeast Res. 12, 598-607 (2012). |
| pGM-ERV29 | pSPGM1-(TEF1p-ERV29-ADH1t) | This study |
| pGM-COG5 | pSPGM1-(PGK1p-COG5-CYC1t) | This study |
| pGM-ERV-COG | pSPGM1-(TEF1p-ERV29-ADH1t) + (PGK1p-COG5-CYC1t) | This study |

TABLE 1-continued

| Plasmids and strains | | |
|---|---|---|
| Plasmids and strains | Relevant genotype | Reference |
| pGM-PDI1 | pSPGM1-(TEF1p-PDI1-ADH1t) | This study |
| pCP-aGLA | CPOTud-(TPI1p-alpha factor leader-glucan 1,4-a-glucosidase gene-TPI1t) | Proc. Natl Acad. Sci. USA 112, E4689-E4696 (2015). |
| pUG-amdSYM | AmpR, TEF2p-amdS-TEF2t | FEMS Yeast Res. 13, 126-139 (2013). |
| Strains | | |
| BY4742 | MATα his3Δ1 leu2Δ0 lys2Δ0 ura3Δ0 | EUROSCARF |
| BY4742 Δhda2 | BY4742 Δhda2::kanMX4 | EUROSCARF |
| BY4742 Δhda3 | BY4742 Δhda3::kanMX4 | EUROSCARF |
| BY4742 Δtan1 | BY4742 Δtan1::kanMX4 | EUROSCARF |
| BY4742 Δpgm2 | BY4742 Δpgm2::kanMX4 | EUROSCARF |
| BY4742 Δpxa1 | BY4742 Δpxa1::kanMX4 | EUROSCARF |
| BY4742 Δecm3 | BY4742 Δecm3::kanMX4 | EUROSCARF |
| BY4742 Δemc1 | BY4742 Δemc1::kanMX4 | EUROSCARF |
| BY4742 Δerv29 | BY4742 Δerv29::kanMX4 | EUROSCARF |
| BY4742 Δgos1 | BY4742 Δgos1::kanMX4 | EUROSCARF |
| BY4742 Δvps5 | BY4742 Δvps5::kanMX4 | EUROSCARF |
| BY4742 Δtda3 | BY4742 Δtda3::kanMX4 | EUROSCARF |
| BY4742 Δcog5 | BY4742 Δcog5::kanMX4 | EUROSCARF |
| BY4742 Δsnc2 | BY4742 Δsnc2::kanMX4 | EUROSCARF |
| CEN.PK 530-1C | MATa URA3 HIS3 LEU2 TRP1 SUC2 MAL2-8$^c$ tpi1(41-707)::loxP-kanMX-loxP | Biotechnol. Bioeng. 109, 1259-1268 (2012) |
| CEN.PK 530-1CK | MATa URA3 HIS3 LEU2 TRP1 SUC2 MAL2-8$^c$ tpi1(41-707)::loxP | This study |
| CEN.PK 530-1CK303 | CEN.PK 530-1CK Δhda2 Δvps5 Δtda3 PGK1p-COG5 Δgos1::amdSYM-TEF1p-PDI1 | This study |
| CEN.PK 530-1D | MATa HIS3 LEU2 TRP1 SUC2 MAL2-8$^c$ ura3-52 tpi1(41-707)::loxP-KanMX4-loxP | Metab. Eng. 14, 120-127 (2012). |
| K01 | CEN.PK 530-1CK/pAlphaAmyCPOT | This study |
| K02 | CEN.PK 530-1CK Δhda2::amdSYM/ pAlphaAmyCPOT | This study |
| K03 | CEN.PK 530-1CK Δvps5::amdSYM/ pAlphaAmyCPOT | This study |
| K04 | CEN.PK 530-1CK Δgos1::amdSYM/ pAlphaAmyCPOT | This study |
| K05 | CEN.PK 530-1CK Δtda3::amdSYM/ pAlphaAmyCPOT | This study |
| K06 | CEN.PK 530-1CK Δhda2 Δvps5::amdSYM/ pAlphaAmyCPOT | This study |
| K07 | CEN.PK 530-1CK Δhda2 Δgos1::amdSYM/ pAlphaAmyCPOT | This study |
| K08 | CEN.PK 530-1CK Δhda2 Δtda3::amdSYM/ pAlphaAmyCPOT | This study |
| K09 | CEN.PK 530-1CK Δhda2 Δvps5 Δgos1::amdSYM/ pAlphaAmyCPOT | This study |
| K10 | CEN.PK 530-1CK Δhda2 Δvps5 Δtda3::amdSYM/ pAlphaAmyCPOT | This study |
| K30 | CEN.PK 530-1CK Δhda2 Δvps5 Δtda3/ pAlphaAmyCPOT | This study |
| K11 | CEN.PK 530-1CK Δhda2 Δvps5 Δtda3 Δgos1::amdSYM/pAlphaAmyCPOT | This study |
| K12 | CEN.PK 530-1CK Δhda2 Δvps5 Δtda3 amdSYM-TEF1p-ERV29/pAlphaAmyCPOT | This study |
| K13 | CEN.PK 530-1CK Δhda2 Δvps5 Δtda3 amdSYM-PGK1p-COG5/pAlphaAmyCPOT | This study |
| K40 | CEN.PK 530-1CK Δhda2 Δvps5 Δtda3 PGK1p-COG5/ pAlphaAmyCPOT | This study |
| K15 | CEN.PK 530-1CK Δhda2 Δvps5 Δtda3 PGK1p-COG5 amdSYM-FBA1p-PDI1/pAlphaAmyCPOT | This study |
| K16 | CEN.PK 530-1CK Δhda2 Δvps5 Δtda3 PGK1p-COG5 Δgos1::amdSYM-PDI1p-PDI1/pAlphaAmyCPOT | This study |
| K17 | CEN.PK 530-1CK Δhda2 Δvps5 Δtda3 PGK1p-COG5 Δgos1::amdSYM-TEF1p-PDI1/pAlphaAmyCPOT | This study |
| E01 | CEN.PK 530-1D/pAlphaAmyCPOT + pSPGMI | This study |
| E02 | CEN.PK 530-1D/pAlphaAmyCPOT + pGM-ERV29 | This study |
| E03 | CEN.PK 530-1D/pAlphaAmyCPOT + pGM-COG5 | This study |
| E05 | CEN.PK 530-1D/pAlphaAmyCPOT + pGM-ERV-COG | This study |
| E13 | CEN.PK 530-1CK/pCP-aGLA | This study |
| E14 | CEN.PK 530-1CK303/pCP-aGLA | This study |

TABLE 2

Primers

| Name | SEQ ID NO | Sequence (5'→3')# |
|---|---|---|
| | | Plasmid construction |
| ERV29EP1 | 20 | ACTGCGGCCGCAACAAAATGTCTTACAGAGGACCTATTGGA |
| ERV29EP2 | 21 | CGTGAGCTCCTAGTAAATCTTCTTCTTTTCATCAACGGAT |
| COG5EP1 | 22 | TCAGGATCCAACAAAATGACAATAGCGCCAATGGCAA |
| COG5EP2 | 23 | CCAGGTACCTCACTTATTTAGAGAAATAGATACTGAGTTTAGCAT |
| PDI1EP1 | 24 | ACTGCGGCCGCAACAAAATGAAGTTTTCTGCTGGTGCC |
| PDI1EP2 | 25 | CGTGAGCTCTTACAATTCATCGTGAATGGCATCTTCT |
| | | Gene deletion, gene replacement and promoter replacement |
| HDA2F | 26 | ATGAGTAGGAAAAATTCTAAGAAACTAAAAGTCTATTACTTACCT GTAACGCTAACCCAAGACATG GAGGCCCAGA ATAC |
| HDA2R | 27 | AAATCTCTCTATATTATACAGGCTACTTCTTTTAGGAAACGTCAC ATTCATTAGTCGATAGTATTGTATCTATTTTCTTTATTTTCACAC ACCAGTATAGCG ACCAGCATTC |
| VPS5F | 28 | ATGGACTACGAGGATAATCTAGAAGCACCTGTTTGGGACGAACT AAATCATGAGGGAGATAAAGACATG GAGGCCCAGA ATAC |
| VPS5R | 29 | ATAAATCCTGAGGAACGTGACACATAAAGTTATTGTATACAGAT CATCTATTAGGCTTGTTATTGCAGGATGTATGAAAGTTTATAAAA TCCCCAGTATAGCG ACCAGCATTC |
| GOS1F | 30 | ATGAGCTCACAACCGTCTTTCGTCACCATAAGGGGCAAGGCCA TTTCTCTAGAAACACAAACGGGACATG GAGGCCCAGA ATAC |
| GOS1R | 31 | AGATTCTTGTTATGTTTTTACATACGTTGTTTAATAAAAGTCGTTA TTTATCAGTGGTGTGGTTGCTTGTCTGGAATTGGGCTTTTCCCT GTGCAGTATAGCG ACCAGCATTC |
| TDA3F | 32 | ATGGGTGAAGATTTTATGCACCCACCGTTTCAAACGTACCCTTC AAAGAACAGCGAAGGGAAGACATG GAGGCCCAGA ATAC |
| TDA3R | 33 | CAAATTTGTGCATATACTTTTCTTGACCTTATTACTCCTCGGCTT GATTATCATTATAAACACTATTCCTTCTGTTGCTTGGTTAAAATG CTACAGTATAGCG ACCAGCATTC |
| VPS17F | 34 | ATGACTTCGGCTGTACCTTATGATCCATATGATGATCTGGATAA CAATCCATTTGCTGAGCCCCAGGAGGAAGACATGGAGGCCCAG AATAC |
| VPS17R | 35 | AAAGATCACCTTGTTCAAAGGTATGAATTTTCTACTTTATATACG TATTATCATGTTCAGAGGATAGATGGATTGACTAAGGGTACAGT ACGGCAAACAGTATAGCGACCAGCATTC |
| amdSF1 | 36 | GACATG GAGGCCCAGA ATAC |
| amdSR1 | 37 | CAGTATAGCG ACCAGCATTC |
| ERVPR1 | 38 | TTCTAGAAGATGAGAGAAGAGGGAATAATGAGAAAGGCGAAAA ATAAAGGCACACACCCATAGCTTCAAAATGTTTCTACTCCTTTTTT ACTCTTCCAGACATG GAGGCCCAGA ATAC |
| ERVPR3 | 39 | AAGTTAAGTGCGCAGAAAGTAATATCATGCGTCAATCGTATGTG AATGCTGGTCGCTATACTGGCACACACCATAGCTTCAAAATGT |
| ERVPR4 | 40 | GACAAACTTGGAATGTAAGGCTTC |
| COGPR1 | 41 | ATTTTTTGTTAGACATATAATTTTATATCATTATTCTTATTATTCTT ATAGGAAGTACCTTCAAAGAATGGGGTCTTATCTTGTTTTGCAA GTACCACGACATG GAGGCCCAGA ATAC |
| COGPR3 | 42 | AAGTTAAGTGCGCAGAAAGTAATATCATGCGTCAATCGTATGTG AATGCTGGTCGCTATACTGGGAAGTACCTTCAAAGAATGGGGTC |
| COGPR4 | 43 | TATCTCCAATGGGTTGCTATTCATC |

TABLE 2-continued

Primers

| Name | SEQ ID NO | Sequence (5'→3')# |
|---|---|---|
| PDIFPR1 | 44 | GCATTTTGTTGTGCTGTTACAACCACAACAAAACGAAAAACCCG TATGGATCCAACTGGCACCGCTGGCTTGAACAACAATACCAGC CTTCCAACTTCGACATG GAGGCCCAGA ATAC |
| PDIFPR3 | 45 | AAGTTAAGTGCGCAGAAAGTAATATCATGCGTCAATCGTATGTG AATGCTGGTCGCTATACTGTCCAACTGGCACCGCTGGCTT |
| PDIFPR4 | 46 | ACAGCCTCTTGTTGGGCGAAAACAGAGGAGGCGAGCAGCAGG GAGGACCATGACAGGACGGCACCAGCAGAAAACTTCATTTTGA ATATGTATTACTTGGTTATGGTTATATATGAC |
| GOSPDI1 | 47 | GTTCAATAGTGTGGTTGGTAACCAAATTTTCTAGGCGTTGTTGA AAATAATCATTAGTGCCCACCGTTTGAGCGTGGTGTGACACCAC GCCCAAGATAGACATGGAGGCCCAGA ATAC |
| GOSPDI3 | 48 | CCCAGATGCGAAGTTAAGTGCGCAGAAAGTAATATCATGCGTCA ATCGTATGTGAATGCTGGTCGCTATACTGTCATTAGTGCCCACC GTTTGAG |
| GOSPDI4 | 49 | ATTACGAAATGGCCTGTATGGGTAGATTCTTGTTATGTTTTTACA TACGTTGTTTAATAAAAGTCGTTATTCAATTACAATTCATCGTGA ATGGCATCT |
| GOSPDI5 | 50 | CCCAGATGCGAAGTTAAGTGC |
| GOSPDI6 | 51 | ATTACGAAATGGCCTGTATGGGTAG |
| NGOSPDI1 | 52 | TACTCTTGTTCAATCAGTTAGTTATCTTTGTTCAATAGTGTGGTT GGTAAGCACACACCATAGCTTCAAAATGTTTCTACTCCTTTTTTA CTCTTCCAGACATGGAGGCCCAGA ATAC |
| NGOSPDI3 | 53 | CCCAGATGCGAAGTTAAGTGCGCAGAAAGTAATATCATGCGTCA ATCGTATGTGAATGCTGGTCGCTATACTGGCACACACCATAGCT TCAAAATGT |
| NGOSPDI4 | 54 | ATTACGAAATGGCCTGTATGGGTAGATTCTTGTTATGTTTTTACA TACGTTGTTTAATAAAAGTCGTTATTCATTACAATTCATCGTGAA TGGCATCTTC |
| Verification primers for gene deletion, gene replacement and promoter replacement | | |
| amdSP1 | 55 | TTACCACGGTGCTCCAGTTG |
| amdSP2 | 56 | AACCAAGTCAGCAGCAGAAG |
| HDA2P1 | 57 | TGCGGCACAGAAGAGTAACC |
| HDA2P2 | 58 | GGCGATAAACGATAGGCAAC |
| VPS5P1 | 59 | TCCGCTAAGAACAACTAAGTGA |
| VPS5P2 | 60 | CACTGGCTGTAAACGGACCTAT |
| GOS1P1 | 61 | TGCAAACCCAGTGTAAGACGC |
| GOS1P2 | 62 | ATATGGTTCGAGAACAGGCATC |
| TDA3P1 | 63 | AGCACGACATAGAAGTGAAACC |
| TDA3P2 | 64 | CGCAAGGGCAAACAGGATAGAC |
| VPS17P1 | 65 | CGATTGAGTCGAACACCCTGA |
| VPS17P2 | 66 | CTTGGGTGCGTAGGTCTGG |
| ERV29P2 | 67 | GTCTTGTAACCAATGGCGAAAC |
| ERVPR5 | 68 | GCCACCACGATTGACGAACA |
| COG5P2 | 69 | TTAACAGCGACTTGCCCACAGG |
| COGPR5 | 70 | AGCTAGTCTGTGACCTGTACG |
| PDIPR5 | 71 | TGCACGTGATAATATGTTACCCTGTC |

TABLE 2-continued

Primers

| Name | SEQ ID NO | Sequence (5'→3')# |
|---|---|---|
| PDIPR6 | 72 | GGAGGAGGATGAGATAAGTAGTTTCC |
| GOS1P5 | 73 | AAAACTCTGGCGGCTAAACTGG |
| GOS1P6 | 74 | CATCAATACTGGCGATAAGCGGGAC |
| PDI7 | 75 | TCCTTGGACTCTTTATTCGACTTCATC |
| PDI8 | 76 | CGCATTATAAGTGGTGTGCCGA |
| PDI10 | 77 | ATGCTGTGCTTGGGTGTTTTGA | underlined sequence indicates restriction site.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A fungal cell, wherein
said fungal cell comprises a disrupted endogenous gene encoding Tda3p or an endogenous Tda3p gene that is deleted; is genetically modified for reduced expression of at least one protein selected from a group consisting of Vps5p, Vps17p, Vps29p, Pep8p, and Vps35p, or any combination thereof, and comprises a gene encoding a recombinant protein,
wherein the fungal cell is *Saccharomyces cerevisiae, Pichia pastoris, Ashbya gossypii, Saccharomyces boulardii, Zygosaccharomyces bailii, Kluyveromyces lactis, Rhodosporidium toruloides* or *Yarrowia lipolytica.*

2. The fungal cell according to claim 1, wherein said fungal cell comprises a heterologous gene encoding said recombinant protein.

3. A method for producing a recombinant protein comprising:
culturing a fungal cell according to claim 1 in a culture medium and in culture conditions suitable for production of said recombinant protein by said fungal cell; and
collecting said recombinant protein from said culture medium and/or from said fungal cell.

4. The fungal cell of claim 1, wherein said fungal cell is a *Saccharomyces cerevisiae* cell, which is genetically modified for reduced expression of at least one protein selected from a group consisting of Vps5p (SEQ ID NO: 3), Vps17p (SEQ ID NO: 4), Vps29p (SEQ ID NO: 6), Pep8p (SEQ ID NO: 5), and Vps35p (SEQ ID NO: 7), and variants thereof having at least 80% homology to any of SEQ ID NO: 3-7.

5. The fungal cell of claim 4, wherein the *Saccharomyces cerevisiae* cell comprises a heterologous gene encoding said recombinant protein.

\* \* \* \* \*

UNITED STATES PATENT AND TRADEMARK OFFICE
CERTIFICATE OF CORRECTION

PATENT NO. : 11,795,487 B2
APPLICATION NO. : 16/634267
DATED : October 24, 2023
INVENTOR(S) : Huang et al.

It is certified that error appears in the above-identified patent and that said Letters Patent is hereby corrected as shown below:

On the Title Page

(71) Applicant: Please correct "Melt & Marble AB" to read --Melt&Marble AB--

In the Specification

Column 13, Line 11: Please correct "ncbi.nlm.nih.gov/Blast.cgi" to read --blast.ncbi.nlm.nih.gov/Blast.cgi--

Column 17, Line 23: Please correct "(R2065)" to read --(R206S)--

Column 17, Line 47: Please correct "SARI" to read --SAR1--

Column 21, Line 1: Please correct "VPS4F/VPS5R" to read --VPS5F/VPS5R--

Column 25, Line 7, TABLE 1-continued: Please correct "*1,4-a-glucosidase gene-TPI1*t)" to read --*1,4-α-glucosidase gene-TPI1*t)--

Signed and Sealed this
Sixth Day of February, 2024

Katherine Kelly Vidal
*Director of the United States Patent and Trademark Office*

SEQUENCE LISTING

<160> NUMBER OF SEQ ID NOS: 77

<210> SEQ ID NO 1
<211> LENGTH: 523
<212> TYPE: PRT
<213> ORGANISM: Saccharomyces cerevisiae

<400> SEQUENCE: 1

Met Gly Glu Asp Phe Met His Pro Pro Phe Gln Thr Tyr Pro Ser Lys
1               5                   10                  15

Asn Ser Glu Gly Lys Lys His Ile Val Ile Val Gly Gly Gly Ile Ile
                20                  25                  30

Gly Cys Cys Thr Ala Tyr Tyr Leu Thr Gln His Pro Ser Phe Ser Pro
            35                  40                  45

Ser Thr His His Ile Thr Ile Ile Glu Ser Arg Arg Ile Ala Gly Gly
        50                  55                  60

Ala Ser Gly Lys Ala Gly Gly Leu Leu Ala Ser Trp Ala Phe Pro His
65                  70                  75                  80

Gln Ile Val Pro Leu Ser Phe Gln Leu His Gln Glu Leu Ser Asp Glu
                85                  90                  95

Tyr Asp Gly Glu Asn Asn Trp Asp Tyr Arg Arg Leu Thr Thr Val Ser
                100                 105                 110

Leu Glu Ala Asp Val Arg Glu Val Ile Glu Asn Tyr Glu Arg Leu
            115                 120                 125

Ser Lys Lys Ala Tyr Asn Leu Asn Val Pro Pro Lys Lys Arg Pro
        130                 135                 140

Gly Tyr Ile Ser Asn Lys Phe Asn Ile Gly Asp Ser Asn Ser Ser Leu
145                 150                 155                 160

Ser Ser Ser Gly Ser Ser Leu Lys Asn Asp Ser Ala Ser Asn Glu Glu
                165                 170                 175

Glu Gly Ser Asp Ile His Val Ser Ser Val Pro Ser Leu His Ser
                180                 185                 190

```
Leu Thr Asn Glu Arg Met Arg Ser His Thr Asn Ser Ala Ser Asp Leu
            195                 200                 205

Asp Ser Val Ser Pro Val Glu Gln Leu Arg Glu Thr Asn Ile His Asn
        210                 215                 220

Pro Leu Pro Ala Asp Leu Asp Trp Ile Arg Arg Glu Leu Val Asn Asp
225                 230                 235                 240

Trp Ser Ser Leu Gly Gly Thr Asp Thr Thr Ala Gln Leu His Pro Tyr
                245                 250                 255

Lys Phe Thr His Phe Ile Leu Ser Lys Ala Met Glu Thr Gly Ala Val
                260                 265                 270

Asp Leu Leu Gly Lys Val Gly Leu Lys Cys Asp Glu Met Asp
            275                 280                 285

Cys Val His Ser Leu Lys Tyr Leu Pro Ser Val Val Lys Asn Arg Arg
            290                 295                 300

Asn Ser Arg Gly His Ala Glu Asn Pro Asp Ile Lys Leu Gly Thr Ile
305                 310                 315                 320

Phe Asn Asp Glu Asn Ala Lys Pro Ile Glu Ile Asn Asp Ile Gln Gln
                325                 330                 335

Ile Val Leu Ser Met Gly Pro Trp Thr Ser Lys Ile Leu Lys Asp Cys
            340                 345                 350

Pro Ile Ser Gly Leu Arg Ala His Ser Val Thr Ile Lys Pro Ser Glu
            355                 360                 365

Lys Thr Val Ser Pro Tyr Ala Ile Leu Ala Glu Leu Lys Val Asn Asp
            370                 375                 380

Arg Glu Phe Phe Ser Pro Glu Met Tyr Ala Arg Lys Asp Glu Val Tyr
385                 390                 395                 400

Val Cys Gly Glu Gly Asp Thr Leu Val Asn Ile Pro Glu Ser Ser Asp
                405                 410                 415

Asp Val Glu Val Val Ser Glu Lys Cys Asp Glu Leu Tyr His Tyr Val
            420                 425                 430

Ser Lys Leu Ser Pro Thr Leu Ser Lys Gly His Leu Leu Arg Lys Gln
            435                 440                 445

Ala Cys Phe Leu Pro Val Leu Asn Val Pro Thr Ser Ser Gly Pro Leu
            450                 455                 460

Ile Gly Glu Thr Asn Val Lys Asp Leu Tyr Ile Ala Ser Gly His Ser
465                 470                 475                 480

Cys Trp Gly Ile Asn Asn Ala Pro Ala Thr Gly Lys Leu Met Ala Glu
                485                 490                 495

Ile Leu Leu Asp Gly Glu Ala Thr Ser Ala Glu Ile Ser Ser Leu Asp
            500                 505                 510

Pro Lys Leu Tyr Phe Asp Ala Thr Ile Leu Ser
            515                 520

<210> SEQ ID NO 2
<211> LENGTH: 223
<212> TYPE: PRT
<213> ORGANISM: Saccharomyces cerevisiae

<400> SEQUENCE: 2

Met Ser Ser Gln Pro Ser Phe Val Thr Ile Arg Gly Lys Ala Ile Ser
1               5                   10                  15

Leu Glu Thr Gln Thr Glu Ser Leu Leu Ser Lys Tyr Ser Thr Phe Ala
            20                  25                  30

Gln Thr Thr Ser Ser Glu Gln Thr Gly Gln Glu Lys Lys Ile Asp Lys
```

```
            35              40              45
Gln Leu Glu Gly Ile Leu Gly Gln Arg Gln Asp Val Ile Asp Ser Leu
 50                  55                  60

Thr Gln Ile Cys Asp Ser Asn Pro Ala Ile Ser Ala Ser Lys Leu Ser
65                  70                  75                  80

Gln Leu His Arg His Lys Glu Ile Leu Gln Asp His Trp Lys Ser Phe
                85                  90                  95

Arg Asn Ile Arg Ser Ser Ile Gln Gln Glu Arg Asn Arg Leu Asn Leu
            100                 105                 110

Leu Phe Ser Val Lys Asn Asp Ile Ala Asn Ser Thr Thr Asp Ala Pro
        115                 120                 125

Ala Pro Ile Gly Asp Ala Asp Glu Tyr Ile Gln Asn Glu Thr Arg Arg
    130                 135                 140

Ile Asp Gln Ser Asn Asn Val Val Asp Arg Leu Ile Ser Gln Ala Trp
145                 150                 155                 160

Glu Thr Arg Ser Gln Phe His Ser Gln Ser Asn Val Leu Asn Thr Ala
                165                 170                 175

Asn Asn Lys Val Leu Gln Thr Leu Gln Arg Ile Pro Gly Val Asn Gln
            180                 185                 190

Leu Ile Met Lys Ile Asn Thr Arg Arg Lys Lys Asn Ala Phe Val Leu
        195                 200                 205

Ala Thr Ile Thr Thr Leu Cys Ile Leu Phe Leu Phe Phe Thr Trp
    210                 215                 220

<210> SEQ ID NO 3
<211> LENGTH: 675
<212> TYPE: PRT
<213> ORGANISM: Saccharomyces cerevisiae

<400> SEQUENCE: 3

Met Asp Tyr Glu Asp Asn Leu Glu Ala Pro Val Trp Asp Glu Leu Asn
1               5                   10                  15

His Glu Gly Asp Lys Thr Gln Ser Leu Val Ser Asn Ser Ile Glu Ser
            20                  25                  30

Ile Gly Gln Ile Ser Thr Asn Glu Glu Arg Lys Asp Asn Glu Leu Leu
        35                  40                  45

Glu Thr Thr Ala Ser Phe Ala Asp Lys Ile Asp Leu Asp Ser Ala Pro
    50                  55                  60

Glu Trp Lys Asp Pro Gly Leu Ser Val Ala Gly Asn Pro Gln Leu Glu
65                  70                  75                  80

Glu His Asp Asn Ser Lys Ala Asp Leu Ile Asn Ser Leu Ala Pro
                85                  90                  95

Glu Gln Asp Pro Ile Ala Asp Leu Lys Asn Ser Thr Thr Gln Phe Ile
            100                 105                 110

Ala Thr Arg Glu Ser Gly Gly Ala Leu Phe Thr Gly Asn Ala Asn Ser
        115                 120                 125

Pro Leu Val Phe Asp Asp Thr Ile Tyr Asp Ala Asn Thr Ser Pro Asn
    130                 135                 140

Thr Ser Lys Ser Ile Ser Gly Arg Arg Ser Gly Lys Pro Arg Ile Leu
145                 150                 155                 160

Phe Asp Ser Ala Arg Ala Gln Arg Asn Ser Lys Arg Asn His Ser Leu
                165                 170                 175

Lys Ala Lys Arg Thr Thr Ala Ser Asp Asp Thr Ile Lys Thr Pro Phe
            180                 185                 190
```

```
Thr Asp Pro Leu Lys Lys Ala Glu Lys Glu Asn Glu Phe Val Glu Glu
            195                 200                 205

Pro Leu Asp Asp Arg Asn Glu Arg Arg Glu Asn Glu Gly Lys Phe
210                 215                 220

Thr Ala Ser Val Glu Lys Asn Ile Leu Glu Gln Val Asp Arg Pro Leu
225                 230                 235                 240

Tyr Asn Leu Pro Gln Thr Gly Ala Asn Ile Ser Ser Pro Ala Glu Val
                245                 250                 255

Glu Glu Asn Ser Glu Lys Phe Gly Lys Thr Lys Ile Gly Ser Lys Val
            260                 265                 270

Pro Pro Thr Glu Lys Ala Val Ala Phe Lys Val Glu Val Lys Asp Pro
        275                 280                 285

Val Lys Val Gly Glu Leu Thr Ser Ile His Val Glu Tyr Thr Val Ile
    290                 295                 300

Ser Glu Ser Ser Leu Leu Glu Leu Lys Tyr Ala Gln Val Ser Arg Arg
305                 310                 315                 320

Tyr Arg Asp Phe Arg Trp Leu Tyr Arg Gln Leu Gln Asn Asn His Trp
                325                 330                 335

Gly Lys Val Ile Pro Pro Pro Glu Lys Gln Ser Val Gly Ser Phe
            340                 345                 350

Lys Glu Asn Phe Ile Glu Asn Arg Arg Phe Gln Met Glu Ser Met Leu
        355                 360                 365

Lys Lys Ile Cys Gln Asp Pro Val Leu Gln Lys Asp Lys Asp Phe Leu
    370                 375                 380

Leu Phe Leu Thr Ser Asp Asp Phe Ser Ser Glu Ser Lys Lys Arg Ala
385                 390                 395                 400

Phe Leu Thr Gly Ser Gly Ala Ile Asn Asp Ser Asn Asp Leu Ser Glu
                405                 410                 415

Val Arg Ile Ser Glu Ile Gln Leu Leu Gly Ala Glu Asp Ala Ala Glu
            420                 425                 430

Val Leu Lys Asn Gly Gly Ile Asp Ala Glu Ser His Lys Gly Phe Met
        435                 440                 445

Ser Ile Ser Phe Ser Ser Leu Pro Lys Tyr Asn Glu Ala Asp Glu Phe
    450                 455                 460

Phe Ile Glu Lys Lys Gln Lys Ile Asp Glu Leu Glu Asp Asn Leu Lys
465                 470                 475                 480

Lys Leu Ser Lys Ser Leu Glu Met Val Asp Thr Ser Arg Asn Thr Leu
                485                 490                 495

Ala Ala Ser Thr Glu Glu Phe Ser Ser Met Val Glu Thr Leu Ala Ser
            500                 505                 510

Leu Asn Val Ser Glu Pro Asn Ser Glu Leu Leu Asn Asn Phe Ala Asp
        515                 520                 525

Val His Lys Ser Ile Lys Ser Ser Leu Glu Arg Ser Ser Leu Gln Glu
    530                 535                 540

Thr Leu Thr Met Gly Val Met Leu Asp Asp Tyr Ile Arg Ser Leu Ala
545                 550                 555                 560

Ser Val Lys Ala Ile Phe Asn Gln Arg Ser Lys Leu Gly Tyr Phe Leu
                565                 570                 575

Val Val Ile Glu Asn Asp Met Asn Lys Lys His Ser Gln Leu Gly Lys
            580                 585                 590

Leu Gly Gln Asn Ile His Ser Glu Lys Phe Arg Glu Met Arg Lys Glu
        595                 600                 605

Phe Gln Thr Leu Glu Arg Arg Tyr Asn Leu Thr Lys Lys Gln Trp Gln
```

```
            610                 615                 620
Ala Val Gly Asp Lys Ile Lys Asp Glu Phe Gln Gly Phe Ser Thr Asp
625                 630                 635                 640

Lys Ile Arg Glu Phe Arg Asn Gly Met Glu Ile Ser Leu Glu Ala Ala
                645                 650                 655

Ile Glu Ser Gln Lys Glu Cys Ile Glu Leu Trp Glu Thr Phe Tyr Gln
                660                 665                 670

Thr Asn Leu
        675

<210> SEQ ID NO 4
<211> LENGTH: 551
<212> TYPE: PRT
<213> ORGANISM: Saccharomyces cerevisiae

<400> SEQUENCE: 4

Met Thr Ser Ala Val Pro Tyr Asp Pro Tyr Asp Asp Leu Asp Asn Asn
1               5                   10                  15

Pro Phe Ala Glu Pro Gln Glu Glu Asp Ser Glu Pro Ala Ala Thr Thr
                20                  25                  30

Thr Asp Gly Ser Ser Met Ser Glu Glu Arg Val Gly Thr Glu Gln
            35                  40                  45

Thr Ala Ala Ser Val Gln Asp Asn Gly Thr Ala Asn Asn Ile Gln Asn
50                  55                  60

Gly Leu Gly Glu Glu Gly Asn Ala Thr Arg Ser Lys Thr Ser Asn Glu
65                  70                  75                  80

His Asn Glu Asn Gln Gln Pro Ser Gln Pro Ser Glu Arg Val Ile Leu
                85                  90                  95

Pro Glu Arg Ser Asp Glu Lys Lys Lys Tyr Thr Leu Leu Ala Lys Val
                100                 105                 110

Thr Gly Leu Glu Arg Phe Gly Ser Ala Thr Gly Lys Lys Glu Asn Pro
            115                 120                 125

Thr Ile Ile Phe Asp Cys Ser Thr Asn Leu Pro Thr Phe Arg Lys Gln
130                 135                 140

Gln Tyr Lys Asn Val Lys Lys Ser Tyr Glu Glu Phe His Gln Leu Phe
145                 150                 155                 160

Lys Tyr Leu Asn Val Ala Ile Gln Glu Ser Phe Val Pro Thr Leu Pro
                165                 170                 175

Ser Ala Tyr Thr Thr Phe Gly Ile Asn Ser Glu Glu Asp Arg Met Lys
            180                 185                 190

Val Thr Arg Asn Phe Gln Leu Trp Phe Asn Arg Leu Ser Gln Asp Pro
                195                 200                 205

Leu Ile Ile Arg Asn Glu Glu Val Ala Phe Phe Ile Glu Ser Asp Phe
210                 215                 220

Asn Thr Tyr Thr Pro Ile Asn Lys Ser Lys Ser Leu Ala Ser Gly Leu
225                 230                 235                 240

Lys Arg Lys Thr Leu Lys Gln Leu Ala Pro Pro Tyr Asp Glu Ile Thr
                245                 250                 255

Glu Leu Ala Glu Phe Arg Pro Leu Val Lys Ser Ile Tyr Val Val Ser
            260                 265                 270

Gln Ser Leu Gln Glu Lys Leu Leu Arg Val Ser Arg Asn Arg Lys Met
        275                 280                 285

Met Val Gln Glu Glu Asn Ala Phe Gly Gln Asp Phe Val Asn Leu Asp
    290                 295                 300
```

```
Glu His Asn Lys Leu Tyr Arg Arg Tyr Gly Lys Ile Leu Thr Ala Val
305                 310                 315                 320

Gly Asp Ile Asp Ser Ile Ile Ala Thr Met Asp Met Ala Thr Leu Tyr
                325                 330                 335

Asp Gly Leu Glu Trp Ile Val Arg Asp Ala Tyr Ala Val Lys Glu Ala
            340                 345                 350

Leu Thr Asn Arg His Phe Ile Met Arg Asn Leu Val Gln Ala Gln Gln
        355                 360                 365

Asn Ser Lys Ala Lys Gln Glu Gln Ala Arg Arg Phe Arg Ser Arg Arg
370                 375                 380

Asp Ile Asn Pro Met Lys Ile Asp Glu Ala Leu Arg Gln Leu Lys Ala
385                 390                 395                 400

Ala Ala Lys Asn Glu Gln Val Leu Thr Leu Lys Leu Gln Arg Ile Thr
                405                 410                 415

Ser Asn Met Ile Ile Glu Arg Lys Gln Trp Ile Ser Trp Tyr Glu Glu
            420                 425                 430

Trp Ile Arg Ser Ser Ile Lys Glu Phe Thr Leu Arg Lys Ile Glu Tyr
        435                 440                 445

Glu Arg Lys Lys Leu Thr Leu Leu Glu Arg Val Arg Ser Asp Ile Arg
450                 455                 460

Lys Ala Asp Glu Asn Gly Gly Leu Ser Arg Leu Gly Arg His Ala Val
465                 470                 475                 480

Ser Asn Asn Asn Ser Asp Thr Ser Gln Thr Leu Lys Gly Asp Ser Trp
                485                 490                 495

Thr Gly Glu Ser Asn Arg Lys Ser Gln Ile Pro Ile Asn Lys Ile Ala
            500                 505                 510

His Thr Glu Phe Asp Asp Glu Leu Phe Thr Glu Asp Asp Gly Tyr Asn
        515                 520                 525

Ser Gln Asp Ser Asp Thr Thr Ser Leu Asn Ala Arg His Ala Ala Ser
530                 535                 540

Leu Leu Gly Met Ser Thr Lys
545                 550

<210> SEQ ID NO 5
<211> LENGTH: 379
<212> TYPE: PRT
<213> ORGANISM: Saccharomyces cerevisiae

<400> SEQUENCE: 5

Met Ser Ile Phe Phe Lys Pro Pro Ile Asp Ile Glu Ile Leu Phe Asp
1               5                   10                  15

Asn Glu Glu Ser Arg Lys His Val Asp Ile Ala Thr Arg Ser Ser Asn
                20                  25                  30

Ser Ser Tyr Lys Ser Met Lys Glu Ser Leu Pro Val Tyr Glu Asp Gly
            35                  40                  45

Glu Ser Leu Gly Gly Ile Val Thr Leu Arg Val Arg Asp Ser Lys Lys
        50                  55                  60

Val Asp His Leu Gly Ile Lys Val Ser Val Ile Gly Ser Ile Asp Met
65                  70                  75                  80

Leu Lys Ser His Gly Ser Gly Asn Ser Ser Lys Lys Val Thr Ser
                85                  90                  95

Ser Thr Ser Ser Ser Ser Ser Asn Gly Ser Val Asp Val Arg Lys Asn
            100                 105                 110

Ser Val Asp Gln Phe Leu Cys Gln Ser Tyr Asp Leu Cys Pro Ala Gly
        115                 120                 125
```

```
Glu Leu Gln His Ser Gln Ser Phe Pro Phe Leu Phe Arg Asp Leu Ser
    130                 135                 140

Lys Arg Tyr Glu Ser Tyr Lys Gly Lys Asn Val Asp Val Ala Tyr Tyr
145                 150                 155                 160

Val Lys Val Thr Val Met Arg Lys Ser Thr Asp Ile Ser Lys Ile Lys
                165                 170                 175

Arg Phe Trp Val Tyr Leu Tyr Asn Ser Val Thr Thr Ala Pro Asn Thr
            180                 185                 190

Leu Ser Ala Asn Glu Thr Lys Ala Thr Thr Asn Asp Ile Ala Gly Gly
        195                 200                 205

Asn Tyr Ala Ala Asp Asn Ala Ser Asp Asn Thr Gln Thr Lys Ser Thr
    210                 215                 220

Gln Gly Glu Ala Ala Asp Val Asn Gln Val Leu Pro Ile Ser His Ser
225                 230                 235                 240

Asn Asn Glu Pro Lys Pro Val Arg Leu Asp Ile Gly Ile Glu Asn Cys
                245                 250                 255

Leu His Ile Glu Phe Glu Tyr Ala Lys Ser Gln Tyr Ser Leu Lys Glu
            260                 265                 270

Val Ile Val Gly Arg Ile Tyr Phe Leu Leu Thr Arg Leu Arg Ile Lys
        275                 280                 285

His Met Glu Leu Ser Leu Ile Thr Arg Glu Ser Ser Gly Leu Gln Thr
    290                 295                 300

Ser Asn Val Met Thr Asp Ser Thr Ala Ile Arg Tyr Glu Ile Met Asp
305                 310                 315                 320

Gly Ser Ser Val Lys Gly Glu Thr Ile Pro Ile Arg Leu Phe Leu Ser
                325                 330                 335

Gly Tyr Asp Leu Thr Pro Asn Met Ser Cys Asn Tyr Phe Asn Val Lys
            340                 345                 350

Asn Tyr Leu Ser Leu Val Ile Ile Asp Glu Asp Gly Arg Arg Tyr Phe
        355                 360                 365

Lys Gln Ser Glu Ile Thr Leu Tyr Arg Thr Arg
    370                 375

<210> SEQ ID NO 6
<211> LENGTH: 282
<212> TYPE: PRT
<213> ORGANISM: Saccharomyces cerevisiae

<400> SEQUENCE: 6

Met Leu Leu Leu Ala Leu Ser Asp Ala His Ile Pro Asp Arg Ala Thr
1               5                   10                  15

Asp Leu Pro Val Lys Phe Lys Lys Leu Leu Ser Val Pro Asp Lys Ile
            20                  25                  30

Ser Gln Val Ala Leu Leu Gly Asn Ser Thr Lys Ser Tyr Asp Phe Leu
        35                  40                  45

Lys Phe Val Asn Gln Ile Ser Asn Asn Ile Thr Ile Val Arg Gly Glu
    50                  55                  60

Phe Asp Asn Gly His Leu Pro Ser Thr Lys Lys Asp Lys Ala Ser Asp
65                  70                  75                  80

Asn Ser Arg Pro Met Glu Glu Ile Pro Met Asn Ser Ile Ile Arg Gln
                85                  90                  95

Gly Ala Leu Lys Ile Gly Cys Cys Ser Gly Tyr Thr Val Val Pro Lys
            100                 105                 110

Asn Asp Pro Leu Ser Leu Leu Ala Leu Ala Arg Gln Leu Asp Val Asp
```

```
            115                 120                 125
Ile Leu Leu Trp Gly Gly Thr His Asn Val Glu Ala Tyr Thr Leu Glu
130                 135                 140

Gly Lys Phe Phe Val Asn Pro Gly Ser Cys Thr Gly Ala Phe Asn Thr
145                 150                 155                 160

Asp Trp Pro Ile Val Phe Asp Val Glu Asp Ser Asp Glu Ala Val Thr
                165                 170                 175

Ser Glu Val Asp Lys Pro Thr Lys Glu Asn Gln Ser Gly Asp Asp Asp
                180                 185                 190

Ala Lys Gly Gly Ser Thr Gly Lys Glu Gln Pro Gly Ser Tyr Thr Pro
                195                 200                 205

Lys Glu Gly Thr Ala Gly Glu Arg Glu Asn Glu Asn Glu Ser Asn Val
                210                 215                 220

Lys Pro Glu Asn Gln Phe Lys Glu Asp Glu Val Asp Met Ser Asp Ser
225                 230                 235                 240

Asp Ile Asn Gly Ser Asn Ser Pro Ser Phe Cys Leu Leu Asp Ile Gln
                245                 250                 255

Gly Asn Thr Cys Thr Leu Tyr Ile Tyr Leu Tyr Val Asn Gly Glu Val
                260                 265                 270

Lys Val Asp Lys Val Val Tyr Glu Lys Glu
                275                 280
```

<210> SEQ ID NO 7
<211> LENGTH: 944
<212> TYPE: PRT
<213> ORGANISM: Saccharomyces cerevisiae

<400> SEQUENCE: 7

```
Met Ala Tyr Ala Asp Ser Pro Glu Asn Ala Ile Ala Val Ile Lys Gln
1               5                   10                  15

Arg Thr Ala Leu Met Asn Arg Cys Leu Ser Gln His Lys Leu Met Glu
                20                  25                  30

Ser Leu Gln His Thr Ser Ile Met Leu Thr Glu Leu Arg Asn Pro Asn
            35                  40                  45

Leu Ser Pro Lys Lys Tyr Tyr Glu Leu Tyr Val Ile Ile Phe Asp Ser
    50                  55                  60

Leu Thr Asn Leu Ser Thr Tyr Leu Ile Glu Asn His Pro Gln Asn His
65                  70                  75                  80

His Leu Ala Asp Leu Tyr Glu Leu Val Gln Tyr Thr Gly Asn Val Val
                85                  90                  95

Pro Arg Leu Tyr Leu Met Ile Thr Val Gly Thr Ser Tyr Leu Thr Phe
                100                 105                 110

Asn Glu Ala Pro Lys Lys Glu Ile Leu Lys Asp Met Ile Glu Met Cys
                115                 120                 125

Arg Gly Val Gln Asn Pro Ile Arg Gly Leu Phe Leu Arg Tyr Tyr Leu
130                 135                 140

Ser Gln Arg Thr Lys Glu Leu Leu Pro Glu Asp Pro Ser Phe Asn
145                 150                 155                 160

Ser Gln Phe Ile Met Asn Asn Phe Ile Glu Met Asn Lys Leu Trp Val
                165                 170                 175

Arg Leu Gln His Gly Pro Leu Arg Glu Arg Glu Thr Arg Thr Arg
                180                 185                 190

Glu Arg Lys Glu Leu Gln Ile Leu Val Gly Ser Gln Leu Val Arg Leu
                195                 200                 205
```

```
Ser Gln Ile Ile Asp Asp Asn Phe Gln Met Tyr Lys Gln Asp Ile Leu
    210                 215                 220
Pro Thr Ile Leu Glu Gln Val Ile Gln Cys Arg Asp Leu Val Ser Gln
225                 230                 235                 240
Glu Tyr Leu Leu Asp Val Ile Cys Gln Val Phe Ala Asp Glu Phe His
                245                 250                 255
Leu Lys Thr Leu Asp Thr Leu Gln Thr Thr Leu His Leu Asn Pro
                260                 265                 270
Asp Val Ser Ile Asn Lys Ile Val Leu Thr Leu Val Asp Arg Leu Asn
                275                 280                 285
Asp Tyr Val Thr Arg Gln Leu Glu Asp Asp Pro Asn Ala Thr Ser Thr
290                 295                 300
Asn Ala Tyr Leu Asp Met Asp Val Phe Gly Thr Phe Trp Asp Tyr Leu
305                 310                 315                 320
Thr Val Leu Asn His Glu Arg Pro Asp Leu Ser Leu Gln Gln Phe Ile
                325                 330                 335
Pro Leu Val Glu Ser Val Ile Val Leu Ser Leu Lys Trp Tyr Pro Asn
                340                 345                 350
Asn Phe Asp Asn Leu Asn Lys Leu Phe Glu Leu Val Leu Gln Lys Thr
                355                 360                 365
Lys Asp Tyr Gly Gln Lys Asn Ile Ser Leu Glu Ser Glu His Leu Phe
                370                 375                 380
Leu Val Leu Leu Ser Phe Gln Asn Ser Lys Leu Gln Leu Thr Ser Ser
385                 390                 395                 400
Thr Thr Ala Pro Pro Asn Ser Pro Val Thr Ser Lys Lys His Phe Ile
                405                 410                 415
Phe Gln Leu Ile Ser Gln Cys Gln Ala Tyr Lys Asn Ile Leu Ala Leu
                420                 425                 430
Gln Ser Ile Ser Leu Gln Lys Lys Val Val Asn Glu Ile Ile Asp Ile
                435                 440                 445
Leu Met Asp Arg Glu Val Glu Glu Met Ala Asp Asn Asp Ser Glu Ser
                450                 455                 460
Lys Leu His Pro Pro Gly His Ser Ala Tyr Leu Val Ile Glu Asp Lys
465                 470                 475                 480
Leu Gln Val Gln Arg Leu Leu Ser Ile Cys Glu Pro Leu Ile Ile Ser
                485                 490                 495
Arg Ser Gly Pro Pro Ala Asn Val Ala Ser Ser Asp Thr Asn Val Asp
                500                 505                 510
Glu Val Phe Phe Asn Arg His Asp Glu Glu Ser Trp Ile Leu Asp
                515                 520                 525
Pro Ile Gln Glu Lys Leu Ala His Leu Ile His Trp Ile Met Asn Thr
                530                 535                 540
Thr Ser Arg Lys Gln Thr Met Lys Asn Lys Ile Gln Phe Ser Leu Glu
545                 550                 555                 560
Ala Gln Leu Glu Ile Leu Leu Ile Lys Ser Ser Phe Ile Lys Gly
                565                 570                 575
Gly Ile Asn Val Lys Tyr Thr Phe Pro Ala Ile Ile Thr Asn Phe Trp
                580                 585                 590
Lys Leu Met Arg Lys Cys Arg Met Ile Gln Glu Tyr Leu Leu Lys Lys
                595                 600                 605
Arg Pro Asp Asn Lys Thr Leu Leu Ser His Tyr Ser Asn Leu Leu Lys
610                 615                 620
Gln Met Phe Lys Phe Val Ser Arg Cys Ile Asn Asp Ile Phe Asn Ser
```

```
                625                 630                 635                 640
        Cys Asn Asn Ser Cys Thr Asp Leu Ile Leu Lys Leu Asn Leu Gln Cys
                        645                 650                 655

Ala Ile Leu Ala Asp Gln Leu Gln Leu Asn Glu Ile Ser Tyr Asp Phe
                660                 665                 670

Phe Ser Gln Ala Phe Thr Ile Phe Glu Glu Ser Leu Ser Asp Ser Lys
                    675                 680                 685

Thr Gln Leu Gln Ala Leu Ile Tyr Ile Ala Gln Ser Leu Gln Lys Thr
            690                 695                 700

Arg Ser Leu Tyr Lys Glu Ala Tyr Tyr Asp Ser Leu Ile Val Arg Cys
        705                 710                 715                 720

Thr Leu His Gly Ser Lys Leu Leu Lys Lys Gln Asp Gln Cys Arg Ala
                        725                 730                 735

Val Tyr Leu Cys Ser His Leu Trp Trp Ala Thr Glu Ile Ser Asn Ile
                    740                 745                 750

Gly Glu Glu Glu Gly Ile Thr Asp Asn Phe Tyr Arg Asp Gly Lys Arg
                755                 760                 765

Val Leu Glu Cys Leu Gln Arg Ser Leu Arg Val Ala Asp Ser Ile Met
            770                 775                 780

Asp Asn Glu Gln Ser Cys Glu Leu Met Val Glu Ile Leu Asn Arg Cys
        785                 790                 795                 800

Leu Tyr Tyr Phe Ile His Gly Asp Glu Ser Glu Thr His Ile Ser Ile
                        805                 810                 815

Lys Tyr Ile Asn Gly Leu Ile Glu Leu Ile Lys Thr Asn Leu Lys Ser
                    820                 825                 830

Leu Lys Leu Glu Asp Asn Ser Ala Ser Met Ile Thr Asn Ser Ile Ser
                835                 840                 845

Asp Leu His Ile Thr Gly Glu Asn Asn Val Lys Ala Ser Ser Asn Ala
            850                 855                 860

Asp Asp Gly Ser Val Ile Thr Asp Lys Glu Ser Asn Val Ala Ile Gly
        865                 870                 875                 880

Ser Asp Gly Thr Tyr Ile Gln Leu Asn Thr Leu Asn Gly Ser Ser Thr
                        885                 890                 895

Leu Ile Arg Gly Val Val Ala Thr Ala Ser Gly Ser Lys Leu Leu His
                    900                 905                 910

Gln Leu Lys Tyr Ile Pro Ile His His Phe Arg Arg Thr Cys Glu Tyr
                915                 920                 925

Ile Glu Ser Gln Arg Glu Val Asp Asp Arg Phe Lys Val Ile Tyr Val
            930                 935                 940

<210> SEQ ID NO 8
<211> LENGTH: 674
<212> TYPE: PRT
<213> ORGANISM: Saccharomyces cerevisiae

<400> SEQUENCE: 8

Met Ser Arg Lys Asn Ser Lys Lys Leu Lys Val Tyr Tyr Leu Pro Val
1               5                   10                  15

Thr Leu Thr Gln Phe Gln Lys Asp Leu Ser Glu Ile Leu Ile Ser Leu
            20                  25                  30

His Ala Lys Ser Phe Lys Ala Ser Leu Ile Gly Glu Pro Gln Ala Asp
        35                  40                  45

Ala Val Asn Lys Pro Ser Gly Leu Pro Ala Gly Pro Glu Thr His Pro
    50                  55                  60
```

```
Tyr Pro Thr Leu Ser Gln Arg Gln Leu Thr Tyr Ile Phe Asp Ser Asn
 65                  70                  75                  80

Ile Arg Ala Ile Ala Asn His Pro Ser Leu Leu Val Asp His Tyr Met
                 85                  90                  95

Pro Arg Gln Leu Leu Arg Met Glu Pro Thr Glu Ser Ser Ile Ala Gly
            100                 105                 110

Ser His Lys Phe Gln Val Leu Asn Gln Leu Ile Asn Ser Ile Cys Phe
        115                 120                 125

Arg Asp Arg Glu Gly Ser Pro Asn Glu Val Ile Lys Cys Ala Ile Ile
    130                 135                 140

Ala His Ser Ile Lys Glu Leu Asp Leu Leu Glu Gly Leu Ile Leu Gly
145                 150                 155                 160

Lys Lys Phe Arg Thr Lys Arg Leu Ser Gly Thr Ser Leu Tyr Asn Glu
                165                 170                 175

Lys His Lys Phe Pro Asn Leu Pro Thr Val Asp Ser Thr Ile Asn Lys
            180                 185                 190

Asp Gly Thr Pro Asn Ser Val Ser Ser Thr Ser Ser Asn Ser Asn Ser
        195                 200                 205

Thr Ser Tyr Thr Gly Tyr Ser Lys Asp Asp Tyr Asp Tyr Ser Val Lys
    210                 215                 220

Arg Asn Leu Lys Lys Arg Lys Ile Asn Thr Asp Asp Trp Leu Phe Leu
225                 230                 235                 240

Ala Thr Thr Lys His Leu Lys His Asp Gln Tyr Leu Leu Ala Asn Tyr
                245                 250                 255

Asp Ile Asp Met Ile Ile Ser Phe Asp Pro Met Leu Glu Ile Glu Leu
            260                 265                 270

Pro Ala Leu Gln Val Leu Arg Asn Asn Ala Asn Lys Asp Ile Pro Ile
        275                 280                 285

Ile Lys Leu Leu Val Gln Asn Ser Pro Asp His Tyr Leu Leu Asp Ser
    290                 295                 300

Glu Ile Lys Asn Ser Ser Val Lys Ser Ser His Leu Ser Asn Asn Gly
305                 310                 315                 320

His Val Asp Asp Ser Gln Glu Tyr Glu Ile Lys Ser Ser Leu Leu
                325                 330                 335

Tyr Phe Leu Gln Ala Arg Asn Ala Pro Val Asn Asn Cys Glu Ile Asp
            340                 345                 350

Tyr Ile Lys Leu Val Lys Cys Cys Leu Glu Gly Lys Asp Cys Asn Asn
        355                 360                 365

Ile Leu Pro Val Leu Asp Leu Ile Thr Leu Asp Glu Ala Ser Lys Asp
    370                 375                 380

Ser Ser Asp Ser Gly Phe Trp Gln Pro Gln Leu Thr Lys Leu Gln Tyr
385                 390                 395                 400

Ser Ser Thr Glu Leu Pro Leu Trp Asp Gly Pro Leu Asp Ile Lys Thr
                405                 410                 415

Tyr Gln Thr Asp Leu Met His Arg Ala Val Ile Arg Leu Arg Asp Ile
            420                 425                 430

Gln Asp Glu Tyr Ala Lys Gly Thr Val Pro Leu Tyr Glu Lys Arg Leu
        435                 440                 445

Asn Glu Thr Gln Arg Gln Asn Gln Leu Asp Glu Ile Lys Asn Ser Val
    450                 455                 460

Gly Leu Thr Phe Lys Lys Lys Gln Glu Met Glu Lys Ser Ile Asn Asp
465                 470                 475                 480

Ser Glu Lys Arg Leu Lys His Ala Met Thr Glu Ser Thr Lys Leu Gln
```

```
            485                 490                 495
Asn Lys Ile Asn His Leu Leu Lys Ile Arg Gln Glu Leu Glu Asn Phe
            500                 505                 510

Asn Lys Leu Pro Ser Asn Thr Thr Ser Ser Glu Asn His Leu Glu Glu
            515                 520                 525

Gly Ser Ala Leu Ala Asp Lys Leu Lys Glu Tyr Ile Asp Lys Asn Ala
            530                 535                 540

Thr Leu Phe Asn Lys Leu Lys Glu Leu Gln Gln Ala Asn Ala Glu Lys
545                 550                 555                 560

Ser Lys Leu Asn Asp Glu Leu Arg Ser Lys Tyr Gln Ile Glu Ser Ser
            565                 570                 575

Lys Ala Ala Glu Ser Ala Gln Thr Leu Lys Ile Leu Arg Glu Ser Met
            580                 585                 590

Lys Ser Leu Glu Asn Glu Val Asn Gly Pro Leu Thr Lys Phe Ser Thr
            595                 600                 605

Glu Ser Leu Lys Lys Glu Leu Glu Arg Leu Gln Asn Asp Phe Gln Ser
            610                 615                 620

Leu Lys Ala Arg Asn Lys Phe Leu Lys Asn Tyr Ile Thr Leu Met Asn
625                 630                 635                 640

Arg Gln Tyr Asp Leu Lys Asn Lys Asn Asn Val Gln Val Glu Lys Ala
            645                 650                 655

Ala Ala Asn Gly Thr Arg Phe Arg Ser Thr Arg Ser Asn Thr Pro Asn
            660                 665                 670

Tyr Thr

<210> SEQ ID NO 9
<211> LENGTH: 655
<212> TYPE: PRT
<213> ORGANISM: Saccharomyces cerevisiae

<400> SEQUENCE: 9

Met Asp Leu Leu Arg Ile Leu Asp Thr Lys Pro Ile Pro Thr Ile Val
1               5                   10                  15

Asp Ala Thr Thr Leu Gly Ile Ser Gly Asn Thr Ser Gly Asp Tyr Trp
            20                  25                  30

Leu Pro Thr Thr Met Ser Leu Tyr Gln Lys Glu Leu Thr Asp Gln Ile
            35                  40                  45

Val Ser Leu His Tyr Ser Asp Ile Leu Arg Tyr Phe Glu Thr Ser His
            50                  55                  60

Tyr Lys Glu Asp Val Ile Leu Glu Ser Met Lys Thr Met Cys Leu Asn
65                  70                  75                  80

Gly Ser Leu Val Ala Thr His Pro Tyr Leu Leu Ile Asp His Tyr Met
            85                  90                  95

Pro Lys Ser Leu Ile Thr Arg Asp Val Pro Ala His Leu Ala Glu Asn
            100                 105                 110

Ser Gly Lys Phe Ser Val Leu Arg Asp Leu Ile Asn Leu Val Gln Glu
            115                 120                 125

Tyr Glu Thr Glu Thr Ala Ile Val Cys Arg Pro Gly Arg Thr Met Asp
            130                 135                 140

Leu Leu Glu Ala Leu Leu Gly Asn Lys Val His Ile Lys Arg Tyr
145                 150                 155                 160

Asp Gly His Ser Ile Lys Ser Lys Gln Lys Ala Asn Asp Phe Ser Cys
            165                 170                 175

Thr Val His Leu Phe Ser Ser Glu Gly Ile Asn Phe Thr Lys Tyr Pro
```

```
                180                 185                 190
Ile Lys Ser Lys Ala Arg Phe Asp Met Leu Ile Cys Leu Asp Thr Thr
            195                 200                 205
Val Asp Thr Ser Gln Lys Asp Ile Gln Tyr Leu Leu Gln Tyr Lys Arg
            210                 215                 220
Glu Arg Lys Gly Leu Glu Arg Tyr Ala Pro Ile Val Arg Leu Val Ala
225                 230                 235                 240
Ile Asn Ser Ile Asp His Cys Thr Leu Phe Phe Gly Lys Lys Phe Asp
            245                 250                 255
Lys Asn Ser Arg Glu Tyr Leu Glu Asn Val Thr Ala Ala Met Val Ile
            260                 265                 270
Leu Arg Asp Arg Leu Gly Thr Leu Pro Pro Asp Leu Arg Pro Ile Tyr
            275                 280                 285
Ser Gln Lys Leu His Tyr Leu Val Glu Trp Leu Glu Asn Pro Thr Val
            290                 295                 300
Pro Trp Pro Leu Pro Asp Ile Tyr Pro Leu Lys Gln Tyr Thr Ser Met
305                 310                 315                 320
Asp Val Glu Arg Ser Leu Leu Thr Glu Val His Phe Lys Lys Ser Asp
                325                 330                 335
Asp Gln Leu Glu Asp Ala Phe Ser Asn Cys Ser Lys Lys Arg Gly Arg
                340                 345                 350
His Gly Ala Asn Lys Ala Ala Ser Ser Thr Val Ala Gly Ile Glu Asp
            355                 360                 365
Asn Ile Thr Pro Ser Phe Tyr Ser Thr Lys Arg Leu Lys Asn Asp Tyr
            370                 375                 380
Tyr Thr Asn Pro Leu Lys Gln Asp Met Thr Gln Leu Thr Gly Ile Thr
385                 390                 395                 400
Thr Ala Asp Asn Ser Ser Asn Val Asn Tyr His Leu Ser Ser Gly Ile
                405                 410                 415
Ile Thr His Lys Leu Ile Gln Ser Met Gly Glu Val Tyr Met Asp Ile
            420                 425                 430
Cys Val Gln Lys Gln Glu Leu Asp Asp Tyr Ser Cys Leu Asp Asp Leu
            435                 440                 445
Gln Asn Asp His Leu Lys Phe Phe Ser Asn Glu Asp Glu Lys Ile Ile
            450                 455                 460
Lys Glu Tyr Glu Thr Val Leu Arg Thr Asn Asn Asp Asn Leu Asn Arg
465                 470                 475                 480
Ser His Glu Leu Glu Val Glu Asn Asn Leu Lys Phe Ser Gln Ile Glu
                485                 490                 495
Thr Leu Glu Lys Asp Ile Glu Thr Leu Lys Gly Ser Leu Met Ala Gln
            500                 505                 510
Gly Glu Thr Leu Ser Lys Leu Lys Asp Ala Phe Val Lys Thr Asp Asn
            515                 520                 525
Val Gln Asp Glu Ile Glu Lys Glu Arg Ile Ser Val Ser Arg Asp
            530                 535                 540
Thr Glu Lys Lys Tyr Met Glu Gln Glu Ile Lys Arg Ala Val Asp Ala
545                 550                 555                 560
Ile Arg Glu Asn Glu Glu Thr His Lys Leu Asn Glu Lys Lys Asn
                565                 570                 575
Gly Leu Glu Ser Glu Leu Lys Leu Lys Phe Gly Lys Ser Glu Ile Ser
            580                 585                 590
Thr Lys Glu Leu Asn Glu Lys Ile Gly Phe Leu Lys Lys Glu Leu Lys
            595                 600                 605
```

```
Leu Glu Asn Asp Leu Asn Glu Glu Leu Met Gly Gln Leu Ser Lys Thr
            610                 615                 620
Met Asp Asn Leu Glu Asn Leu Thr Ile Pro Arg Val Arg Thr Gln Asn
625                 630                 635                 640
Gly Asn Thr Lys Lys Lys Ser Lys Ala Lys Lys Pro Gly Asn Val
                645                 650                 655
```

<210> SEQ ID NO 10
<211> LENGTH: 569
<212> TYPE: PRT
<213> ORGANISM: Saccharomyces cerevisiae

<400> SEQUENCE: 10

```
Met Ser Phe Gln Ile Glu Thr Val Pro Thr Lys Pro Tyr Glu Asp Gln
1               5                   10                  15
Lys Pro Gly Thr Ser Gly Leu Arg Lys Lys Thr Lys Val Phe Lys Asp
                20                  25                  30
Glu Pro Asn Tyr Thr Glu Asn Phe Ile Gln Ser Ile Met Glu Ala Ile
            35                  40                  45
Pro Glu Gly Ser Lys Gly Ala Thr Leu Val Val Gly Gly Asp Gly Arg
        50                  55                  60
Tyr Tyr Asn Asp Val Ile Leu His Lys Ile Ala Ala Ile Gly Ala Ala
65                  70                  75                  80
Asn Gly Ile Lys Lys Leu Val Ile Gly Gln His Gly Leu Leu Ser Thr
                85                  90                  95
Pro Ala Ala Ser His Ile Met Arg Thr Tyr Glu Glu Lys Cys Thr Gly
            100                 105                 110
Gly Ile Ile Leu Thr Ala Ser His Asn Pro Gly Gly Pro Glu Asn Asp
        115                 120                 125
Met Gly Ile Lys Tyr Asn Leu Ser Asn Gly Gly Pro Ala Pro Glu Ser
    130                 135                 140
Val Thr Asn Ala Ile Trp Glu Ile Ser Lys Lys Leu Thr Ser Tyr Lys
145                 150                 155                 160
Ile Ile Lys Asp Phe Pro Glu Leu Asp Leu Gly Thr Ile Gly Lys Asn
                165                 170                 175
Lys Lys Tyr Gly Pro Leu Leu Val Asp Ile Ile Asp Ile Thr Lys Asp
            180                 185                 190
Tyr Val Thr Phe Leu Lys Glu Ile Phe Asp Phe Asp Leu Ile Lys Lys
        195                 200                 205
Phe Ile Asp Asn Gln Arg Ser Thr Lys Asn Trp Lys Leu Leu Phe Asp
    210                 215                 220
Ser Met Asn Gly Val Thr Gly Pro Tyr Gly Lys Ala Ile Phe Val Asp
225                 230                 235                 240
Glu Phe Gly Leu Pro Ala Asp Glu Val Leu Gln Asn Trp His Pro Ser
                245                 250                 255
Pro Asp Phe Gly Gly Met His Pro Asp Pro Asn Leu Thr Tyr Ala Ser
            260                 265                 270
Ser Leu Val Lys Arg Val Asp Arg Glu Lys Ile Glu Phe Gly Ala Ala
        275                 280                 285
Ser Asp Gly Asp Gly Asp Arg Asn Met Ile Tyr Gly Tyr Gly Pro Ser
    290                 295                 300
Phe Val Ser Pro Gly Asp Ser Val Ala Ile Ala Glu Tyr Ala Ala
305                 310                 315                 320
Glu Ile Pro Tyr Phe Ala Lys Gln Gly Ile Tyr Gly Leu Ala Arg Ser
```

```
                   325                 330                 335
Phe Pro Thr Ser Gly Ala Ile Asp Arg Val Ala Lys Ala His Gly Leu
            340                 345                 350
Asn Cys Tyr Glu Val Pro Thr Gly Trp Lys Phe Phe Cys Ala Leu Phe
        355                 360                 365
Asp Ala Lys Lys Leu Ser Ile Cys Gly Glu Glu Ser Phe Gly Thr Gly
    370                 375                 380
Ser Asn His Val Arg Glu Lys Asp Gly Val Trp Ala Ile Met Ala Trp
385                 390                 395                 400
Leu Asn Ile Leu Ala Ile Tyr Asn Lys His His Pro Glu Asn Glu Ala
                405                 410                 415
Ser Ile Lys Thr Ile Gln Asn Glu Phe Trp Ala Lys Tyr Gly Arg Thr
            420                 425                 430
Phe Phe Thr Arg Tyr Asp Phe Glu Lys Val Thr Glu Lys Ala Asn
        435                 440                 445
Lys Ile Val Asp Gln Leu Arg Ala Tyr Val Thr Lys Ser Gly Val Val
    450                 455                 460
Asn Ser Ala Phe Pro Ala Asp Glu Ser Leu Lys Val Thr Asp Cys Gly
465                 470                 475                 480
Asp Phe Ser Tyr Thr Asp Leu Asp Gly Ser Val Ser Asp His Gln Gly
                485                 490                 495
Leu Tyr Val Lys Leu Ser Asn Gly Ala Arg Phe Val Leu Arg Leu Ser
            500                 505                 510
Gly Thr Gly Ser Ser Gly Ala Thr Ile Arg Leu Tyr Ile Glu Lys Tyr
        515                 520                 525
Cys Asp Asp Lys Ser Gln Tyr Gln Lys Thr Ala Glu Glu Tyr Leu Lys
    530                 535                 540
Pro Ile Ile Asn Ser Val Ile Lys Phe Leu Asn Phe Lys Gln Val Leu
545                 550                 555                 560
Gly Thr Glu Glu Pro Thr Val Arg Thr
                565

<210> SEQ ID NO 11
<211> LENGTH: 870
<212> TYPE: PRT
<213> ORGANISM: Saccharomyces cerevisiae

<400> SEQUENCE: 11

Met Ser Thr Thr Leu Ala Ala Pro Ala Lys Leu Lys Ser Leu Leu Leu
1               5                   10                  15
Asn Leu His Thr His Cys Ile Gly Leu His Val Asn Asp Val Thr Pro
                20                  25                  30
Lys Val Tyr Phe Lys Leu Leu Ile Arg His Leu Leu Gln Ile Ser Arg
            35                  40                  45
Ser Asn Ala Ala His Pro Lys Leu Arg Arg Arg Ala Gln Ile Leu Leu
        50                  55                  60
Val Ser Leu Phe Leu Ser Gly Val Thr Leu Phe Ser Gly Val Thr Tyr
65                  70                  75                  80
Ser Thr Phe Lys Ile Ile Leu Lys Cys Tyr Lys Phe Tyr Lys Phe Pro
                85                  90                  95
Trp Lys Arg Arg Asn Arg Arg Pro Leu Ile Arg Arg Thr Arg Ser Gln
                100                 105                 110
Met Gln Leu Asp Ser Gly Ala Arg Ile Met Tyr Ile Pro Glu Val Glu
            115                 120                 125
```

```
Leu Val Asp Arg Gln Ser Pro Asp Asp Asn Lys Phe Met Asn Ala Thr
130                 135                 140

Asp Lys Lys Arg Lys Arg Ile Phe Ile Pro Pro Lys Asp Asn Asp
145                 150                 155                 160

Val Tyr Glu His Asp Lys Phe Leu Phe Lys Asn Val Glu Leu Glu Arg
                165                 170                 175

Ala Lys Asn Ser Gln Leu Phe Tyr Ser Lys Phe Leu Asn Gln Met Asn
            180                 185                 190

Val Leu Ser Lys Ile Leu Ile Pro Thr Val Phe Asp Lys Asn Phe Leu
        195                 200                 205

Leu Leu Thr Ala Gln Ile Phe Phe Leu Val Met Arg Thr Trp Leu Ser
210                 215                 220

Leu Phe Val Ala Lys Leu Asp Gly Gln Ile Val Lys Asn Ile Ile Ala
225                 230                 235                 240

Gly Arg Gly Arg Ser Phe Leu Trp Asp Leu Gly Cys Trp Phe Leu Ile
                245                 250                 255

Ala Val Pro Ala Ser Tyr Thr Asn Ser Ala Ile Lys Leu Leu Gln Arg
            260                 265                 270

Lys Leu Ser Leu Asn Phe Arg Val Asn Leu Thr Arg Tyr Ile His Asp
        275                 280                 285

Met Tyr Leu Asp Lys Arg Leu Thr Phe Tyr Lys Leu Ile Phe Asp Ala
290                 295                 300

Lys Ala Ser Asn Ser Val Ile Lys Asn Ile Asp Asn Ser Ile Thr Asn
305                 310                 315                 320

Asp Val Ala Lys Phe Cys Asp Ala Thr Cys Ser Val Phe Ala Asn Ile
                325                 330                 335

Ala Lys Pro Val Ile Asp Leu Ile Phe Phe Ser Val Tyr Leu Arg Asp
            340                 345                 350

Asn Leu Gly Thr Val Gly Val Ala Gly Ile Phe Val Asn Tyr Phe Ile
        355                 360                 365

Thr Gly Phe Ile Leu Arg Lys Tyr Thr Pro Pro Leu Gly Lys Leu Ala
370                 375                 380

Gly Glu Arg Ser Ala Ser Asp Gly Asp Tyr Tyr Asn Tyr His Leu Asn
385                 390                 395                 400

Met Ile Asn Asn Ser Glu Glu Ile Ala Phe Tyr Gln Gly Thr Ala Val
                405                 410                 415

Glu Arg Thr Lys Val Lys Glu Leu Tyr Asp Val Leu Met Glu Lys Met
            420                 425                 430

Leu Leu Val Asp Lys Val Lys Phe Gly Tyr Asn Met Leu Glu Asp Tyr
        435                 440                 445

Val Leu Lys Tyr Thr Trp Ser Gly Leu Gly Tyr Val Phe Ala Ser Ile
450                 455                 460

Pro Ile Val Met Ser Thr Leu Ala Thr Gly Ile Asn Ser Glu Glu Lys
465                 470                 475                 480

Asn Met Lys Glu Phe Ile Val Asn Lys Arg Leu Met Leu Ser Leu Ala
                485                 490                 495

Asp Ala Gly Ser Arg Leu Met His Ser Ile Lys Asp Ile Ser Gln Leu
            500                 505                 510

Thr Gly Tyr Thr Asn Arg Ile Phe Thr Leu Leu Ser Val Leu His Arg
        515                 520                 525

Val His Ser Leu Asn Phe Asn Tyr Gly Ala Val Pro Ser Ile Leu Ser
530                 535                 540

Ile Arg Thr Glu Asp Ala Ser Arg Asn Ser Asn Leu Leu Pro Thr Thr
```

```
                545                 550                 555                 560
        Asp Asn Ser Gln Asp Ala Ile Arg Gly Thr Ile Gln Arg Asn Phe Asn
                        565                 570                 575

Gly Ile Arg Leu Glu Asn Ile Asp Val Ile Ile Pro Ser Val Arg Ala
                        580                 585                 590

Ser Glu Gly Ile Lys Leu Ile Asn Lys Leu Thr Phe Gln Ile Pro Leu
                        595                 600                 605

His Ile Asp Pro Ile Thr Ser Lys Ser Asn Ser Ile Gln Asp Leu Ser
                        610                 615                 620

Lys Ala Asn Asp Ile Lys Leu Pro Phe Leu Gln Gly Ser Gly Ser Ser
        625                 630                 635                 640

Leu Leu Ile Leu Gly Pro Asn Gly Cys Gly Lys Ser Ser Ile Gln Arg
                        645                 650                 655

Ile Ile Ala Glu Ile Trp Pro Val Tyr Asn Lys Asn Gly Leu Leu Ser
                        660                 665                 670

Ile Pro Ser Glu Asn Asn Ile Phe Phe Ile Pro Gln Lys Pro Tyr Phe
                        675                 680                 685

Ser Arg Gly Gly Thr Leu Arg Asp Gln Ile Ile Tyr Pro Met Ser Ser
                        690                 695                 700

Asp Glu Phe Phe Asp Arg Gly Phe Arg Asp Lys Glu Leu Val Gln Ile
        705                 710                 715                 720

Leu Val Glu Val Lys Leu Asp Tyr Leu Leu Lys Arg Gly Val Gly Leu
                        725                 730                 735

Thr Tyr Leu Asp Ala Ile Ala Asp Trp Lys Asp Leu Leu Ser Gly Gly
                        740                 745                 750

Glu Lys Gln Arg Val Asn Phe Ala Arg Ile Met Phe His Lys Pro Leu
                        755                 760                 765

Tyr Val Val Leu Asp Glu Ala Thr Asn Ala Ile Ser Val Asp Met Glu
                        770                 775                 780

Asp Tyr Leu Phe Asn Leu Leu Lys Arg Tyr Arg Phe Asn Phe Ile Ser
        785                 790                 795                 800

Ile Ser Gln Arg Pro Thr Leu Ile Lys Tyr His Glu Met Leu Leu Glu
                        805                 810                 815

Ile Gly Glu Asn Arg Asp Gly Lys Trp Gln Leu Gln Ala Val Gly Thr
                        820                 825                 830

Asp Glu Ala Ile Thr Ser Ile Asp Asn Glu Ile Glu Glu Leu Glu Arg
                        835                 840                 845

Lys Leu Glu Arg Val Lys Gly Trp Glu Asp Glu Arg Thr Lys Leu Arg
        850                 855                 860

Glu Lys Leu Glu Ile Ile
        865                 870

<210> SEQ ID NO 12
<211> LENGTH: 853
<212> TYPE: PRT
<213> ORGANISM: Saccharomyces cerevisiae

<400> SEQUENCE: 12

Met Ile Ser Thr Ala Ser Ala Phe Tyr Gln Lys His Arg Val Asn Leu
        1               5                   10                  15

Leu Arg Ser Ser Tyr Ile Ile Leu Leu Leu Ala Thr Leu Tyr Asn Ser
                        20                  25                  30

Asn Ser Ser Ser Asn Asn Lys Thr Asp Lys Lys Asp Ser Glu Ser
                        35                  40                  45
```

```
Thr Val Leu Glu Asn Lys Lys Ile Glu Glu Gly Lys Glu Thr Ala Val
 50                  55                  60

Asp Arg Glu Glu Asp Glu Ser Ser Lys Glu Glu Leu Thr Ile Val Ser
 65                  70                  75                  80

Lys His Ser Thr Asp Ser Glu Asp Gly Ala Ile Ile Ile Asp Lys Glu
                 85                  90                  95

Ser Lys Thr Asn His Lys Gly Gly Glu Arg Lys Gly Lys Val Asp Phe
            100                 105                 110

Leu Phe Lys Leu Leu His Asp Lys Lys Cys Leu Ile Leu Phe Ile
        115                 120                 125

Thr Gln Ala Ile Leu Leu Asn Ile Arg Thr Leu Leu Ser Leu Arg Val
130                 135                 140

Ala Thr Leu Asp Gly Gln Leu Val Ser Thr Leu Val Arg Ala Gln Tyr
145                 150                 155                 160

Ala Asn Phe Thr Lys Ile Leu Leu Gly Lys Trp Met Ile Leu Gly Ile
                165                 170                 175

Pro Ala Ser Phe Ile Asn Ser Leu Ile Ser Tyr Thr Thr Lys Leu Cys
            180                 185                 190

Ala Val Thr Ile Asn Arg Lys Val Ser Asp Phe Leu Leu Ser Lys Tyr
        195                 200                 205

Leu Ser Asn His His Thr Phe Tyr Ser Val Ala Ser Ala Glu Ser Val
210                 215                 220

Ser Glu Ile Gln Asp Asn Leu Thr Lys Asp Ile Tyr Thr Phe Ser Met
225                 230                 235                 240

Asn Ser Ser Leu Leu Leu Asn Gln Leu Leu Lys Pro Met Leu Asp Leu
                245                 250                 255

Ile Leu Cys Ser Phe Lys Leu Leu Thr Ser Asn Thr Ser Val Met Gly
            260                 265                 270

Glu Gly Thr Leu Ala Leu Gly Leu Ile Val Tyr Ala Ser Asn Ser Leu
        275                 280                 285

Leu Lys Leu Ile Gln Pro Asn Phe Thr Arg Leu Thr Met Ala Ser Ala
290                 295                 300

Ser Leu Glu Ser Trp Phe Arg Ser Leu His Ser Asn Leu His Ser Ser
305                 310                 315                 320

Asn Glu Glu Ile Ala Leu Leu Arg Gly Gln Lys Arg Glu Leu Glu Asn
                325                 330                 335

Val Asp Tyr Ser Phe Tyr Arg Leu Val Leu Phe Leu Asn Arg Glu Ile
            340                 345                 350

Lys Ala Arg Ala Ile Tyr Asp Val Ala Thr Ala Phe Val Ile Lys Tyr
        355                 360                 365

Thr Trp Gly Ala Ala Gly Leu Val Leu Cys Ser Ile Pro Ile Phe Phe
370                 375                 380

Lys Asn Lys Pro Ser Glu Asp Thr Leu Gln Leu Lys Glu Pro Gly Asn
385                 390                 395                 400

Asp Met Thr Ala Asp Phe Ile Thr Asn Arg Arg Leu Leu Val Thr Ala
                405                 410                 415

Ser Ser Ser Ile Gly Arg Phe Val Glu Leu Lys Arg Asn Ile Gln Gln
            420                 425                 430

Leu Arg Gly Ile Arg Leu Arg Leu Asn Lys Phe Asn Asp Leu Leu Asp
        435                 440                 445

Ala Asn Lys Gly Asp Asp Glu Lys Glu Pro Arg Asp Glu Arg Cys Ile
450                 455                 460

Val Glu Tyr Asp Asp Ser Arg Ile Lys Phe Glu Asn Ile Pro Leu Ile
```

```
            465                 470                 475                 480
        Thr Pro Ala Asn Gln Val Leu Val Pro Glu Leu Ser Phe Asp Leu Lys
                        485                 490                 495

His Gly Asn His Leu Ile Ile Gly Pro Asn Gly Cys Gly Lys Ser
                    500                 505                 510

Ser Leu Phe Arg Ile Leu Gly Gly Leu Trp Pro Ile Arg Ala Thr Pro
                        515                 520                 525

Asn Lys Asn His Gln Ser Lys Leu Ile Met Pro Arg Arg Thr Val Asp
                        530                 535                 540

Arg Asp Cys Ala Ile Phe Tyr Leu Pro Gln Arg Pro Tyr Met Gly Asn
        545                 550                 555                 560

Arg Ser Thr Phe Arg Glu Gln Ile Ile Tyr Pro Asp Ser Ile Glu Gln
                        565                 570                 575

Phe Lys Glu Arg Tyr His Asn Asp Tyr Asp Leu Gly Asp Ala Asp Leu
                    580                 585                 590

Ile Lys Ile Leu Gln Leu Leu Asp Leu Glu Asp Leu Val Thr Glu Asn
                    595                 600                 605

Met Ser Leu Leu Leu Ala Gln Arg Thr Ser Lys Asn Asp Ser Gln Gln
            610                 615                 620

Leu Ser Thr Glu Asp Asn Gln Ser Pro Cys Ala Ile Lys Val Arg Asp
        625                 630                 635                 640

Ala Phe Ser Ile Val Arg Asn Trp Ser Glu Glu Leu Thr Ile Gly Val
                        645                 650                 655

Gln Gln Arg Leu Ala Met Ala Arg Met Tyr Tyr His Lys Pro Lys Phe
                    660                 665                 670

Ala Val Leu Asp Glu Cys Thr Ser Ala Val Ala Pro Glu Met Glu Gln
                    675                 680                 685

Arg Met Tyr Glu Asn Ala Gln Asn Phe Gly Ile Ser Leu Ile Ser Val
            690                 695                 700

Cys His Arg Thr Ser Leu Trp His Phe His Asn Tyr Leu Leu Lys Phe
        705                 710                 715                 720

Asp Gly Lys Gly Gly Tyr Gln Phe Gly Pro Phe Asn Pro Lys Glu Arg
                        725                 730                 735

Leu Cys Asn Glu Glu Lys Leu Leu Glu Leu Asn Ala Ile Leu Asp Gln
                    740                 745                 750

Gln Val Pro Leu Trp Glu Arg Lys Leu Lys Asp Leu Thr Ile Ala Lys
                    755                 760                 765

Glu Ser Asn Ile Ile Arg Lys Ser Gly Thr Asn Leu Asn Leu Phe Glu
            770                 775                 780

Lys Ile Glu Asp Pro Lys Thr Ser Lys Ser Asn Ala Leu Phe Asn Ala
        785                 790                 795                 800

Asn Lys Gly Gln Arg Ile Thr Ser Pro Thr Gly Gln Glu Thr Ser Lys
                        805                 810                 815

Arg Leu Pro Leu Phe Ser Gln Pro Ser Ser Ala Ser Ser Asn Leu
                    820                 825                 830

Leu Arg Asn Asn Lys Ser Leu Asn Lys Val Lys Thr Lys Lys Glu
                    835                 840                 845

Glu Gly Lys Glu Arg
            850

<210> SEQ ID NO 13
<211> LENGTH: 760
<212> TYPE: PRT
<213> ORGANISM: Saccharomyces cerevisiae
```

<400> SEQUENCE: 13

```
Met Lys Ile Thr Cys Thr Asp Leu Val Tyr Val Phe Ile Leu Leu Phe
1               5                   10                  15

Leu Asn Thr Ser Cys Val Gln Ala Val Phe Ser Asp Asp Ala Phe Ile
            20                  25                  30

Thr Asp Trp Gln Leu Ala Asn Leu Gly Pro Trp Glu Lys Val Ile Pro
        35                  40                  45

Asp Ser Arg Asp Arg Asn Arg Val Leu Ile Leu Ser Asn Pro Thr Glu
    50                  55                  60

Thr Ser Cys Leu Val Ser Ser Phe Asn Val Ser Ser Gly Gln Ile Leu
65                  70                  75                  80

Phe Arg Asn Val Leu Pro Phe Thr Ile Asp Glu Ile Gln Leu Asp Ser
                85                  90                  95

Asn Asp His Asn Ala Met Val Cys Val Asn Ser Ser Ser Asn His Trp
            100                 105                 110

Gln Lys Phe Asp Leu His Asp Trp Phe Leu Leu Glu Glu Gly Val Asp
        115                 120                 125

Asn Ala Pro Ser Thr Thr Ile Leu Pro Gln Ser Ser Tyr Leu Asn Asp
    130                 135                 140

Gln Val Ser Ile Lys Asn Asn Glu Leu His Ile Leu Asp Glu Gln Ser
145                 150                 155                 160

Lys Leu Ala Glu Trp Lys Leu Glu Leu Pro Gln Gly Phe Asn Lys Val
                165                 170                 175

Glu Tyr Phe His Arg Glu Asp Pro Leu Ala Leu Val Leu Asn Val Asn
            180                 185                 190

Asp Thr Gln Tyr Met Gly Phe Ser Ala Asn Gly Thr Glu Leu Ile Pro
        195                 200                 205

Val Trp Gln Arg Asp Glu Trp Leu Thr Asn Val Val Asp Tyr Ala Val
    210                 215                 220

Leu Asp Val Phe Asp Ser Arg Asp Val Glu Leu Asn Lys Asp Met Lys
225                 230                 235                 240

Ala Glu Leu Asp Ser Asn Ser Leu Trp Asn Ala Tyr Trp Leu Arg Leu
                245                 250                 255

Thr Thr Asn Trp Asn Arg Leu Ile Asn Leu Leu Lys Glu Asn Gln Phe
            260                 265                 270

Ser Pro Gly Arg Val Phe Thr Lys Leu Leu Ala Leu Asp Ala Lys Asp
        275                 280                 285

Thr Thr Val Ser Asp Leu Lys Phe Gly Phe Ala Lys Ile Leu Ile Val
    290                 295                 300

Leu Thr His Asp Gly Phe Ile Gly Gly Leu Asp Met Val Asn Lys Gly
305                 310                 315                 320

Gln Leu Ile Trp Lys Leu Asp Leu Glu Ile Asp Gln Gly Val Lys Met
                325                 330                 335

Phe Trp Thr Asp Lys Asn His Asp Glu Leu Val Val Phe Ser His Asp
            340                 345                 350

Gly His Tyr Leu Thr Ile Glu Val Thr Lys Asp Gln Pro Ile Ile Lys
        355                 360                 365

Ser Arg Ser Pro Leu Ser Glu Arg Lys Thr Val Asp Ser Val Ile Arg
    370                 375                 380

Leu Asn Glu His Asp His Gln Tyr Leu Ile Lys Phe Glu Asp Lys Asp
385                 390                 395                 400

His Leu Leu Phe Lys Leu Asn Pro Gly Lys Asn Thr Asp Val Pro Ile
```

```
                    405                 410                 415
Val Ala Asn Asn His Ser Ser His Ile Phe Val Thr Glu His Asp
                420                 425                 430

Thr Asn Gly Ile Tyr Gly Tyr Ile Ile Glu Asn Asp Thr Val Lys Gln
            435                 440                 445

Thr Trp Lys Lys Ala Val Asn Ser Lys Glu Lys Met Val Ala Tyr Ser
        450                 455                 460

Lys Arg Glu Thr Thr Asn Leu Asn Thr Leu Gly Ile Thr Leu Gly Asp
465                 470                 475                 480

Lys Ser Val Leu Tyr Lys Tyr Leu Tyr Pro Asn Leu Ala Ala Tyr Leu
                485                 490                 495

Ile Ala Asn Glu Glu His His Thr Ile Thr Phe Asn Leu Ile Asp Thr
            500                 505                 510

Ile Thr Gly Glu Ile Leu Ile Thr Gln Glu His Lys Asp Ser Pro Asp
        515                 520                 525

Phe Arg Phe Pro Met Asp Ile Val Phe Gly Glu Tyr Trp Val Val Tyr
    530                 535                 540

Ser Tyr Phe Ser Ser Glu Pro Val Pro Glu Gln Lys Leu Val Val Val
545                 550                 555                 560

Glu Leu Tyr Glu Ser Leu Thr Pro Asp Glu Arg Leu Ser Asn Ser Ser
                565                 570                 575

Asp Asn Phe Ser Tyr Asp Pro Leu Thr Gly His Ile Asn Lys Pro Gln
            580                 585                 590

Phe Gln Thr Lys Gln Phe Ile Phe Pro Glu Ile Ile Lys Thr Met Ser
        595                 600                 605

Ile Ser Lys Thr Thr Asp Asp Ile Thr Thr Lys Ala Ile Val Met Glu
    610                 615                 620

Leu Glu Asn Gly Gln Ile Thr Tyr Ile Pro Lys Leu Leu Leu Asn Ala
625                 630                 635                 640

Arg Gly Lys Pro Ala Glu Glu Met Ala Lys Asp Lys Lys Lys Glu Phe
                645                 650                 655

Met Ala Thr Pro Tyr Thr Pro Val Ile Pro Ile Asn Asp Asn Phe Ile
            660                 665                 670

Ile Thr His Phe Arg Asn Leu Leu Pro Gly Ser Asp Ser Gln Leu Ile
        675                 680                 685

Ser Ile Pro Thr Asn Leu Glu Ser Thr Ile Ile Cys Asp Leu Gly
    690                 695                 700

Leu Asp Val Phe Cys Thr Arg Ile Thr Pro Ser Gly Gln Phe Asp Leu
705                 710                 715                 720

Met Ser Pro Thr Phe Glu Lys Gly Lys Leu Leu Ile Thr Ile Phe Val
                725                 730                 735

Leu Leu Val Ile Thr Tyr Phe Ile Arg Pro Ser Val Ser Asn Lys Lys
            740                 745                 750

Leu Lys Ser Gln Trp Leu Ile Lys
        755                 760

<210> SEQ ID NO 14
<211> LENGTH: 117
<212> TYPE: PRT
<213> ORGANISM: Saccharomyces cerevisiae

<400> SEQUENCE: 14

Met Ser Ser Ser Thr Pro Phe Asp Pro Tyr Ala Leu Ser Glu His Asp
1               5                   10                  15
```

```
Glu Glu Arg Pro Gln Asn Val Gln Ser Lys Ser Arg Thr Ala Glu Leu
             20                  25                  30

Gln Ala Glu Ile Asp Asp Thr Val Gly Ile Met Arg Asp Asn Ile Asn
         35                  40                  45

Lys Val Ala Glu Arg Gly Glu Arg Leu Thr Ser Ile Glu Asp Lys Ala
 50                  55                  60

Asp Asn Leu Ala Val Ser Ala Gln Gly Phe Lys Arg Gly Ala Asn Arg
 65                  70                  75                  80

Val Arg Lys Ala Met Trp Tyr Lys Asp Leu Lys Met Lys Met Cys Leu
                 85                  90                  95

Ala Leu Val Ile Ile Ile Leu Leu Val Val Ile Val Pro Ile Ala
                100                 105                 110

Val His Phe Ser Arg
            115

<210> SEQ ID NO 15
<211> LENGTH: 115
<212> TYPE: PRT
<213> ORGANISM: Saccharomyces cerevisiae

<400> SEQUENCE: 15

Met Ser Ser Ser Val Pro Tyr Asp Pro Tyr Val Pro Glu Glu Ser
 1               5                  10                  15

Asn Ser Gly Ala Asn Pro Asn Ser Gln Asn Lys Thr Ala Ala Leu Arg
             20                  25                  30

Gln Glu Ile Asp Asp Thr Val Gly Ile Met Arg Asp Asn Ile Asn Lys
         35                  40                  45

Val Ala Glu Arg Gly Glu Arg Leu Thr Ser Ile Glu Asp Lys Ala Asp
 50                  55                  60

Asn Leu Ala Ile Ser Ala Gln Gly Phe Lys Arg Gly Ala Asn Arg Val
 65                  70                  75                  80

Arg Lys Gln Met Trp Trp Lys Asp Leu Lys Met Arg Met Cys Leu Phe
                 85                  90                  95

Leu Val Val Ile Ile Leu Leu Val Val Ile Ile Val Pro Ile Val Val
                100                 105                 110

His Phe Ser
115

<210> SEQ ID NO 16
<211> LENGTH: 403
<212> TYPE: PRT
<213> ORGANISM: Saccharomyces cerevisiae

<400> SEQUENCE: 16

Met Thr Ile Ala Pro Met Ala Asn Asp Leu Glu Asp Phe Glu Ser Leu
 1               5                  10                  15

Leu Glu Pro Thr Phe Asp Ala Lys Gln Phe Gly Asn Asp Leu Leu Lys
             20                  25                  30

Ala Thr Asn Asn Asp Thr Thr Ile Leu Asp Leu Asn Thr Pro Leu
         35                  40                  45

Lys Lys Leu Asn Tyr Asp Leu His Glu Ile Asp Ser Arg Ile Asp Gln
 50                  55                  60

Leu Met Asn Ser Asn Pro Leu Glu Ile Ile Glu Leu Ile Tyr Lys Asn
 65                  70                  75                  80

Glu His Val Asn Ser Thr Ile Val Gly Glu Leu Lys Pro Ser Leu Glu
                 85                  90                  95
```

```
Tyr Met Asn Met Ser Tyr Asp Arg Leu Lys Asn Gln Val Leu Asp Pro
            100                 105                 110

Tyr Glu Arg Ala Arg Lys Val Gln Leu Ala Leu Ser Lys Val Tyr Gln
        115                 120                 125

Thr Ser Phe Leu Leu Arg Gly Ala Leu Leu Tyr Ile His Leu Ser Asn
    130                 135                 140

Lys Leu Asn Ala Leu Ser Lys Thr Ala Gln Leu Ser Thr Ser Thr Ala
145                 150                 155                 160

Ile Asn Leu Ala Ser Leu His Tyr Gln Leu Glu Ile Thr Leu Asp Glu
                165                 170                 175

Asn Lys Asn Leu Lys Ser Leu Arg Lys Ile Lys Gln Leu Asp Gln Asp
            180                 185                 190

Ile Val Ser Pro Asn Lys Arg Glu Leu Ile Thr Phe Leu Ser Leu Gln
        195                 200                 205

Met Cys Lys Glu Cys Leu Asn Ser Ile Lys Ile Lys Ser Asn Lys Glu
    210                 215                 220

Ile Ile Ser Gln Leu Ala Tyr Ser Leu Tyr Leu Ser Ser Gln Glu
225                 230                 235                 240

Phe Glu Ser Ala Ile Asn Lys Ile Val Leu Ser Asn Val Thr Met Ser
                245                 250                 255

Ser Gln Ile Leu Ser Lys Ile Leu Asn Ser Ile Arg Met Phe Pro Asp
            260                 265                 270

Ala Phe Asn Glu Val Val Glu Lys Gly Tyr Asn Ile Tyr Ile Leu Glu
        275                 280                 285

Thr Leu Leu Arg Asn Ile Lys Thr Asp Asn Val Thr Asn Ser Ser Arg
    290                 295                 300

Ser Ile Ala Ala Asn Lys Ser Arg Leu Gly Asn Leu Leu Ser Glu Tyr
305                 310                 315                 320

Thr Ser Met Lys Ser Lys Ala Gly Ser Gly Thr Pro Arg Asp Leu Phe
                325                 330                 335

Trp Ser Lys Val Ser Ser Ala Phe Lys Lys Asp Phe Glu Ile Ser Val
            340                 345                 350

Asn Arg Gly Gly Pro Val Gly Lys Ser Leu Leu Lys Asn Lys Asp Phe
        355                 360                 365

Ile Ile Asn Thr Met Lys Gln Ser Met Lys Lys Ser Ser Asp Asn Ser
    370                 375                 380

Asp Tyr Gln Ser Tyr Leu Asp Val Met Leu Asn Ser Val Ser Ile Ser
385                 390                 395                 400

Leu Asn Lys

<210> SEQ ID NO 17
<211> LENGTH: 1569
<212> TYPE: DNA
<213> ORGANISM: Saccharomyces cerevisiae

<400> SEQUENCE: 17
atgaagtttt ctgctggtgc cgtcctgtca tggtcctccc tgctgctcgc ctcctctgtt      60
ttcgcccaac aagaggctgt ggcccctgaa gactccgctg tcgttaagtt ggccaccgac     120
tccttcaatg agtacattca gtcgcacgac ttggtgcttg cggagttttt tgctccatgg     180
tgtggccact gtaagaacat ggctcctgaa tacgttaaag ccgccgagac tttagttgag     240
aaaaacatta ccttggccca gatcgactgt actgaaaacc aggatctgtg tatggaacac     300
aacattccag ggttcccaag cttgaagatt ttcaaaaaca gcgatgttaa caactcgatc     360
```

| | | | | |
|---|---|---|---|---|
| gattacgagg | gacctagaac | tgccgaggcc | attgtccaat | tcatgatcaa gcaaagccaa | 420 |
| ccggctgtcg | ccgttgttgc | tgatctacca | gcttaccttg | ctaacgagac ttttgtcact | 480 |
| ccagttatcg | tccaatccgg | taagattgac | gccgacttca | acgccacctt ttactccatg | 540 |
| gccaacaaac | acttcaacga | ctacgacttt | gtctccgctg | aaaacgcaga cgatgatttc | 600 |
| aagctttcta | tttacttgcc | ctccgccatg | gacgagcctg | tagtatacaa cggtaagaaa | 660 |
| gccgatatcg | ctgacgctga | tgtttttgaa | aatggttgc | aagtggaagc cttgccctac | 720 |
| tttggtgaaa | tcgacggttc | cgttttcgcc | caatacgtcg | aaagcggttt gcctttgggt | 780 |
| tacttattct | acaatgacga | ggaagaattg | aagaataca | agcctctctt taccgagttg | 840 |
| gccaaaaaga | acagaggtct | aatgaacttt | gttagcatcg | atgccagaaa attcggcaga | 900 |
| cacgccggca | acttgaacat | gaaggaacaa | ttccctctat | ttgccatcca cgacatgact | 960 |
| gaagacttga | agtacggttt | gcctcaactc | tctgaagagg | cgtttgacga attgagcgac | 1020 |
| aagatcgtgt | tggagtctaa | ggctattgaa | tctttggtta | aggacttctt gaaaggtgat | 1080 |
| gcctccccaa | tcgtgaagtc | ccaagagatc | ttcgagaacc | aagattcctc tgtcttccaa | 1140 |
| ttggtcggta | agaaccatga | cgaaatcgtc | aacgacccaa | agaaggacgt tcttgttttg | 1200 |
| tactatgccc | catggtgtgg | tcactgtaag | agattggccc | caacttacca agaactagct | 1260 |
| gatacctacg | ccaacgccac | atccgacgtt | ttgattgcta | aactagacca cactgaaaac | 1320 |
| gatgtcagag | gcgtcgtaat | tgaaggttac | ccaacaatcg | tcttataccc aggtggtaag | 1380 |
| aagtccgaat | ctgttgtgta | ccaaggttca | agatccttgg | actctttatt cgacttcatc | 1440 |
| aaggaaaacg | gtcacttcga | cgtcgacggt | aaggccttgt | acgaagaagc ccaggaaaaa | 1500 |
| gctgctgagg | aagccgatgc | tgacgctgaa | ttggctgacg | aagaagatgc cattcacgat | 1560 |
| gaattgtaa | | | | | 1569 |

<210> SEQ ID NO 18
<211> LENGTH: 2502
<212> TYPE: DNA
<213> ORGANISM: Saccharomyces cerevisiae

<400> SEQUENCE: 18

| | | | | |
|---|---|---|---|---|
| atgaataatg | ctgcaaatac | agggacgacc | aatgagtcaa | acgtgagcga tgctccccgt | 60 |
| attgagccttt | taccaagctt | gaatgatgat | gacattgaaa | aaatcttaca accgaacgat | 120 |
| atctttacga | ccgatcgtac | cgatgcaagt | actacatctt | ccacagccat tgaagatatt | 180 |
| attaacccct | cattggatcc | gcagtcagca | gcatcgccgg | ttccttcttc ctctttttc | 240 |
| catgactcaa | ggaaaccttc | caccagtaca | catttagtaa | ggagaggtac tccattggga | 300 |
| atttaccaaa | ccaatctata | cggtcacaat | agcagagaaa | atactaatcc taatagtaca | 360 |
| ttattatctt | ctaagttact | cgcgcatcca | ccagttcctt | atgggcaaaa tcccgattta | 420 |
| ctacaacatg | ctgtgtacag | ggcacagccg | tcaagtggaa | ccactaacgc gcaaccgcgc | 480 |
| caaaccacaa | gaagatatca | atcccataaa | tcacggcctg | catttgttaa taaactatgg | 540 |
| agcatgttaa | acgatgattc | taatacgaaa | cttatacagt | gggcggagga tggaaaatct | 600 |
| tttattgtca | cgaatagga | ggaatttgtg | caccaaattt | taccaaaata ttttaaacat | 660 |
| tccaatttcg | cttcctttgt | aagacaattg | aacatgtatg | gatggcataa agttcaagat | 720 |
| gtcaagtcag | gatcaattca | agtagttca | gatgataagt | ggcaatttga aaatgaaaac | 780 |
| ttcattagag | gtagagaaga | tttgctggaa | aaaataatca | ggcagaaagg ttcctccaat | 840 |
| aaccataata | gccctagtgg | taacggtaat | ccagcgaatg | gtagcaacat ccctctggac | 900 |

```
aatgccgcag gaagtaataa tagcaataat aacatcagta gtagtaattc atttttaac      960
aatggtcatt tattgcaggg taaaacacta agattaatga acgaagcgaa tcttggagat    1020
aagaatgatg tcaccgcgat tttgggggaa ttagagcaaa taaaatataa ccagattgca    1080
atttccaaag atttactaag aataaacaaa gataatgagt tattatggca agagaatatg    1140
atggccaggg aaagacatag aacccaacag caagccttgg aaaaaatgtt cagattcttg    1200
acatctatag tcccacactt agatcccaaa atgattatgg acgggctggg agatccgaaa    1260
gttaataatg aaaagctaaa cagtgcgaat aacattgggt taaatcgcga caacacaggc    1320
actatagatg aactaaaatc caacgattct ttcataaacg atgatcgtaa ttctttcacc    1380
aatgctacaa ccaacgcccg taataacatg agtcccaaca atgatgacaa tagtattgac    1440
accgctagca ctaataccac caacagaaag aaaaatatag atgaaaacat caaaaataac    1500
aacgacataa ttaatgacat tatatttaat accaaccttg ccaacaatct cagcaattac    1560
aattccaaca ataatgctgg ctcgccaata aggccctata acaaagata tcttttgaaa     1620
aatagagcca attcctcgac atcgagtgag aatccaagcc taacgccctt tgatatcgaa    1680
tctaataatg accgcaaaat ttcagaaatt cctttttgatg acgaagaaga agaagaaacg   1740
gattttaggc cttttacctc gcgagatcct aataaccaaa cgagtgaaaa cactttttgat  1800
ccaaacagat ttacgatgct ctctgatgat gatttaaaaa aagattctca taccaatgac   1860
aataaacaca acgaaagtga tctttttttgg gacaacgtac atagaaatat agacgaacaa  1920
gatgcaagac tccagaactt ggaaaatatg gttcacatac tttctcctgg atatcctaat   1980
aagtcgttca acaacaaaac ttcctcgaca aacactaatt ccaatatgga aagtgctgtc    2040
aacgttaata gccctggttt caacttacag gattatttaa ctggagagtc taattccccc    2100
aattctgttc attctgttcc ctccaatggc agcggctcca caccgttgcc catgccaaat   2160
gataatgaca ccgagcacgc aagtacaagt gtcaatcaag gcgaaaatgg aagcggatta   2220
acgcccttcc tcacggtaga tgatcacaca ctaaacgaca ataacactag tgagggaagt   2280
acaagggtgt cccccgatat aaagttcagc gccactgaaa acactaaagt gagtgataac    2340
ctgccaagct ttaatgacca cagttattcc acccaggccg acacggcgcc cgagaacgct   2400
aagaaaagat tgtggagga aataccggaa ccggctatag tcgaaataca ggacccgaca    2460
gagtacaacg atcaccgcct gcccaaacga gctaagaaat ag                       2502
```

<210> SEQ ID NO 19
<211> LENGTH: 238
<212> TYPE: PRT
<213> ORGANISM: Saccharomyces cerevisiae

<400> SEQUENCE: 19

```
Met Glu Met Thr Asp Phe Glu Leu Thr Ser Asn Ser Gln Ser Asn Leu
1               5                   10                  15

Ala Ile Pro Thr Asn Phe Lys Ser Thr Leu Pro Pro Arg Lys Arg Ala
            20                  25                  30

Lys Thr Lys Glu Glu Lys Glu Gln Arg Arg Ile Glu Arg Ile Leu Arg
        35                  40                  45

Asn Arg Arg Ala Ala His Gln Ser Arg Glu Lys Lys Arg Leu His Leu
    50                  55                  60

Gln Tyr Leu Glu Arg Lys Cys Ser Leu Leu Glu Asn Leu Leu Asn Ser
65                  70                  75                  80

Val Asn Leu Glu Lys Leu Ala Asp His Glu Asp Ala Leu Thr Cys Ser
```

```
            85              90              95
His Asp Ala Phe Val Ala Ser Leu Asp Glu Tyr Arg Asp Phe Gln Ser
            100             105             110

Thr Arg Gly Ala Ser Leu Asp Thr Arg Ala Ser Ser His Ser Ser Ser
        115             120             125

Asp Thr Phe Thr Pro Ser Pro Leu Asn Cys Thr Met Glu Pro Ala Thr
    130             135             140

Leu Ser Pro Lys Ser Met Arg Asp Ser Ala Ser Asp Gln Glu Thr Ser
145             150             155             160

Trp Glu Leu Gln Met Phe Lys Thr Glu Asn Val Pro Glu Ser Thr Thr
                165             170             175

Leu Pro Ala Val Asp Asn Asn Asn Leu Phe Asp Ala Val Ala Ser Pro
            180             185             190

Leu Ala Asp Pro Leu Cys Asp Asp Ile Ala Gly Asn Ser Leu Pro Phe
        195             200             205

Asp Asn Ser Ile Asp Leu Asp Asn Trp Arg Asn Pro Glu Ala Gln Ser
    210             215             220

Gly Leu Asn Ser Phe Glu Leu Asn Asp Phe Phe Ile Thr Ser
225             230             235
```

<210> SEQ ID NO 20
<211> LENGTH: 41
<212> TYPE: DNA
<213> ORGANISM: Artificial
<220> FEATURE:
<223> OTHER INFORMATION: Primer

<400> SEQUENCE: 20
actgcggccg caacaaaatg tcttacagag gacctattgg a      41

<210> SEQ ID NO 21
<211> LENGTH: 40
<212> TYPE: DNA
<213> ORGANISM: Artificial
<220> FEATURE:
<223> OTHER INFORMATION: Primer

<400> SEQUENCE: 21
cgtgagctcc tagtaaatct tcttcttttc atcaacggat       40

<210> SEQ ID NO 22
<211> LENGTH: 37
<212> TYPE: DNA
<213> ORGANISM: Artificial
<220> FEATURE:
<223> OTHER INFORMATION: Primer

<400> SEQUENCE: 22
tcaggatcca acaaaatgac aatagcgcca atggcaa          37

<210> SEQ ID NO 23
<211> LENGTH: 45
<212> TYPE: DNA
<213> ORGANISM: Artificial
<220> FEATURE:
<223> OTHER INFORMATION: Primer

<400> SEQUENCE: 23
ccaggtacct cacttattta gagaaataga tactgagttt agcat    45

<210> SEQ ID NO 24

```
<211> LENGTH: 38
<212> TYPE: DNA
<213> ORGANISM: Artificial
<220> FEATURE:
<223> OTHER INFORMATION: Primer

<400> SEQUENCE: 24
actgcggccg caacaaaatg aagttttctg ctggtgcc                              38

<210> SEQ ID NO 25
<211> LENGTH: 37
<212> TYPE: DNA
<213> ORGANISM: Artificial
<220> FEATURE:
<223> OTHER INFORMATION: Primer

<400> SEQUENCE: 25
cgtgagctct tacaattcat cgtgaatggc atcttct                               37

<210> SEQ ID NO 26
<211> LENGTH: 80
<212> TYPE: DNA
<213> ORGANISM: Artificial
<220> FEATURE:
<223> OTHER INFORMATION: Primer

<400> SEQUENCE: 26
atgagtagga aaaattctaa gaaactaaaa gtctattact tacctgtaac gctaacccaa      60
gacatggagg cccagaatac                                                  80

<210> SEQ ID NO 27
<211> LENGTH: 113
<212> TYPE: DNA
<213> ORGANISM: Artificial
<220> FEATURE:
<223> OTHER INFORMATION: Primer

<400> SEQUENCE: 27
aaatctctct atattataca ggctacttct tttaggaaac gtcacattca ttagtcgata      60
gtattgtatc tattttcttt atttttcaca caccagtata gcgaccagca ttc            113

<210> SEQ ID NO 28
<211> LENGTH: 83
<212> TYPE: DNA
<213> ORGANISM: Artificial
<220> FEATURE:
<223> OTHER INFORMATION: Primer

<400> SEQUENCE: 28
atggactacg aggataatct agaagcacct gtttgggacg aactaaatca tgagggagat      60
aaagacatgg aggcccagaa tac                                              83

<210> SEQ ID NO 29
<211> LENGTH: 113
<212> TYPE: DNA
<213> ORGANISM: Artificial
<220> FEATURE:
<223> OTHER INFORMATION: Primer

<400> SEQUENCE: 29
ataaatcctg aggaacgtga cacataaagt tattgtatac agatcatcta ttaggcttgt      60
tattgcagga tgtatgaaag tttataaaat ccccagtata gcgaccagca ttc            113
```

```
<210> SEQ ID NO 30
<211> LENGTH: 84
<212> TYPE: DNA
<213> ORGANISM: Artificial
<220> FEATURE:
<223> OTHER INFORMATION: Primer

<400> SEQUENCE: 30
atgagctcac aaccgtctttt cgtcaccata agggggcaagg ccatttctct agaaacacaa      60
acgggacatg gaggcccaga atac                                              84

<210> SEQ ID NO 31
<211> LENGTH: 113
<212> TYPE: DNA
<213> ORGANISM: Artificial
<220> FEATURE:
<223> OTHER INFORMATION: Primer

<400> SEQUENCE: 31
agattcttgt tatgttttta catacgttgt ttaataaaag tcgttattta tcagtggtgt       60
ggttgcttgt ctggaattgg cttttccct gtgcagtata gcgaccagca ttc              113

<210> SEQ ID NO 32
<211> LENGTH: 82
<212> TYPE: DNA
<213> ORGANISM: Artificial
<220> FEATURE:
<223> OTHER INFORMATION: Primer

<400> SEQUENCE: 32
atgggtgaag attttatgca cccaccgttt caaacgtacc cttcaaagaa cagcgaaggg      60
aagacatgga ggcccagaat ac                                              82

<210> SEQ ID NO 33
<211> LENGTH: 113
<212> TYPE: DNA
<213> ORGANISM: Artificial
<220> FEATURE:
<223> OTHER INFORMATION: Primer

<400> SEQUENCE: 33
caaatttgtg catatacttt tcttgacctt attactcctc ggcttgatta tcattataaa      60
cactattcct tctgttgctt ggttaaaatg ctacagtata gcgaccagca ttc            113

<210> SEQ ID NO 34
<211> LENGTH: 92
<212> TYPE: DNA
<213> ORGANISM: Artificial
<220> FEATURE:
<223> OTHER INFORMATION: Primer

<400> SEQUENCE: 34
atgacttcgg ctgtaccttta tgatccatat gatgatctgg ataacaatcc atttgctgag    60
ccccaggagg aagacatgga ggcccagaat ac                                   92

<210> SEQ ID NO 35
<211> LENGTH: 117
<212> TYPE: DNA
<213> ORGANISM: Artificial
<220> FEATURE:
<223> OTHER INFORMATION: Primer

<400> SEQUENCE: 35
```

```
aaagatcacc ttgttcaaag gtatgaatt tctactttat atacgtatta tcatgttcag    60
aggatagatg gattgactaa gggtacagta cggcaaacag tatagcgacc agcattc     117
```

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36

```
gacatggagg cccagaatac                                               20
```

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37

```
cagtatagcg accagcattc                                               20
```

<210> SEQ ID NO 38
<211> LENGTH: 117
<212> TYPE: DNA
<213> ORGANISM: Artificial
<220> FEATURE:
<223> OTHER INFORMATION: Primer

<400> SEQUENCE: 38

```
ttctagaaga tgagagaaga gggaataatg agaaaggcga aaaataaagg cacacaccat   60
agcttcaaaa tgtttctact ccttttttac tcttccagac atggaggccc agaatac     117
```

<210> SEQ ID NO 39
<211> LENGTH: 87
<212> TYPE: DNA
<213> ORGANISM: Artificial
<220> FEATURE:
<223> OTHER INFORMATION: Primer

<400> SEQUENCE: 39

```
aagttaagtg cgcagaaagt aatatcatgc gtcaatcgta tgtgaatgct ggtcgctata   60
ctggcacaca ccatagcttc aaaatgt                                       87
```

<210> SEQ ID NO 40
<211> LENGTH: 24
<212> TYPE: DNA
<213> ORGANISM: Artificial
<220> FEATURE:
<223> OTHER INFORMATION: Primer

<400> SEQUENCE: 40

```
gacaaacttg gaatgtaagg cttc                                          24
```

<210> SEQ ID NO 41
<211> LENGTH: 118
<212> TYPE: DNA
<213> ORGANISM: Artificial
<220> FEATURE:
<223> OTHER INFORMATION: Primer

<400> SEQUENCE: 41

```
atttttgtt agacatataa ttttatatca ttattcttat tattcttata ggaagtacct    60
```
tcaaagaatg gggtcttatc ttgttttgca agtaccacga catggaggcc cagaatac    118

<210> SEQ ID NO 42
<211> LENGTH: 88
<212> TYPE: DNA
<213> ORGANISM: Artificial
<220> FEATURE:
<223> OTHER INFORMATION: Primer

<400> SEQUENCE: 42
aagttaagtg cgcagaaagt aatatcatgc gtcaatcgta tgtgaatgct ggtcgctata    60
ctgggaagta ccttcaaaga atggggtc    88

<210> SEQ ID NO 43
<211> LENGTH: 25
<212> TYPE: DNA
<213> ORGANISM: Artificial
<220> FEATURE:
<223> OTHER INFORMATION: Primer

<400> SEQUENCE: 43
tatctccaat gggttgctat tcatc    25

<210> SEQ ID NO 44
<211> LENGTH: 118
<212> TYPE: DNA
<213> ORGANISM: Artificial
<220> FEATURE:
<223> OTHER INFORMATION: Primer

<400> SEQUENCE: 44 gcatttgtt gtgctgttac aaccacaaca aaacgaaaaa cccgtatgga tccaactggc    60
accgctggct tgaacaacaa taccagcctt ccaacttcga catggaggcc cagaatac    118

<210> SEQ ID NO 45
<211> LENGTH: 84
<212> TYPE: DNA
<213> ORGANISM: Artificial
<220> FEATURE:
<223> OTHER INFORMATION: Primer

<400> SEQUENCE: 45
aagttaagtg cgcagaaagt aatatcatgc gtcaatcgta tgtgaatgct ggtcgctata    60
ctgtccaact ggcaccgctg gctt    84

<210> SEQ ID NO 46
<211> LENGTH: 117
<212> TYPE: DNA
<213> ORGANISM: Artificial
<220> FEATURE:
<223> OTHER INFORMATION: Primer

<400> SEQUENCE: 46
acagcctctt gttgggcgaa acagaggag gcgagcagca gggaggacca tgacaggacg    60
gcaccagcag aaaacttcat tttgaatatg tattacttgg ttatggttat atatgac    117

<210> SEQ ID NO 47
<211> LENGTH: 118
<212> TYPE: DNA
<213> ORGANISM: Artificial
<220> FEATURE:
<223> OTHER INFORMATION: Primer -continued

<400> SEQUENCE: 47
gttcaatagt gtggttggta accaaatttt ctaggcgttg ttgaaaataa tcattagtgc    60
ccaccgtttg agcgtggtgt gacaccacgc ccaagataga catggaggcc cagaatac    118

<210> SEQ ID NO 48
<211> LENGTH: 95
<212> TYPE: DNA
<213> ORGANISM: Artificial
<220> FEATURE:
<223> OTHER INFORMATION: Primer

<400> SEQUENCE: 48
cccagatgcg aagttaagtg cgcagaaagt aatatcatgc gtcaatcgta tgtgaatgct    60
ggtcgctata ctgtcattag tgcccaccgt ttgag                              95

<210> SEQ ID NO 49
<211> LENGTH: 99
<212> TYPE: DNA
<213> ORGANISM: Artificial
<220> FEATURE:
<223> OTHER INFORMATION: Primer

<400> SEQUENCE: 49
attacgaaat ggcctgtatg ggtagattct tgttatgttt ttacatacgt tgtttaataa    60
aagtcgttat tcaattacaa ttcatcgtga atggcatct                          99

<210> SEQ ID NO 50
<211> LENGTH: 21
<212> TYPE: DNA
<213> ORGANISM: Artificial
<220> FEATURE:
<223> OTHER INFORMATION: Primer

<400> SEQUENCE: 50
cccagatgcg aagttaagtg c                                             21

<210> SEQ ID NO 51
<211> LENGTH: 25
<212> TYPE: DNA
<213> ORGANISM: Artificial
<220> FEATURE:
<223> OTHER INFORMATION: Primer

<400> SEQUENCE: 51
attacgaaat ggcctgtatg ggtag                                         25

<210> SEQ ID NO 52
<211> LENGTH: 118
<212> TYPE: DNA
<213> ORGANISM: Artificial
<220> FEATURE:
<223> OTHER INFORMATION: Primer

<400> SEQUENCE: 52
tactcttgtt caatcagtta gttatctttg ttcaatagtg tggttggtaa gcacacacca    60
tagcttcaaa atgtttctac tccttttta ctcttccaga catggaggcc cagaatac     118

<210> SEQ ID NO 53
<211> LENGTH: 97
<212> TYPE: DNA
<213> ORGANISM: Artificial
<220> FEATURE:
<223> OTHER INFORMATION: Primer

```
<400> SEQUENCE: 53
cccagatgcg aagttaagtg cgcagaaagt aatatcatgc gtcaatcgta tgtgaatgct    60
ggtcgctata ctggcacaca ccatagcttc aaaatgt                              97

<210> SEQ ID NO 54
<211> LENGTH: 100
<212> TYPE: DNA
<213> ORGANISM: Artificial
<220> FEATURE:
<223> OTHER INFORMATION: Primer

<400> SEQUENCE: 54
attacgaaat ggcctgtatg ggtagattct tgttatgttt ttacatacgt tgtttaataa    60
aagtcgttat tcattacaat tcatcgtgaa tggcatcttc                          100

<210> SEQ ID NO 55
<211> LENGTH: 20
<212> TYPE: DNA
<213> ORGANISM: Artificial
<220> FEATURE:
<223> OTHER INFORMATION: Primer

<400> SEQUENCE: 55
ttaccacggt gctccagttg                                                 20

<210> SEQ ID NO 56
<211> LENGTH: 20
<212> TYPE: DNA
<213> ORGANISM: Artificial
<220> FEATURE:
<223> OTHER INFORMATION: Primer

<400> SEQUENCE: 56
aaccaagtca gcagcagaag                                                 20

<210> SEQ ID NO 57
<211> LENGTH: 20
<212> TYPE: DNA
<213> ORGANISM: Artificial
<220> FEATURE:
<223> OTHER INFORMATION: Primer

<400> SEQUENCE: 57
tgcggcacag aagagtaacc                                                 20

<210> SEQ ID NO 58
<211> LENGTH: 20
<212> TYPE: DNA
<213> ORGANISM: Artificial
<220> FEATURE:
<223> OTHER INFORMATION: Primer

<400> SEQUENCE: 58
ggcgataaac gataggcaac                                                 20

<210> SEQ ID NO 59
<211> LENGTH: 22
<212> TYPE: DNA
<213> ORGANISM: Artificial
<220> FEATURE:
<223> OTHER INFORMATION: Primer

<400> SEQUENCE: 59
```
tccgctaaga acaactaagt ga    22

<210> SEQ ID NO 60
<211> LENGTH: 22
<212> TYPE: DNA
<213> ORGANISM: Artificial
<220> FEATURE:
<223> OTHER INFORMATION: Primer

<400> SEQUENCE: 60
cactggctgt aaacggacct at    22

<210> SEQ ID NO 61
<211> LENGTH: 21
<212> TYPE: DNA
<213> ORGANISM: Artificial
<220> FEATURE:
<223> OTHER INFORMATION: Primer

<400> SEQUENCE: 61
tgcaaaccca gtgtaagacg c    21

<210> SEQ ID NO 62
<211> LENGTH: 22
<212> TYPE: DNA
<213> ORGANISM: Artificial
<220> FEATURE:
<223> OTHER INFORMATION: Primer

<400> SEQUENCE: 62
atatggttcg agaacaggca tc    22

<210> SEQ ID NO 63
<211> LENGTH: 22
<212> TYPE: DNA
<213> ORGANISM: Artificial
<220> FEATURE:
<223> OTHER INFORMATION: Primer

<400> SEQUENCE: 63
agcacgacat agaagtgaaa cc    22

<210> SEQ ID NO 64
<211> LENGTH: 22
<212> TYPE: DNA
<213> ORGANISM: Artificial
<220> FEATURE:
<223> OTHER INFORMATION: Primer

<400> SEQUENCE: 64
cgcaagggca aacaggatag ac    22

<210> SEQ ID NO 65
<211> LENGTH: 21
<212> TYPE: DNA
<213> ORGANISM: Artificial
<220> FEATURE:
<223> OTHER INFORMATION: Primer

<400> SEQUENCE: 65
cgattgagtc gaacaccctg a    21

<210> SEQ ID NO 66
<211> LENGTH: 19
<212> TYPE: DNA
<213> ORGANISM: Artificial

```
<220> FEATURE:
<223> OTHER INFORMATION: Primer

<400> SEQUENCE: 66
cttgggtgcg taggtctgg                                                19

<210> SEQ ID NO 67
<211> LENGTH: 22
<212> TYPE: DNA
<213> ORGANISM: Artificial
<220> FEATURE:
<223> OTHER INFORMATION: Primer

<400> SEQUENCE: 67
gtcttgtaac caatggcgaa ac                                            22

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68
gccaccacga ttgacgaaca                                               20

<210> SEQ ID NO 69
<211> LENGTH: 22
<212> TYPE: DNA
<213> ORGANISM: Artificial
<220> FEATURE:
<223> OTHER INFORMATION: Primer

<400> SEQUENCE: 69
ttaacagcga cttgcccaca gg                                            22

<210> SEQ ID NO 70
<211> LENGTH: 21
<212> TYPE: DNA
<213> ORGANISM: Artificial
<220> FEATURE:
<223> OTHER INFORMATION: Primer

<400> SEQUENCE: 70
agctagtctg tgacctgtac g                                             21

<210> SEQ ID NO 71
<211> LENGTH: 26
<212> TYPE: DNA
<213> ORGANISM: Artificial
<220> FEATURE:
<223> OTHER INFORMATION: Primer

<400> SEQUENCE: 71
tgcacgtgat aatatgttac cctgtc                                        26

<210> SEQ ID NO 72
<211> LENGTH: 26
<212> TYPE: DNA
<213> ORGANISM: Artificial
<220> FEATURE:
<223> OTHER INFORMATION: Primer

<400> SEQUENCE: 72
ggaggaggat gagataagta gtttcc                                        26
```

```
<210> SEQ ID NO 73
<211> LENGTH: 22
<212> TYPE: DNA
<213> ORGANISM: Artificial
<220> FEATURE:
<223> OTHER INFORMATION: Primer

<400> SEQUENCE: 73
aaaactctgg cggctaaact gg                                              22

<210> SEQ ID NO 74
<211> LENGTH: 25
<212> TYPE: DNA
<213> ORGANISM: Artificial
<220> FEATURE:
<223> OTHER INFORMATION: Primer

<400> SEQUENCE: 74
catcaatact ggcgataagc gggac                                           25

<210> SEQ ID NO 75
<211> LENGTH: 27
<212> TYPE: DNA
<213> ORGANISM: Artificial
<220> FEATURE:
<223> OTHER INFORMATION: Primer

<400> SEQUENCE: 75
tccttggact ctttattcga cttcatc                                         27

<210> SEQ ID NO 76
<211> LENGTH: 22
<212> TYPE: DNA
<213> ORGANISM: Artificial
<220> FEATURE:
<223> OTHER INFORMATION: Primer

<400> SEQUENCE: 76
cgcattataa gtggtgtgcc ga                                              22

<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77
atgctgtgct tgggtgtttt ga                                              22
```